United States Patent
Watarai et al.

(10) Patent No.: US 11,631,895 B2
(45) Date of Patent: Apr. 18, 2023

(54) NONAQUEOUS ELECTROLYTE SOLUTION AND ENERGY DEVICE USING SAME

(71) Applicants: MITSUBISHI CHEMICAL CORPORATION, Chiyoda-ku (JP); MU IONIC SOLUTIONS CORPORATION, Chiyoda-ku (JP)

(72) Inventors: Atsushi Watarai, Chiyoda-ku (JP); Hiroyuki Tokuda, Chiyoda-ku (JP); Akiko Yabe, Chiyoda-ku (JP)

(73) Assignees: MITSUBISHI CHEMICAL CORPORATION, Chiyoda-ku (JP); MU IONIC SOLUTIONS CORPORATION, Chiyoda-ku (JP)

(*) Notice: Subject to any disclaimer, the term of this patent is extended or adjusted under 35 U.S.C. 154(b) by 252 days.

(21) Appl. No.: 16/870,240

(22) Filed: May 8, 2020

(65) Prior Publication Data
US 2020/0274199 A1 Aug. 27, 2020

Related U.S. Application Data

(63) Continuation of application No. PCT/JP2018/041557, filed on Nov. 8, 2018.

(30) Foreign Application Priority Data

Nov. 10, 2017 (JP) .............................. JP2017-217771
Jan. 12, 2018 (JP) .............................. JP2018-003777

(51) Int. Cl.

| | | |
|---|---|---|
| H01M 10/0567 | (2010.01) | |
| C07D 323/00 | (2006.01) | |
| H01G 11/06 | (2013.01) | |
| H01G 11/32 | (2013.01) | |
| H01G 11/46 | (2013.01) | |
| H01G 11/60 | (2013.01) | |
| H01G 11/64 | (2013.01) | |
| H01M 4/38 | (2006.01) | |
| H01M 4/485 | (2010.01) | |
| H01M 4/587 | (2010.01) | |

(52) U.S. Cl.
CPC ...... *H01M 10/0567* (2013.01); *C07D 323/00* (2013.01); *H01G 11/06* (2013.01); *H01G 11/32* (2013.01); *H01G 11/46* (2013.01); *H01G 11/60* (2013.01); *H01G 11/64* (2013.01); *H01M 4/386* (2013.01); *H01M 4/485* (2013.01); *H01M 4/587* (2013.01); *H01M 2300/0025* (2013.01)

(58) Field of Classification Search
None
See application file for complete search history.

(56) References Cited

U.S. PATENT DOCUMENTS

| | | |
|---|---|---|
| 3,511,716 A | 5/1970 | Gabano et al. |
| 2011/0274987 A1 | 11/2011 | Ihara et al. |
| 2014/0212771 A1* | 7/2014 | Garsuch ................ H01M 4/139 429/188 |
| 2016/0009860 A1 | 1/2016 | Fevre et al. |
| 2016/0013517 A1* | 1/2016 | Nakazawa ............ H01M 4/405 429/188 |
| 2017/0158811 A1 | 6/2017 | Fevre et al. |
| 2017/0222263 A1 | 8/2017 | Sakurai et al. |

FOREIGN PATENT DOCUMENTS

| | | |
|---|---|---|
| CN | 103748708 A | 4/2014 |
| CN | 105074994 A | 11/2015 |
| CN | 107069094 A | 8/2017 |
| DE | 31 03 135 A1 | 8/1982 |
| GB | 1 208 934 | 10/1970 |
| JP | 1-320780 A | 12/1989 |
| JP | 11-67270 A | 3/1999 |
| JP | 2002-237328 A | 8/2002 |
| JP | 2005-63871 A | 3/2005 |
| JP | 2011-216406 A | 10/2011 |
| JP | 2015-37018 A | 2/2015 |
| KR | 10-2016-0050222 A | 5/2016 |
| WO | WO 2013/027155 A1 | 2/2013 |
| WO | WO2015046174 A1 | 4/2015 |
| WO | WO 2015/136855 A1 | 9/2015 |

OTHER PUBLICATIONS

International Preliminary Report on Patentability and Written Opinion dated May 12, 2020 in PCT/JP2018/041557 (English Translation only), 5 pages.
International Search Report dated Dec. 18, 2018 in PCT/JP2018/041557 filed Nov. 8, 2018, 1 page.
Partial Supplementary European Search Report dated Nov. 4, 2020 in European Patent Application No. 18877204.0, 12 pages.
Extended European Search Report dated Jan. 28, 2021 in European Patent Application No. 18877204.0, 15 pages.
Xianming Wang, et al., "Electrochemical Behavior of Lithium Imide/Cyclic Ether Electrolytes for 4 V Lithium Metal Rechargeable Batteries," Journal of The Electrochemical Society, vol. 146, No. 11, XP55766227, 1999, 8 pages.
Office Action dated Jun. 28, 2022, in corresponding Japanese Patent Application No. 2019-552384 (with English Translation), 6 pages.
Office Action issued in Chinese Patent Application No. 201880072661.1, dated Nov. 4, 2022 (w/ English language-machine translation).

* cited by examiner

*Primary Examiner* — Daniel S Gatewood
(74) *Attorney, Agent, or Firm* — Oblon, McClelland, Maier & Neustadt, L.L.P.

(57) ABSTRACT

The present invention provides an energy device having excellent properties. Also provided is a nonaqueous electrolyte solution containing a compound represented by the following Formula (1), wherein $R^{11}$, $R^{12}$ and $R^{13}$ each independently represent an organic group having 1 to 3 carbon atoms; and $R^{11}$ and $R^{12}$, $R^{11}$ and $R^{13}$, or $R^{12}$ and $R^{13}$ are optionally bound with each other to form a 5-membered ring or a 6-membered ring, with a proviso that a total number of carbon atoms of $R^{11}$, $R^{12}$ and $R^{13}$ is 7 or less.

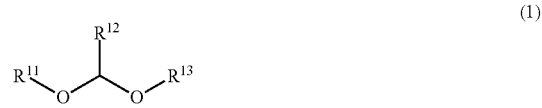

(1)

17 Claims, No Drawings

NONAQUEOUS ELECTROLYTE SOLUTION AND ENERGY DEVICE USING SAME

CROSS-REFERENCE TO RELATED APPLICATION

This is a continuation of International Application PCT/JP2018/041557, filed on Nov. 8, 2018, and designated the U.S., and claims priority from Japanese Patent Application 2017-217771 which was filed on Nov. 10, 2017 and Japanese Patent Application 2018-003777 which was filed on Jan. 12, 2018, the entire contents of which are incorporated herein by reference.

TECHNICAL FIELD

The present invention relates to a nonaqueous electrolyte solution, and an energy device using the same.

BACKGROUND ART

Energy devices in which a nonaqueous electrolyte solution is used, such as nonaqueous electrolyte secondary batteries, electric double-layer capacitors and lithium ion capacitors, have been put into practical use in a wide range of applications including so-called consumer power sources of portable phones, laptop computers and the like, as well as vehicle-mounted power sources for driving automobiles and the like, and stationary large-sized power sources. However, in recent years, there is an increasing demand for performance improvement of these energy devices.

For example, in lithium nonaqueous electrolyte secondary batteries, nonaqueous electrolyte solutions that contain a nonaqueous solvent, such as a cyclic carbonate (e.g., ethylene carbonate or propylene carbonate), an open-chain carbonate (e.g., dimethyl carbonate, diethyl carbonate, or ethyl methyl carbonate), a cyclic carboxylic acid ester (e.g., γ-butyrolactone or γ-valerolactone) or an open-chain carboxylic acid ester (e.g., methyl acetate, ethyl acetate, or methyl propionate), and a solute (electrolyte), such as $LiPF_6$ or $LiBF_4$, are used.

In energy devices in which a nonaqueous electrolyte solution is used, such as the above-described nonaqueous electrolyte secondary batteries, since the reactivity varies depending on the composition of the nonaqueous electrolyte solution, the characteristics are greatly variable depending on the nonaqueous electrolyte solution. Aiming at improving the battery characteristics of energy devices, such as load characteristics, cycle characteristics and storage characteristics, and enhancing the safety of batteries in an overcharged state, various studies have been conducted on nonaqueous solvents and electrolytes that are contained in nonaqueous electrolyte solutions.

For example, Patent Document 1 discloses a technology of using an electrolyte solution containing at least one additive selected from the group consisting of lithium monofluorophosphate and lithium difluorophosphate to inhibit decomposition of a nonaqueous electrolyte solution and to improve the post-storage capacity retention rate (residual capacity ratio).

Further, particularly in nonaqueous electrolyte secondary batteries, it is demanded to satisfy various battery properties, such as durability (e.g., cycle characteristics and storage characteristics) and safety, at high levels.

As means for improving the properties of a nonaqueous electrolyte secondary battery, such as capacity, battery swelling, elution of positive electrode metal and safety in a durability test for cycle characteristics, storage characteristics and the like, numerous technologies have been studied on various battery constituents, including active materials of positive and negative electrodes as well as nonaqueous electrolyte solutions.

For example, Patent Document 2 discloses a technology of using crown ether in an electrolyte solution to form a dense coating film on the negative electrode surface and to thereby improve the storage characteristics of a nonaqueous electrolyte secondary battery.

Moreover, Patent Document 3 discloses a technology of introducing crown ether to a biphenyl-containing electrolyte solution in a battery that includes a positive electrode composed of a transition metal composite oxide containing Ni, Mn and Co and allowing crown ether to take up eluted Mn ions so as to inhibit precipitation of Mn ions on the negative electrode surface in the form of Mn.

CITATION LIST

Patent Documents

[Patent Document 1] Japanese Unexamined Patent Application Publication No. H11-67270
[Patent Document 2] Japanese Unexamined Patent Application Publication No. 2005-63871
[Patent Document 3] Japanese Unexamined Patent Application Publication No. 2015-37018

SUMMARY OF INVENTION

Technical Problem

There is an increasing demand for improvement of the properties of energy devices in recent years, and energy devices are desired to have various performances at high levels; however, such an energy device has yet to be realized, including the technology disclosed in the above-described Patent Document 1. Particularly, there is a problem that it is difficult to simultaneously attain properties of, for example, a reduced resistance and a shortened charging time even after the use, and improved high-current characteristics.

The present invention was made in view of the above-described problems. That is, a first object of the present invention is to provide an energy device that has a low resistance and excellent discharge performance.

Further, as described above, in association with the recent increasing demand for superior performance in nonaqueous electrolyte secondary batteries, it is desired to further improve the performance of nonaqueous electrolyte secondary batteries, namely an improvement in the capacity retention rate under endurance conditions of cycle operation, storage and the like as well as a reduction of battery swelling that also relates to safety improvement, and it is essential to inhibit metal elution from a positive electrode, which is one of the fundamental causes of the swelling.

However, the compounds disclosed in Patent Document 2 and 3 and nonaqueous electrolyte batteries using an electrolyte solution containing the compounds are hardly satisfactory in terms of improvement of the capacity retention rate, inhibition of battery swelling, and reduction in the metal elution from a positive electrode under endurance conditions.

The reasons for this have not been completely elucidated at present; however, they are presumed to be as follows. That is, crown ether has a low oxidation resistance and thus undergoes an oxidation reaction on the positive electrode surface. The resulting side reaction component yields carbon dioxide gas to cause gas swelling during high-temperature storage, which can accelerate the deterioration of the battery under endurance conditions and compromise the safety of the battery.

In addition, this side reaction component may yield a solid substance. In this case, it is expected that the solid substance is deposited on the electrode surface to hinder the insertion and desorption reactions of lithium ions into and from the electrode active material. In other words, the solid substance acts as a resistance component for occlusion and release of lithium ions on the positive electrode to deteriorate the charge-discharge characteristics, causing a reduction in the storage capacity and the storage capacity retention rate and deterioration of the rate characteristics and the input-output characteristics.

Moreover, when crown ether is oxidized on the positive electrode surface, the transition metal oxide constituting the positive electrode has a structure that readily dissolves in the electrolyte solution due to a reduction of the metal valency, and this leads to an increase in the amount of metal elution. Such metal elution can induce disintegration of the negative electrode coating film, reducing the battery capacity and causing a micro-short-circuit to compromise the safety.

Particularly, in recent batteries in which the positive electrode operating potential is increased for attaining a high energy density, the side reaction of crown ether readily occurs; therefore, the generation of carbon dioxide gas, a reduction in the storage capacity and the storage capacity retention rate, an increase in the amount of metal elution, and deterioration of the battery safety are more prominent.

In view of the above-described prior art, a second object of the present invention is to provide a nonaqueous electrolyte solution which greatly improves the capacity retention rate, battery swelling and metal elution during cycle operation and high-temperature storage as compared to the prior art.

Solution to Problem

The present inventors intensively studied to solve the above-described problems and consequently discovered that the problems can be solved by incorporating the below-described specific compound into a nonaqueous electrolyte solution, thereby completing the present invention.

A first embodiment of the present invention provides the below-described nonaqueous electrolyte solution and energy device.

<1> A nonaqueous electrolyte solution containing a compound represented by the following Formula (1):

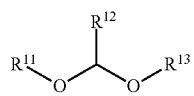

(1)

(wherein $R^{11}$, $R^{12}$ and $R^{13}$ each independently represent an organic group having 1 to 3 carbon atoms; and $R^{11}$ and $R^{12}$, $R^{11}$ and $R^{13}$, or $R^{12}$ and $R^{13}$ are optionally bound with each other to form a 5-membered ring or a 6-membered ring, with a proviso that a total number of carbon atoms of $R^{11}$, $R^{12}$ and $R^{13}$ is 7 or less).

<2> The nonaqueous electrolyte solution according to <1>, wherein a total content of the compound represented by Formula (1) is 0.05 ppm by mass to 50 ppm by mass with respect to a total amount of the nonaqueous electrolyte solution.

<3> The nonaqueous electrolyte solution according to <1> or <2>, further containing at least one compound selected from the group consisting of a fluorine atom-containing cyclic carbonate, a carbon-carbon unsaturated bond-containing cyclic carbonate, a difluorophosphate salt, a fluorosulfate salt, an isocyanate group-containing compound, a cyano group-containing compound, a cyclic sulfonate ester, and a dicarboxylic acid complex salt.

<4> The nonaqueous electrolyte solution according to any one of <1> to <3>, wherein, in Formula (1), $R^{11}$, $R^{12}$ and $R^{13}$ are each independently an organic group having 1 to 2 carbon atoms, and the total number of carbon atoms of $R^{11}$, $R^{12}$ and $R^{13}$ is 5 or less.

<5> An energy device including: plural electrodes capable of absorbing and releasing metal ions; and a nonaqueous electrolyte solution,
wherein the nonaqueous electrolyte solution is the nonaqueous electrolyte solution according to any one of <1> to <4>.

<6> The energy device according to <5>, wherein
the plural electrodes capable of absorbing and releasing metal ions are a positive electrode capable of absorbing and releasing metal ions and a negative electrode capable of absorbing and releasing metal ions, and
the negative electrode contains a carbonaceous material or a silicon-containing material.

<7> The energy device according to <5> or <6>, wherein
the plural electrodes capable of absorbing and releasing metal ions are a positive electrode capable of absorbing and releasing metal ions and a negative electrode capable of absorbing and releasing metal ions, and
the positive electrode contains a transition metal oxide.

Further, the present inventors intensively studied to solve the above-described problems and consequently discovered that the capacity retention rate, battery swelling and metal elution during cycle operation and high-temperature storage are greatly improved over the prior art by incorporating a cyclic compound that contains a carbonate ester structure and an ether structure in one molecule into a nonaqueous electrolyte solution that contains an electrolyte and a nonaqueous solvent dissolving the electrolyte, thereby completing the present invention.

More particularly, in order to develop a novel nonaqueous electrolyte solution that greatly improves the capacity, battery swelling and metal elution in cycle operation and storage over the prior art, the present inventors conducted various studies on the actions and effects of various compounds and combinations thereof, focusing on the formation mechanism and elementary reaction rate of a negative electrode coating film of a nonaqueous electrolyte secondary battery used as an energy device.

Further, based on a novel idea of incorporating at least one cyclic compound that contains a carbonate ester structure and an ether structure in one molecule into a nonaqueous electrolyte solution, the present inventors developed a technology that greatly improves the capacity, battery swelling and metal elution under endurance conditions over the prior art. As a result, the present inventors established a technology that greatly improves the capacity, battery swelling and metal elution in cycle operation and high-temperature storage as compared to the prior art by using a cyclic compound that contains both a carbonate ester structure and an ether structure in one molecule, rather than independently introducing each of a compound having a carbonate ester structure and a compound having a cyclic ether structure to a nonaqueous electrolyte solution.

That is, a second embodiment of the present invention provides, for example, the following specific modes of [A1] to [A9].

[A1] A nonaqueous electrolyte solution containing at least one compound selected from the group consisting of compounds represented by the following Formulae (a1) and (a2):

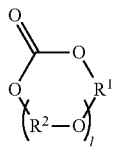

(a1)

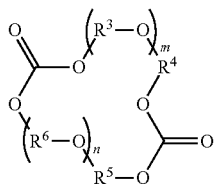

(a2)

(wherein, $R^1$ to $R^6$ each independently represent an alkylene group having 2 to 4 carbon atoms, which may be straight-chain or branched-chain; l represents an integer of 1 to 6; and m and n each represent an integer of 0 to 6, with a proviso that, when either of m and n is 0, the other is an integer of 1 or larger).

[A2] The nonaqueous electrolyte solution according to [A1], further containing a fluorine atom-containing cyclic carbonate.

[A3] The nonaqueous electrolyte solution according to [A1] or [A2], further containing a carbon-carbon unsaturated bond-containing cyclic carbonate.

[A4] The nonaqueous electrolyte solution according to any one of [A1] to [A3], further containing two or more kinds of lithium salts.

[A5] The nonaqueous electrolyte solution according to any one of [A1] to [A4], further containing an isocyanate group-containing compound.

[A6] The nonaqueous electrolyte solution according to any one of [A1] to [A5], further containing a cyano group-containing compound.

[A7] The nonaqueous electrolyte solution according to any one of [A1] to [A6], further containing an $SO_2$ group-containing cyclic compound.

[A8] An energy device including: plural electrodes capable of absorbing and releasing metal ions; and a nonaqueous electrolyte solution,
wherein the nonaqueous electrolyte solution is the nonaqueous electrolyte solution according to any one of [A1] to [A7].

[A9] The energy device according to [A8], wherein
the plural electrodes capable of absorbing and releasing metal ions are a positive electrode and a negative electrode, and
the negative electrode contains a carbonaceous material or a silicon-containing material.

[A10] The energy device according to [A8] or [A9], wherein
the plural electrodes capable of absorbing and releasing metal ions are a positive electrode and a negative electrode, and
the positive electrode contains a transition metal oxide.

Advantageous Effects of Invention

According to the nonaqueous electrolyte solution of the first embodiment of the present invention, an energy device that has a low resistance and excellent discharge performance can be provided.

Further, according to the second embodiment of the present invention, a nonaqueous electrolyte solution that can realize an energy device such as a nonaqueous electrolyte secondary battery, in which the capacity retention rate, battery swelling and metal elution during cycle operation and high-temperature storage are greatly improved, can be provided. Moreover, according to a preferred mode of the second embodiment of the present invention, a nonaqueous electrolyte solution that can realize an energy device which not only exhibits excellent input-output characteristics, impedance characteristics, charge-discharge rate characteristics and the like but also has excellent cycle characteristics, high-temperature storage characteristics, continuous charging characteristics, safety and the like can be provided. Furthermore, an energy device using this nonaqueous electrolyte solution can be provided.

An electrochemical reaction of a nonaqueous electrolyte solution on an electrode surface is determined by a variety of factors, such as the redox stability of a compound itself, the concentration and the diffusion coefficient of a compound on the electrode surface, and the stability of the reaction product. When different functional groups are introduced to a single molecule, the above-described electrochemical reactivity is modified as compared to a case where independent compounds each have only one of the functional groups. By appropriately designing the functional groups to be introduced to the single molecule, a subsequent side reaction can be inhibited, so that the battery durability can be improved and swelling and metal elution can be controlled. In the present invention, it is believed that introduction of a coating film stabilization effect of a carbonate ester structure to a cyclic ether compound enables to compensate the disadvantages of a cyclic ether structure while taking advantage of the cyclic ether structure. The validity of a molecular design based on this notion is evident from the below-described results that the amount of metal elution was markedly lower in Examples A8 and A9, where a compound containing a carbonate ester structure and an ether structure in one molecule was used, than in Comparative Example A3 where a carbonate ester solvent and a crown ether additive were separately introduced.

DESCRIPTION OF EMBODIMENTS

Modes for carrying out the present invention will now be described in detail. The below-described modes are merely examples (representative examples) of the embodiments of the present invention, and the present invention is not restricted thereto. Further, modifications can be arbitrarily made to carry out the present invention, without departing from the gist of the present invention.

1. Nonaqueous Electrolyte Solution of First Embodiment

[1. Nonaqueous Electrolyte Solution]
The first object of the present invention is achieved by the first embodiment.
The nonaqueous electrolyte solution according to the first embodiment of the present invention contains a compound represented by the above-described Formula (1). The nonaqueous electrolyte solution is obtained by dissolving an electrolyte in a nonaqueous solvent; therefore, the electrolyte, the nonaqueous solvent, and the compound represented by Formula (1) are described below in the order mentioned.

<1-1. Electrolyte>

The electrolyte used in the nonaqueous electrolyte solution of the present embodiment is not particularly restricted, and any electrolyte can be employed in accordance with the intended properties of an energy device.

Specific examples of the electrolyte include inorganic lithium salts, such as $LiClO_4$, $LiAsF_6$, $LiPF_6$, $LiBF_4$, and $LiAlF_4$;

fluorine-containing organic lithium salts, such as $LiCF_3SO_3$, $LiN(CF_3SO_2)_2$, $LiN(C_2F_5SO_2)_2$, $LiN(CF_3SO_2)(C_2F_5SO_2)$, $LiN(CF_3SO_2)(C_3F_7SO_2)$, lithium cyclic 1,2-ethane disulfonylimide, lithium cyclic 1,3-propane disulfonylimide, lithium cyclic 1,2-perfluoroethane disulfonylimide, lithium cyclic 1,3-perfluoropropane disulfonylimide, lithium cyclic 1,4-perfluorobutane disulfonylimide, $LiC(CF_3SO_2)_3$, $LiPF_4(CF_3)_2$, $LiPF_4(C_2F_5)_2$, $LiPF_4(CF_3SO_2)_2$, $LiPF_4(C_2F_5SO_2)_2$, $LiBF_3(CF_3)$, $LiBF_3(C_2F_5)$, $LiBF_2(CF_3)_2$, $LiBF_2(C_2F_5)_2$, $LiBF_2(CF_3SO_2)_2$, and $LiBF_2(C_2F_5SO_2)_2$; and sodium salts and potassium salts, such as $KPF_6$, $NaPF_6$, $NaBF_4$, and $CF_3SO_3Na$.

Thereamong, lithium salts are preferred; $LiPF_6$, $LiBF_4$, $LiCF_3SO_3$, $LiN(CF_3SO_2)_2$, $LiN(C_2F_5SO_2)_2$, and lithium cyclic 1,2-perfluoroethane disulfonylimide are more preferred; $LiPF_6$, $LiBF_4$, $LiCF_3SO_3$, and $LiN(CF_3SO_2)_2$ are still more preferred; and $LiPF_6$ is particularly preferred.

Further, the nonaqueous electrolyte solution of the present embodiment preferably contains a hexafluorophosphate as the electrolyte. A hexafluorophosphate is preferred since its hexafluorophosphate anion is electrochemically stable, and this can improve the charge-discharge efficiency of an energy device obtained using the nonaqueous electrolyte solution of the present embodiment. In addition, the hexafluorophosphate can greatly increase the salt dissociation degree, so that the concentration of ions serving as charge carriers in the electrolyte solution can be increased.

Any of the above-described electrolytes may be used singly, or two or more thereof may be used in any combination at any ratio. Among the above-described electrolytes, it is preferred to use a combination of two kinds of inorganic lithium salts or a combination of an inorganic lithium salt and a fluorine-containing organic lithium salt since gas generation during continuous charging or deterioration during high-temperature storage of an energy device are thereby effectively inhibited.

The use of a combination of $LiPF_6$ and $LiBF_4$, or the use of a combination of an inorganic lithium salt, such as $LiPF_6$ or $LiBF_4$, and a fluorine-containing organic lithium salt, such as $LiCF_3SO_3$, $LiN(CF_3SO_2)_2$ or $LiN(C_2F_5SO_2)_2$, is particularly preferred.

When $LiPF_6$ and $LiBF_4$ are used in combination, the ratio of $LiBF_4$ with respect to all electrolytes is preferably 0.001% by mass to 20% by mass. When the ratio of $LiBF_4$ is in this range, an increase in the resistance of the nonaqueous electrolyte solution due to the low dissociation degree of $LiBF_4$ can be inhibited.

Meanwhile, when an inorganic lithium salt, such as $LiPF_6$ or $LiBF_4$, and a fluorine-containing organic lithium salt, such as $LiCF_3SO_3$, $LiN(CF_3SO_2)_2$ or $LiN(C_2F_5SO_2)_2$, are used in combination, the ratio of the inorganic lithium salt with respect to all electrolytes is preferably 70% by mass to 99.9% by mass. When the ratio of the inorganic lithium salt is in this range, an increase in the resistance of the non-aqueous electrolyte solution, which is caused by a reduction in the proportion of the nonaqueous solvent in the whole nonaqueous electrolyte solution due to an excessively high ratio of the fluorine-containing organic lithium salt generally having a higher molecular weight than a hexafluorophosphate, can be inhibited.

In the composition of the nonaqueous electrolyte solution of the present embodiment in an energy device that is ultimately produced, the electrolyte(s) such as a lithium salt may have any concentration as long as the effects of the present embodiment are not markedly impaired; however, the concentration is preferably 0.5 mol/L to 3 mol/L. When the electrolyte concentration is equal to or higher than the lower limit, the nonaqueous electrolyte solution is likely to attain a sufficient ionic conductivity, while when the electrolyte concentration is equal to or lower than the upper limit, an excessive increase in the viscosity can be avoided. Accordingly, a good ionic conductivity and good energy device performance are likely to be ensured. The concentration of the electrolyte(s) such as a lithium salt is in a range of more preferably 0.6 mol/L or higher, still more preferably 0.8 mol/L or higher, but more preferably 2 mol/L or lower, still more preferably 1.5 mol/L or lower.

<1-2. Nonaqueous Solvent>

The nonaqueous solvent contained in the nonaqueous electrolyte solution of the present embodiment is not particularly restricted as long as it does not adversely affect the battery characteristics when the battery is used in an energy device; however, the nonaqueous solvent is preferably at least one of the below-described nonaqueous solvents.

The nonaqueous solvent may be, for example, an open-chain carbonate, a cyclic carbonate, an open-chain carboxylic acid ester, a cyclic carboxylic acid ester, an open-chain ether, a cyclic ether, a phosphorus-containing organic solvent, a sulfur-containing organic solvent, or a boron-containing organic solvent.

The type of the open-chain carbonate is not particularly restricted, and examples thereof include dialkyl carbonates. In the dialkyl carbonates, the alkyl groups constituting the respective dialkyl carbonates each have preferably 1 to 5 carbon atoms, more preferably 1 to 4 carbon atoms, particularly preferably 1 to 3 carbon atoms. Specifically, preferred examples of such dialkyl carbonates include dimethyl carbonate, ethyl methyl carbonate, diethyl carbonate, methyl-n-propyl carbonate, ethyl-n-propyl carbonate, and di-n-propyl carbonate.

Thereamong, dimethyl carbonate, ethyl methyl carbonate and diethyl carbonate are more preferred since they have good industrial availability and exhibit favorable properties in an energy device.

Further, a fluorine atom-containing open-chain carbonate (hereinafter, may be simply referred to as "fluorinated open-chain carbonate") can be preferably used as well. The number of fluorine atoms in the fluorinated open-chain carbonate is not particularly restricted as long as it is one or more; however, it is usually 6 or less, preferably 4 or less, more preferably 3 or less. When the fluorinated open-chain carbonate has plural fluorine atoms, the fluorine atoms may be bound to the same carbon, or may be bound to different carbons. Examples of the fluorinated open-chain carbonate include fluorinated dimethyl carbonates, fluorinated ethyl methyl carbonates, and fluorinated diethyl carbonates.

Examples of the fluorinated dimethyl carbonates include fluoromethyl methyl carbonate, difluoromethyl methyl carbonate, trifluoromethyl methyl carbonate, bis(fluoromethyl) carbonate, bis(difluoro)methyl carbonate, and bis(trifluoromethyl)carbonate.

Examples of the fluorinated ethyl methyl carbonates include 2-fluoroethyl methyl carbonate, ethyl fluoromethyl carbonate, 2,2-difluoroethyl methyl carbonate, 2-fluoroethyl fluoromethyl carbonate, ethyl difluoromethyl carbonate, 2,2,2-trifluoroethyl methyl carbonate, 2,2-difluoroethyl fluoromethyl carbonate, 2-fluoroethyl difluoromethyl carbonate, and ethyl trifluoromethyl carbonate.

Examples of the fluorinated diethyl carbonates include ethyl-(2-fluoroethyl)carbonate, ethyl-(2,2-difluoroethyl)carbonate, bis(2-fluoroethyl)carbonate, ethyl-(2,2,2-trifluoroethyl)carbonate, 2,2-difluoroethyl-2'-fluoroethyl carbonate, bis(2,2-difluoroethyl)carbonate, 2,2,2-trifluoroethyl-2'-fluoroethyl carbonate, 2,2,2-trifluoroethyl-2',2'-difluoroethyl carbonate, and bis(2,2,2-trifluoroethyl)carbonate.

These fluorinated open-chain carbonates effectively function not only as nonaqueous solvents but also as the additives described below in <1-4. Additives>. When a fluorinated open-chain carbonate is used as both a solvent and an additive, there is no clear limit on the amount thereof to be incorporated, and any of the amounts described in the present specification with regard to the nonaqueous solvent and additives can be directly applied.

The type of the above-described cyclic carbonate is not particularly restricted, and examples thereof include alkylene carbonates. In the alkylene carbonates, the number of carbon atoms of the alkylene group constituting each alkylene carbonate is preferably 2 to 6, particularly preferably 2 to 4. Specific examples of such cyclic carbonates include ethylene carbonate, propylene carbonate, and butylene carbonate (2-ethylethylene carbonate, cis- and trans-2,3-dimethylethylene carbonate).

Thereamong, as the cyclic carbonate, ethylene carbonate and propylene carbonate are preferred, and ethylene carbonate is particularly preferred, since these carbonates have a high dielectric constant and can thus reduce the resistance of a nonaqueous electrolyte energy device.

The type of the above-described open-chain carboxylic acid ester is also not particularly restricted, and examples thereof include methyl acetate, ethyl acetate, n-propyl acetate, i-propyl acetate, n-butyl acetate, i-butyl acetate, t-butyl acetate, methyl propionate, ethyl propionate, n-propyl propionate, i-propyl propionate, n-butyl propionate, i-butyl propionate, t-butyl propionate, methyl butyrate, and ethyl butyrate.

Thereamong, methyl acetate, ethyl acetate, methyl propionate, ethyl propionate, methyl butyrate, and ethyl butyrate are preferred since they have good industrial availability and exhibit favorable properties in an energy device.

The type of the above-described cyclic carboxylic acid ester is also not particularly restricted, and examples thereof include γ-butyrolactone, γ-valerolactone, and δ-valerolactone.

Thereamong, γ-butyrolactone is preferred since it has good industrial availability and exhibit favorable properties in an energy device.

The type of the above-described open-chain ether is also not particularly restricted, and examples thereof include dimethoxymethane, dimethoxyethane, diethoxymethane, diethoxyethane, ethoxymethoxymethane, and ethoxymethoxyethane.

Thereamong, dimethoxyethane and diethoxyethane are preferred since they have good industrial availability and exhibit favorable properties in an energy device.

The type of the above-described cyclic ether is also not particularly restricted, and examples thereof include tetrahydrofuran, 2-methyltetrahydrofuran, and tetrahydropyran.

The type of the above-described phosphorus-containing organic solvent is also not particularly restricted, and examples thereof include trimethyl phosphate, triethyl phosphate, triphenyl phosphate, tris(2,2,2-trifluoroethyl) phosphate, trimethyl phosphite, triethyl phosphite, triphenyl phosphite, trimethyl phosphine oxide, triethyl phosphine oxide, and triphenyl phosphine oxide.

The type of the above-described sulfur-containing organic solvent is also not particularly restricted, and examples thereof include ethylene sulfite, 1,3-propane sultone, 1,4-butane sultone, methyl methanesulfonate, ethyl methanesulfonate, busulfan, sulfolane, sulfolene, dimethyl sulfone, ethyl methyl sulfone, diphenyl sulfone, methyl phenyl sulfone, dibutyl disulfide, dicyclohexyl disulfide, tetramethyl thiuram monosulfide, N,N-dimethylmethane sulfonamide, and N,N-diethylmethane sulfonamide.

The type of the above-described boron-containing organic solvent is also not particularly restricted, and examples thereof include boroxines, such as 2,4,6-trimethyl boroxine and 2,4,6-triethyl boroxine.

Among the above-exemplified nonaqueous solvents, open-chain carbonates, cyclic carbonates, open-chain carboxylic acid esters, and cyclic carboxylic acid esters are preferred because of their good properties in an energy device and, thereamong, ethylene carbonate, propylene carbonate, dimethyl carbonate, ethyl methyl carbonate, diethyl carbonate, 2,2,2-trifluoroethylmethyl carbonate, bis(2,2,2-trifluoroethyl)carbonate, methyl acetate, ethyl acetate, methyl propionate, ethyl propionate, methyl butyrate, ethyl butyrate and γ-butyrolactone are more preferably; and ethylene carbonate, propylene carbonate, dimethyl carbonate, ethyl methyl carbonate, diethyl carbonate, 2,2,2-trifluoroethyl methyl carbonate, methyl acetate, ethyl acetate, methyl propionate, ethyl propionate and methyl butyrate are still more preferred.

These nonaqueous solvents may be used singly, or in combination of two or more thereof, and it is preferred to use two or more of the nonaqueous solvents in combination. For example, it is preferred to use a high-dielectric-constant solvent such as a cyclic carbonate in combination with a low-viscosity solvent, such as an open-chain carbonate or an open-chain ester.

One preferred combination of nonaqueous solvents is a combination mainly composed of a cyclic carbonate and an open-chain carbonate. In this combination, the total ratio of the cyclic carbonate and the open-chain carbonate with respect to all nonaqueous solvents is preferably 80% by volume or higher, more preferably 85% by volume or higher, particularly preferably 90% by volume or higher, and the volume ratio of the cyclic carbonate and the open-chain carbonate (total volume of cyclic carbonate:total volume of open-chain carbonate) is preferably 0.5:9.5 to 7:3, more preferably 1:9 to 5:5, still more preferably 1.5:8.5 to 4:6, particularly preferably 2:8 to 3.5:6.5. In an energy device produced using a combination of these nonaqueous solvents, a good balance is attained between the cycle characteristics and the high-temperature storage characteristics (particularly the residual capacity after high-temperature storage and the high-load discharge capacity), which is preferred.

Examples of preferred combinations of a cyclic carbonate and an open-chain carbonate include combinations of ethylene carbonate and an open-chain carbonate(s), such as a combination of ethylene carbonate and dimethyl carbonate, a combination of ethylene carbonate and diethyl carbonate, a combination of ethylene carbonate and ethyl methyl carbonate, a combination of ethylene carbonate, dimethyl carbonate and diethyl carbonate, a combination of ethylene carbonate, dimethyl carbonate and ethyl methyl carbonate, a combination of ethylene carbonate, diethyl carbonate and ethyl methyl carbonate, and a combination of ethylene carbonate, dimethyl carbonate, diethyl carbonate and ethyl methyl carbonate.

A combination in which propylene carbonate is added to any of the above-described combinations of ethylene carbonate and an open-chain carbonate(s) is also preferred. When propylene carbonate is incorporated, as described above, the volume ratio of ethylene carbonate and propylene carbonate is required to be 99:1 to 40:60, and it is preferably 95:5 to 45:55, more preferably 85:15 to 50:50. Further, the amount of propylene carbonate with respect to all nonaqueous solvents is preferably 0.1% by volume to 10% by volume since this enables to attain superior discharge load characteristics while maintaining the properties attributed to the combination of ethylene carbonate and an open-chain carbonate. The amount of propylene carbonate with respect to all nonaqueous solvents is more preferably 1% by volume, particularly preferably 2% by volume or greater, but more preferably 8% by volume or less, particularly preferably 5% by volume or less.

Among these combinations, ones containing an asymmetric open-chain carbonate as an open-chain carbonate are more preferred, and those containing ethylene carbonate, dimethyl carbonate and ethyl methyl carbonate, those containing ethylene carbonate, diethyl carbonate and ethyl methyl carbonate, those containing ethylene carbonate, dimethyl carbonate, diethyl carbonate and ethyl methyl carbonate, and those further containing propylene carbonate in addition to any of the above-described combinations of carbonates are particularly preferred from the standpoint of attaining a good balance between the cycle characteristics and the discharge load characteristics in an energy device. Especially, ones in which the asymmetric open-chain carbonate is ethyl methyl carbonate, as well as ones in which the alkyl groups constituting the respective dialkyl carbonates have 1 to 2 carbon atoms, are preferred.

In the present embodiment, other examples of preferred nonaqueous solvents include solvents containing an open-chain carboxylic acid ester. Particularly, mixed solvents of the above-described cyclic carbonate and open-chain carbonate which further contains an open-chain carboxylic acid ester are preferred from the standpoint of improving the discharge load characteristics of an energy device and, in this case, the open-chain carboxylic acid ester is particularly preferably methyl acetate, ethyl acetate, methyl propionate, ethyl propionate, methyl butyrate, or ethyl butyrate. The volume of the open-chain carboxylic acid ester with respect to the nonaqueous solvents is preferably 5% by volume or greater, more preferably 8% by volume or greater, particularly preferably 10% by volume or greater, but preferably 50% by volume or less, more preferably 35% by volume or less, particularly preferably 30% by volume or less, especially preferably 25% by volume or less.

<1-3. Compound Represented by Formula (1)>

The nonaqueous electrolyte solution of the present embodiment contains a compound represented by the following Formula (1) (hereinafter, may be referred to as "specific ether") as an indispensable component. In the nonaqueous electrolyte solution of the present embodiment, the specific ether may be used singly, or two or more thereof may be used in any combination at any ratio.

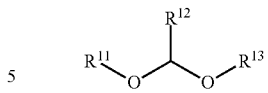

(1)

In Formula (1), $R^{11}$, $R^{12}$ and $R^{13}$ each independently represent an organic group having 1 to 3 carbon atoms; and $R^{11}$ and $R^{12}$, $R^{11}$ and $R^{13}$, or $R^{12}$ and $R^{13}$ are optionally bound with each other to form a 5-membered ring or a 6-membered ring, with a proviso that a total number of carbon atoms of $R^{11}$, $R^{12}$ and $R^{13}$ is 7 or less.

In the present embodiment, deterioration of the characteristics of an energy device can be kept small by using the nonaqueous electrolyte solution containing the specific ether. The action and principle of this effect are not clear; however, the present inventors presume as follows. However, the present embodiment should not be restricted to the below-described action and principle.

The specific ether of the present embodiment is characterized by having a structure which contains two ether oxygen atoms with only one carbon atom existing therebetween, and the carbon atom has a substituent.

A transition metal oxide is a material that is often used in an electrode of an energy device, and the surface of the transition metal oxide has a partial structure such as —O-M-O— (wherein, M represents a transition metal atom, and O represents an oxygen atom), i.e., a partial structure in which a transition metal atom is exposed, and this is presumed to be where the reactivity with an electrolyte solution is the highest.

It is believed that the specific ether of the present embodiment, which has the above-described characteristic structure, can act in such a manner to sandwich the exposed transition metal atom with its lone electron pair of two oxygen atoms and thereby effectively protect active sites on the electrode surface.

At the same time, the specific ether of the present embodiment has a substituent on the carbon atom between the two ether oxygen atoms; therefore, it is presumed that the above-described protective structure is not overly compact and has an appropriate compactness.

In the specific ether represented by Formula (1), $R^{11}$, $R^{12}$ and $R^{13}$ are each independently an organic group having 1 to 3 carbon atoms, preferably not more than 2 carbon atoms; however, it is preferred that $R^{11}$, $R^{12}$ and $R^{13}$ be all hydrocarbon groups. This is because it is presumed that, with the specific ether not having any functional group other than the above-described characteristic structure, the specific ether is unlikely to exert an action other than the above-described one, and the above-described action thus takes place appropriately.

Further, $R^{11}$, $R^{12}$ and $R^{13}$ are each preferably a methyl group, an ethyl group or an n-propyl group, more preferably a methyl group or an ethyl group. It is also preferred that $R^{11}$ and $R^{13}$ be bound with each other to form a 5-membered ring or a 6-membered ring and, in this case, an organic group formed by $R^{11}$ and $R^{13}$ that are bound with each other is preferably an ethylene group, a trimethylene group, a methyl ethylene group or an ethyl ethylene group, more preferably an ethylene group or a methyl ethylene group. When a ring is formed, the ring is more preferably a 5-membered ring. The total number of carbon atoms of $R^{11}$, $R^{12}$ and $R^{13}$ is 7 or less, preferably 6 or less, more preferably 5 or less. This is because such an ether makes it easier to keep the viscosity of an electrolyte solution low when the electrolyte solution is used as a nonaqueous electrolyte solution.

The total number of carbon atoms of $R^1$, $R^{12}$ and $R^{13}$ is not less than 3, preferably not less than 4. This is because such a compound itself has a limited volatility and thus reduces the risk of ignition, making the handling thereof easy.

The molecular weight of the above-described specific ether in the present embodiment is preferably not higher than 200, more preferably not higher than 150, still more preferably not higher than 130, particularly preferably not higher than 120. When the molecular weight is in this range, the specific ether has excellent solubility in the nonaqueous solvent and is thus likely to exert an excellent effect more effectively.

Preferred specific examples of the specific ether represented by Formula (1) include the followings. The following specific ethers are preferred since they have excellent solubility in the nonaqueous electrolyte solution and the productivity of the nonaqueous electrolyte solution is thus likely to be improved.

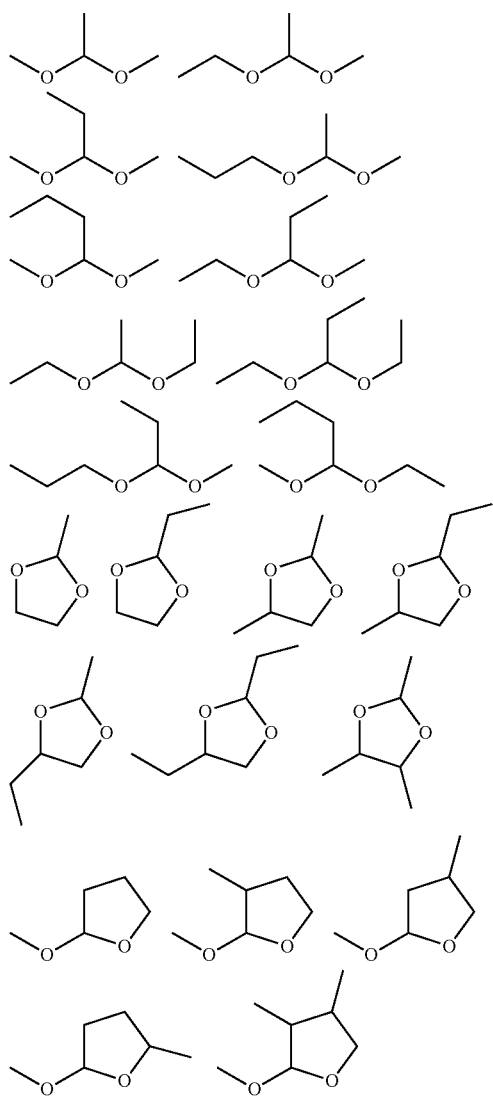

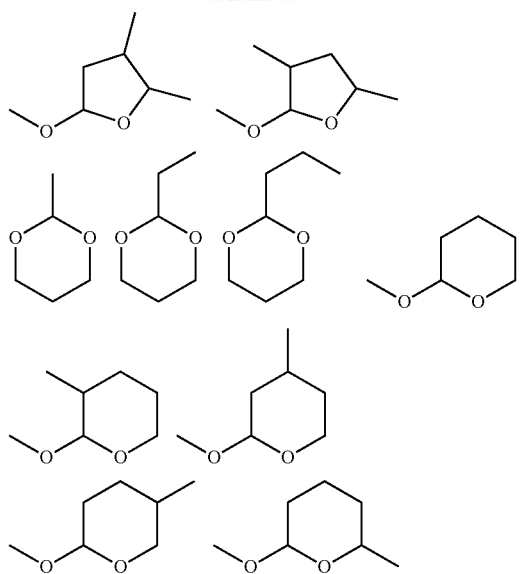

More preferred specific examples include the followings. The following specific ethers are preferred since they each have a favorable molecular size and are thus presumed to be capable of efficiently inducing a desired action.

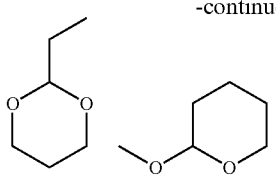

Still more preferred specific examples include the followings. The following specific ethers are preferred since they are presumed to have excellent stability in the electrolyte solution.

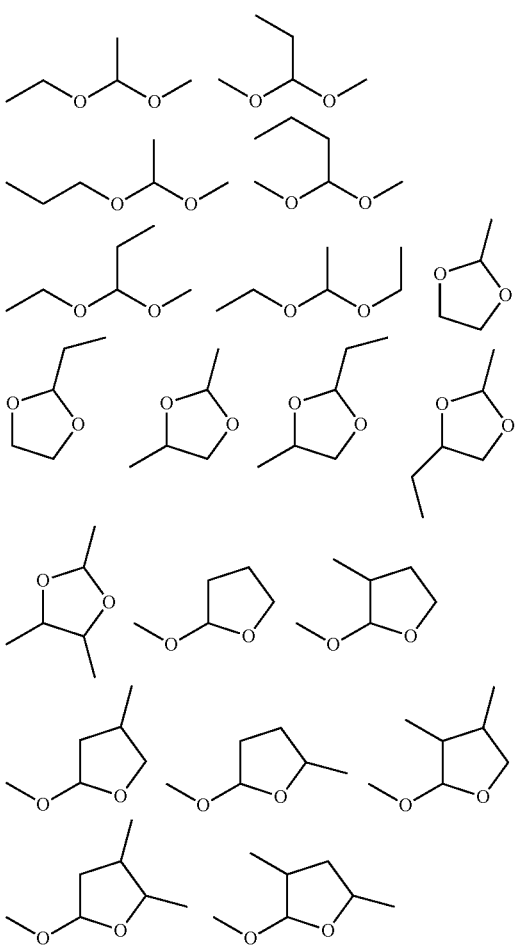

Yet still more preferred specific examples include the followings. The following specific ethers are preferred since they have a favorable steric hindrance and are thus presumed to be capable of promptly undergoing a desired reaction.

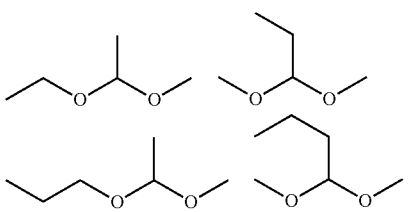

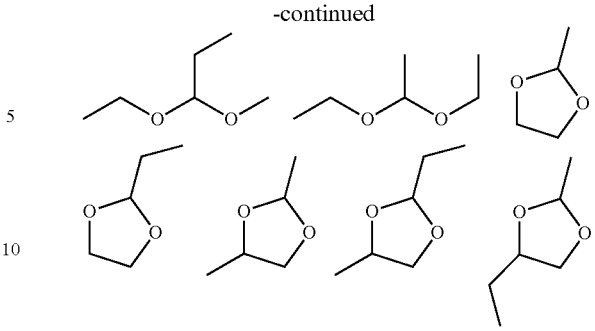

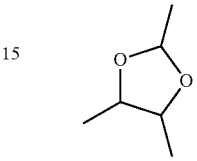

Particularly preferred specific examples include the followings. The following specific ethers are preferred since they have a low symmetry and are thus likely to be uniformly dissolved in the electrolyte solution.

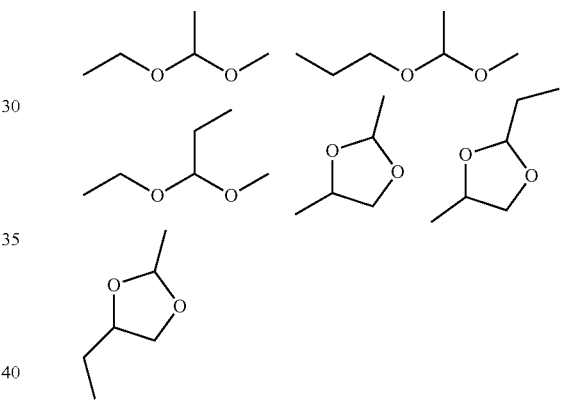

The total content of the specific ether with respect to the whole nonaqueous electrolyte solution is preferably 0.01 ppm by mass or higher, more preferably 0.02 ppm by mass or higher, still more preferably 0.03 ppm by mass or higher, particularly preferably 0.05 ppm by mass or higher. The specific ether can be partially inactivated through interaction with metal impurities contained in the nonaqueous electrolyte solution; however, as long as the total content is in the above-described range, the specific ether showing the above-described effect is likely to remain without being inactivated. Meanwhile, the total content of the specific ether is preferably 0.1% by mass or less, more preferably 0.01% by mass or less, still more preferably 50 ppm by mass or less, particularly preferably 10 ppm by mass or less. This is because, when the concentration of the specific ether is excessively high, the effect of the specific ether is saturated and only the cost of the nonaqueous electrolyte solution is increased.

It is noted here that a commercially available ether may be used as the specific ether and, in the case of producing the specific ether, a method thereof is not restricted, and one produced by a known method can be used.

<1-4. Additives>

The nonaqueous electrolyte solution of the present embodiment may also contain various additives within a range that does not markedly impair the effects of the present invention. As the additives, any conventionally known additives can be used. Any of such additives may be used singly, or two or more thereof may be used in any combination at any ratio.

Examples of the additives include overcharge inhibitors, and auxiliary agents for improving the capacity retention and cycle characteristics after high-temperature storage of an energy device. Thereamong, the nonaqueous electrolyte solution preferably contains, as an auxiliary agent for improving the capacity retention characteristics after high-temperature storage and inhibiting an increase in the resistance, at least one compound selected from the group consisting of a fluorine atom-containing cyclic carbonate, a carbon-carbon unsaturated bond-containing cyclic carbonate, a difluorophosphate salt, a fluorosulfate salt, an isocyanate group-containing compound, a cyano group-containing compound, a cyclic sulfonate ester, and a dicarboxylic acid complex salt (hereinafter, these additives may be simply referred to as "specific additives"). The specific additives and other additives are separately described below.

<1-4-1. Specific Additives>

All of the specific additives are believed to react with the specific ether reduced on a reducing electrode among plural electrodes of an energy device and to thereby concertedly form a film-like structure suitable for electrode reaction. The action and principle thereof are not restricted to the below-described ones; however, the present inventors presume as follows. For (i) a fluorine atom-containing cyclic carbonate, (ii) a carbon-carbon unsaturated bond-containing cyclic carbonate, (iii) a difluorophosphate salt, (iv) a fluorosulfate salt, (v) an isocyanate group-containing compound, (vi) a cyano group-containing compound, (vii) a cyclic sulfonate ester and (viii) a dicarboxylic acid complex salt, presumed reaction mechanisms with a nucleophilic species $Nu^-$ formed on the reducing electrode surface by reduction of the specific ether are shown below.

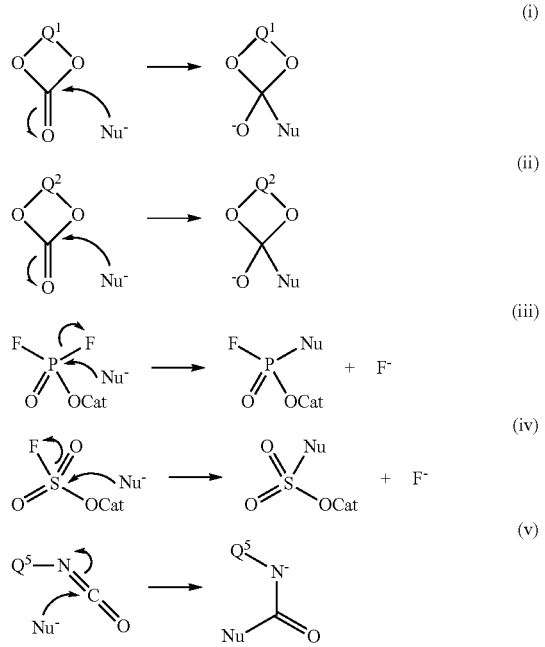

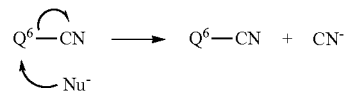

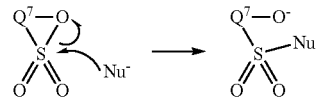

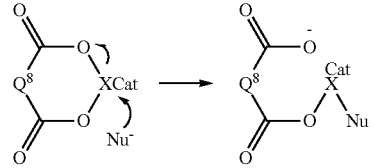

In the above reaction formulae, Cat represents a cation constituting the respective salt; $Q^1$ represents a fluorine-containing divalent organic group; $Q^2$ represents a divalent organic group containing a carbon-carbon unsaturated bond; $Q^5$ and $Q^6$ each represent a monovalent organic group; $Q^7$ represents a divalent organic group; $Q^8$ represents a single bond or a divalent organic group; and X represents a divalent organic group containing a complex central element.

All of the specific additives contain a nucleophilic attack acceptor site as shown in the reaction formulae and are presumed to concertedly form a film-like structure that favorably supports the electrode reaction, starting with the respective reactions shown above.

The molecular weight of each specific additive is not particularly restricted, and each specific additive may have any molecular weight as long as the effects of the present embodiment are not markedly impaired; however, it is preferably 50 to 250. When the molecular weight is in this range, the specific additive has good solubility in the nonaqueous electrolyte solution, so that the effect of adding the specific additive can be sufficiently exerted.

A method of producing each specific additive is also not particularly restricted, and any known method can be selected to produce each specific additive. A commercially available additive may be used as well.

In the nonaqueous electrolyte solution of the present embodiment, any of the specific additives may be incorporated singly, or two or more thereof may be incorporated in any combination at any ratio.

<1-4-1-1. Fluorine Atom-Containing Cyclic Carbonate>

Among the specific additives, the fluorine atom-containing cyclic carbonate (hereinafter, may be simply referred to as "fluorinated carbonate") is not particularly restricted as long as it contains a fluorine atom, and any fluorinated carbonate can be used.

The number of fluorine atoms contained in the fluorinated carbonate is also not particularly restricted as long as it is one or more, and it is particularly preferably two or less.

Examples of the fluorinated carbonate include fluoroethylene carbonate and derivatives thereof.

Specific examples of the fluoroethylene carbonate and derivatives thereof include fluoroethylene carbonate, 4,4-difluoroethylene carbonate, 4,5-difluoroethylene carbonate, 4-fluoro-4-methylethylene carbonate, 4,5-difluoro-4-methyl ethylene carbonate, 4-fluoro-5-methylethylene carbonate, 4,4-difluoro-5-methylethylene carbonate, 4-(fluoromethyl)-ethylene carbonate, 4-(difluoromethyl)-ethylene carbonate, 4-(trifluoromethyl)-ethylene carbonate, 4-(fluoromethyl)-4- fluoroethylene carbonate, 4-(fluoromethyl)-5-fluoroethylene carbonate, 4-fluoro-4,5-dimethylethylene carbonate, 4,5-difluoro-4,5-dimethylethylene carbonate, and 4,4-difluoro-5,5-dimethylethylene carbonate.

Among these fluorinated carbonates, fluoroethylene carbonate, 4-(fluoromethyl)-ethylene carbonate, 4,4-difluoroethylene carbonate and 4,5-difluoroethylene carbonate are preferred and, thereamong, fluoroethylene carbonate can contribute to the formation of a stable film-like structure and is thus most preferably used.

The content of the fluorinated carbonate is not particularly restricted and may be set arbitrarily as long as the effects of the present invention are not markedly impaired; however, it is preferably 0.001% by mass to 10.0% by mass with respect to the amount of the nonaqueous electrolyte solution of the present embodiment.

When the content of the fluorinated carbonate is not lower than this lower limit, the fluorinated carbonate can bring about a sufficient cycle characteristics-improving effect in an energy device. Meanwhile, when the content of the fluorinated carbonate is not higher than the upper limit, an increase in the energy device production cost can be avoided. The content of the fluorinated carbonate is more preferably 0.01% by mass or higher, still more preferably 0.1% by mass or higher, particularly preferably 0.2% by mass or higher, but more preferably 8.0% by mass or less, particularly preferably 6.0% by mass or less.

It is noted here that the fluorinated carbonate effectively functions not only as an additive but also as the solvent described above in the section 1-2. When the fluorinated carbonate is used as both a solvent and an additive, there is no clear limit on the amount thereof to be incorporated, and any of the above-described amounts can be directly applied.

<1-4-1-2. Carbon-Carbon Unsaturated Bond-Containing Cyclic Carbonate>

Among the specific additives, the carbon-carbon unsaturated bond-containing cyclic carbonate (hereinafter, may be simply referred to as "unsaturated carbonate") is not particularly restricted as long as it is a carbonate that has a carbon-carbon unsaturated bond, such as a carbon-carbon double bond or a carbon-carbon triple bond, and any unsaturated carbonate can be used.

The unsaturated carbonate may be, for example, a vinylene carbonate, or an ethylene carbonate substituted with a substituent having a carbon-carbon unsaturated bond.

Specific examples of the vinylene carbonate include vinylene carbonate, methylvinylene carbonate, and 4,5-dimethylvinylene carbonate.

Specific examples of the ethylene carbonate substituted with a substituent having a carbon-carbon unsaturated bond include vinylethylene carbonate, 4,5-divinylethylene carbonate, ethynylethylene carbonate, and propargylethylene carbonate.

Thereamong, vinylene carbonate, vinylethylene carbonate and ethynylethylene carbonate are preferred and, particularly vinylene carbonate can contribute to the formation of a stable film-like structure and is thus more preferably used.

The content of the unsaturated carbonate is not particularly restricted and may be set arbitrarily as long as the effects of the present invention are not markedly impaired; however, it is preferably 0.001% by mass to 5.0% by mass with respect to the amount of the nonaqueous electrolyte solution of the present embodiment.

When the content of the unsaturated carbonate is not lower than this lower limit, the unsaturated carbonate can bring about a sufficient cycle characteristics-improving effect in an energy device. Meanwhile, when the content of the unsaturated carbonate is not higher than the upper limit, an increase in the initial resistance of an energy device can be avoided. The content of the unsaturated carbonate is more preferably 0.01% by mass or higher, still more preferably 0.1% by mass or higher, particularly preferably 0.2% by mass or higher, but more preferably 4.0% by mass or less, still more preferably 3.0% by mass or less, particularly preferably 2.0% by mass or less.

<1-4-1-3. Difluorophosphate Salt>

Among the specific additives, the difluorophosphate salt is not particularly restricted as long as it is a salt having a difluorophosphate anion as a constituent, and any difluorophosphate salt can be used.

Examples of the difluorophosphate salt include lithium difluorophosphate, sodium difluorophosphate, potassium difluorophosphate, and ammonium difluorophosphate.

Thereamong, lithium difluorophosphate is preferred and more suitably used since it can contribute to the formation of a stable film-like structure.

The content of the difluorophosphate salt is not particularly restricted and may be set arbitrarily as long as the effects of the present invention are not markedly impaired; however, it is preferably 0.001% by mass to 2.0% by mass with respect to the amount of the nonaqueous electrolyte solution of the present embodiment.

When the content of the difluorophosphate salt is not lower than this lower limit, the difluorophosphate salt can bring about a sufficient cycle characteristics-improving effect in a nonaqueous electrolyte secondary battery. Meanwhile, when the content of the difluorophosphate salt is not higher than the upper limit, an increase in the production cost of a nonaqueous electrolyte secondary battery can be avoided. The content of the difluorophosphate salt is more preferably 0.01% by mass or higher, still more preferably 0.1% by mass or higher, particularly preferably 0.2% by mass or higher, but more preferably 1.5% by mass or less, still more preferably 1.2% by mass or less, particularly preferably 1.1% by mass or less.

<1-4-1-4. Fluorosulfate Salt>

Among the specific additives, the fluorosulfate salt is not particularly restricted as long as it is a salt having a fluorosulfate anion as a constituent, and any fluorophosphate can be used.

Examples of the fluorosulfate include lithium fluorosulfate, sodium fluorosulfate, potassium fluorosulfate, and ammonium fluorosulfate.

Thereamong, lithium fluorosulfate is preferred and more suitably used since it can contribute to the formation of a stable film-like structure.

The content of the fluorosulfate salt is not particularly restricted and may be set arbitrarily as long as the effects of the present invention are not markedly impaired; however, it is preferably 0.001% by mass to 4.0% by mass with respect to the amount of the nonaqueous electrolyte solution of the present embodiment.

When the content of the fluorosulfate salt is not lower than this lower limit, the fluorosulfate salt can bring about a sufficient cycle characteristics-improving effect in a nonaqueous electrolyte secondary battery. Meanwhile, when the content of the fluorosulfate salt is not higher than the upper limit, not only an increase in the production cost of a nonaqueous electrolyte secondary battery can be avoided, but also deterioration of the performance due to corrosion of aluminum often used in positive electrode current collectors or metallic cans often used as outer casings can be avoided. The content of the fluorosulfate salt is more preferably 0.01% by mass or higher, still more preferably 0.1% by mass or higher, particularly preferably 0.2% by mass or higher, but more preferably 3.0% by mass or less, still more preferably 2.5% by mass or less, particularly preferably 2.0% by mass or less.

<1-4-1-5. Isocyanate Group-Containing Compound>

Among the specific additives, the isocyanate group-containing compound (hereinafter, may be simply referred to as "isocyanate") is not particularly restricted, and any isocyanate can be used.

The isocyanate may be, for example, a monoisocyanate, a diisocyanate, or a triisocyanate.

Specific examples of the monoisocyanate include isocyanate, methyl isocyanate, ethyl isocyanate, propyl isocyanate, isopropyl isocyanate, butyl isocyanate, t-butyl isocyanate, pentyl isocyanate, hexyl isocyanate, 1-isocyanatoheptane, 1-isocyanatooctane, 1-isocyanatononane, 1-isocyanatodecane, cyclohexyl isocyanate, methoxycarbonyl isocyanate, ethoxycarbonyl isocyanate, propoxycarbonyl isocyanate, butoxycarbonyl isocyanate, methoxysulfonyl isocyanate, ethoxysulfonyl isocyanate, propoxysulfonyl isocyanate, butoxysulfonyl isocyanate, and fluorosulfonyl isocyanate.

Specific examples of the diisocyanate include 1,4-diisocyanatobutane, 1,5-diisocyanatopentane, 1,6-diisocyanatohexane, 1,7-diisocyanatoheptane, 1,8-diisocyanatooctane, 1,9-diisocyanatononane, 1,10-diisocyanatodecane, 1,3-diisocyanatopropene, 1,4-diisocyanato-2-butene, 1,4-diisocyanato-2-fluorobutane, 1,4-diisocyanato-2,3-difluorobutane, 1,5-diisocyanato-2-pentene, 1,5-diisocyanato-2-methylpentane, 1,6-diisocyanato-2-hexene, 1,6-diisocyanato-3-hexene, 1,6-diisocyanato-3-fluorohexane, 1,6-diisocyanato-3,4-difluorohexane, toluene diisocyanate, xylene diisocyanate, tolylene diisocyanate, 1,2-bis(isocyanatomethyl)cyclohexane, 1,3-bis(isocyanatomethyl)cyclohexane, 1,4-bis(isocyanatomethyl)cyclohexane, 1,2-diisocyanatocyclohexane, 1,3-diisocyanatocyclohexane, 1,4-diisocyanatocyclohexane, dicyclohexylmethane-1,1'-diisocyanate, dicyclohexylmethane-2,2'-diisocyanate, dicyclohexylmethane-3,3'-diisocyanate, dicyclohexylmethane-4,4'-diisocyanate, isophorone diisocyanate, bicyclo[2.2.1]heptane 2,5-diylbis(methyl isocyanate), bicyclo[2.2.1]heptane 2,6-diylbis(methyl isocyanate), 2,4,4-trimethylhexamethylene diisocyanate, and 2,2,4-trimethylhexamethyl ene diisocyanate.

Specific examples of the triisocyanate include 1,6,11-triisocyanatoundecane, 4-isocyanatomethyl-1,8-octamethylene diisocyanate, 1,3,5-triisocyanatemethylbenzene, 1,3,5-tris(6-isocyanatohexa-1-yl)-1,3,5-triazine-2,4,6(1H,3H,5H)-trione, and 4-(i socyanatomethyl)octamethylene diisocyanate.

Thereamong, 1,6-diisocyanatohexane, 1,3-bis(isocyanatomethyl)cyclohexane, 1,3,5-tris(6-isocyanatohexa-1-yl)-1,3,5-triazine-2,4,6(1H,3H,5H)-trione, 2,4,4-trimethylhexamethylene diisocyanate, and 2,2,4-trimethylhexamethylene diisocyanate are preferred since they are easy to obtain industrially and the production cost of the electrolyte solution is thus kept low, and these isocyanates can be more suitably used from the technical standpoint as well since they can contribute to the formation of a stable film-like structure.

The content of the isocyanate is not particularly restricted and may be set arbitrarily as long as the effects of the present invention are not markedly impaired; however, it is preferably 0.001% by mass to 1.0% by mass with respect to the amount of the nonaqueous electrolyte solution of the present embodiment.

When the content of the isocyanate is not lower than this lower limit, the isocyanate can bring about a sufficient cycle characteristics-improving effect in a nonaqueous electrolyte secondary battery. Meanwhile, when the content of the isocyanate is not higher than the upper limit, an increase in the initial resistance of a nonaqueous electrolyte secondary battery is be avoided. The content of the isocyanate is more preferably 0.01% by mass or higher, still more preferably 0.1% by mass or higher, particularly preferably 0.2% by mass or higher, but more preferably 0.8% by mass or less, still more preferably 0.7% by mass or less, particularly preferably 0.6% by mass or less.

<1-4-1-6. Cyano Group-Containing Compound>

Among the specific additives, the cyano group-containing compound (hereinafter, may be simply referred to as "nitrile") is not particularly restricted, and any nitrile can be used.

The nitrile may be, for example, a mononitrile or a dinitrile.

Specific examples of the mononitrile include acetonitrile, propionitrile, butyronitrile, isobutyronitrile, valeronitrile, isovaleronitrile, lauronitrile, 2-methylbutyronitrile, trimethylacetonitrile, hexanenitrile, cyclopentanecarbonitrile, cyclohexanecarbonitrile, acrylonitrile, methacrylonitrile, crotononitrile, 3-methylcrotononitrile, 2-methyl-2-buteneni-trile, 2-pentenenitrile, 2-methyl-2-pentenenitrile, 3-methyl-2-pentenenitrile, 2-hexenenitrile, fluoroacetonitrile, difluoroacetonitrile, trifluoroacetonitrile, 2-fluoropropionitrile, 3-fluoropropionitrile, 2,2-difluoropropionitrile, 2,3-difluoropropionitrile, 3,3-difluoropropionitrile, 2,2,3-trifluoropropionitrile, 3,3,3-trifluoropropionitrile, 3,3'-oxydipropionitrile, 3,3'-thiodipropionitrile, 1,2,3-propanetricarbonitrile, 1,3,5-pentanetricarbonitrile, and pentafluoropropionitrile.

Specific examples of the dinitrile include malononitrile, succinonitrile, glutaronitrile, adiponitrile, pimelonitrile, suberonitrile, azelanitrile, sebaconitrile, undecanedinitrile, dodecanedinitrile, methylmalononitrile, ethylmalononitrile, isopropylmalononitrile, tert-butylmalononitrile, methylsuccinonitrile, 2,2-dimethylsuccinonitrile, 2,3-dimethylsuccinonitrile, 2,3,3-trimethylsuccinonitrile, 2,2,3,3-tetramethylsuccinonitrile, 2,3-diethyl-2,3-dimethylsuccinonitrile, 2,2-diethyl-3,3-dimethyl succinonitrile, bicyclohexyl-1,1-dicarbonitrile, bicyclohexyl-2,2-dicarbonitrile, bicyclohexyl-3,3-dicarbonitrile, 2,5-dimethyl-2,5-hexanedicarbonitrile, 2,3-diisobutyl-2,3-dimethylsuccinonitrile, 2,2-diisobutyl-3,3-dimethylsuccinonitrile, 2-methylglutaronitrile, 2,3-dimethylglutaronitrile, 2,4-dimethylglutaronitrile, 2,2,3,3-tetramethylglutaronitrile, 2,2,4,4-tetramethylglutaronitrile, 2,2,3,4-tetramethylglutaronitrile, 2,3,3,4-tetramethylglutaronitrile, maleonitrile, fumaronitrile, 1,4-dicyanopentane, 2,6-dicyanoheptane, 2,7-dicyanooctane, 2,8-dicyanononane, 1,6-dicyanodecane, 1,2-dicyanobenzene, 1,3-dicyanobenzene, 1,4-dicyanobenzene, 3,3'-(ethylenedioxy)dipropionitrile, and 3,3'-(ethylenedithio)dipropionitrile.

Thereamong, a dinitrile, such as malononitrile, succinonitrile, glutaronitrile, adiponitrile, pimelonitrile, suberonitrile, azelanitrile, sebaconitrile, undecanedinitrile or dodecanedinitrile, can contribute to the formation of a stable film-like structure and is thus more preferably used.

The content of the nitrile is not particularly restricted and may be set arbitrarily as long as the effects of the present invention are not markedly impaired; however, it is preferably 0.001% by mass to 5.0% by mass with respect to the amount of the nonaqueous electrolyte solution of the present embodiment.

When the content of the nitrile is not lower than this lower limit, the nitrile can bring about a sufficient cycle characteristics-improving effect in a nonaqueous electrolyte secondary battery. Meanwhile, when the content of the nitrile is not higher than the upper limit, an increase in the initial resistance of a nonaqueous electrolyte secondary battery is be avoided, so that deterioration of the rate characteristics can be inhibited. The content of the nitrile is more preferably 0.01% by mass or higher, still more preferably 0.1% by mass or higher, particularly preferably 0.2% by mass or higher, but more preferably 4.0% by mass or less, still more preferably 3.0% by mass or less, particularly preferably 2.5% by mass or less.

<1-4-1-7. Cyclic Sulfonate Ester>

Among the specific additives, the cyclic sulfonate ester is not particularly restricted, and any cyclic sulfonate ester can be used.

The cyclic sulfonate ester may be, for example, a saturated cyclic sulfonate ester or a unsaturated cyclic sulfonate ester.

Specific examples of the saturated cyclic sulfonate ester include 1,3-propane sultone, 1-fluoro-1,3-propane sultone, 2-fluoro-1,3-propane sultone, 3-fluoro-1,3-propane sultone, 1-methyl-1,3-propane sultone, 2-methyl-1,3-propane sultone, 3-methyl-1,3-propane sultone, 1,4-butane sultone, 1-fluoro-1,4-butane sultone, 2-fluoro-1,4-butane sultone, 3-fluoro-1,4-butane sultone, 4-fluoro-1,4-butane sultone, 1-methyl-1,4-butane sultone, 2-methyl-1,4-butane sultone, 3-methyl-1,4-butane sultone, and 4-methyl-1,4-butane sultone.

Specific examples of the unsaturated cyclic sulfonate ester include 1-propene-1,3-sultone, 2-propene-1,3-sultone, 1-fluoro-1-propene-1,3-sultone, 2-fluoro-1-propene-1,3-sultone, 3-fluoro-1-propene-1,3-sultone, 1-fluoro-2-propene-1,3-sultone, 2-fluoro-2-propene-1,3-sultone, 3-fluoro-2-propene-1,3-sultone, 1-methyl-1-propene-1,3-sultone, 2-methyl-1-propene-1,3-sultone, 3-methyl-1-propene-1,3-sultone, 1-methyl-2-propene-1,3-sultone, 2-methyl-2-propene-1,3-sultone, 3-methyl-2-propene-1,3-sultone, 1-butene-1,4-sultone, 2-butene-1,4-sultone, 3-butene-1,4-sultone, 1-fluoro-1-butene-1,4-sultone, 2-fluoro-1-butene-1,4-sultone, 3-fluoro-1-butene-1,4-sultone, 4-fluoro-1-butene-1,4-sultone, 1-fluoro-2-butene-1,4-sultone, 2-fluoro-2-butene-1,4-sultone, 3-fluoro-2-butene-1,4-sultone, 4-fluoro-2-butene-1,4-sultone, 1-fluoro-3-butene-1,4-sultone, 2-fluoro-3-butene-1,4-sultone, 3-fluoro-3-butene-1,4-sultone, 4-fluoro-3-butene-1,4-sultone, 1-methyl-1-butene-1,4-sultone, 2-methyl-1-butene-1,4-sultone, 3-methyl-1-butene-1,4-sultone, 4-methyl-1-butene-1,4-sultone, 1-methyl-2-butene-1,4-sultone, 2-methyl-2-butene-1,4-sultone, 3-methyl-2-butene-1,4-sultone, 4-methyl-2-butene-1,4-sultone, 1-methyl-3-butene-1,4-sultone, 2-methyl-3-butene-1,4-sultone, 3-methyl-3-butene-1,4-sultone, and 4-methyl-3-butene-1,4-sultone.

Among the above-exemplified cyclic sulfonate esters, 1,3-propane sultone, 1-fluoro-1,3-propane sultone, 2-fluoro-1,3-propane sultone, 3-fluoro-1,3-propane sultone, and 1-propene-1,3-sultone can be more suitably used since they are readily available and can contribute to the formation of a stable film-like structure.

The content of the cyclic sulfonate ester is not particularly restricted, and may be set arbitrarily as long as the effects of the present invention are not markedly impaired; however, it is 0.001% by mass to 3.0% by mass in 100% by mass of the nonaqueous electrolyte solution of the present embodiment.

When the content of the cyclic sulfonate ester is not lower than this lower limit, the cyclic sulfonate ester can bring about a sufficient cycle characteristics-improving effect in an energy device. Meanwhile, when the content of the cyclic sulfonate ester is not higher than the upper limit, an increase in the energy device production cost can be avoided. The content of the cyclic sulfonate ester is more preferably 0.01% by mass or higher, still more preferably 0.1% by mass or higher, particularly preferably 0.2% by mass or higher, but more preferably 2.5% by mass or less, still more preferably 2.0% by mass or less, particularly preferably 1.8% by mass or less.

<1-4-1-8. Dicarboxylic Acid Complex Salt>

Among the specific additives, the dicarboxylic acid complex salt is not particularly restricted, and any dicarboxylic acid complex salt can be used.

The dicarboxylic acid complex salt may be, for example, a dicarboxylic acid complex salt in which the complex central element is boron, or a dicarboxylic acid complex salt in which the complex central element is phosphorus.

Specific examples of the dicarboxylic acid complex salt in which the complex central element is boron include lithium bis(oxalato)borate, lithium difluoro(oxalato)borate, lithium bis(malonato)borate, lithium difluoro(malonato)borate, lithium bis(methylmalonato)borate, lithium difluoro(methylmalonato)borate, lithium bis(dimethylmalonato)borate, and lithium difluoro(dimethylmalonato)borate.

Specific examples of the dicarboxylic acid complex salt in which the complex central element is phosphorus include lithium tris(oxalato)phosphate, lithium difluorobis(oxalato) phosphate, lithium tetrafluoro(oxalato)phosphate, lithium tris(malonato)phosphate, lithium difluorobis(malonato) phosphate, lithium tetrafluoro(malonato)phosphate, lithium tris(methylmalonato)phosphate, lithium difluorobis(methylmalonato)phosphate, lithium tetrafluoro(methylmalonato) phosphate, lithium tris(dimethylmalonato)phosphate, lithium difluorobis(dimethylmalonato)phosphate, and lithium tetrafluoro(dimethylmalonato)phosphate.

Among the above-exemplified dicarboxylic acid complex salts, lithium bis(oxalato)borate, lithium difluoro(oxalato) borate, lithium tris(oxalato)phosphate, lithium difluorobis (oxalato)phosphate, and lithium tetrafluoro(oxalato)phosphate can be more suitably used since they are readily available and can contribute to the formation of a stable film-like structure.

The content of the dicarboxylic acid complex salt is not particularly restricted, and may be set arbitrarily as long as the effects of the present invention are not markedly impaired; however, it is preferably 0.001% by mass to 2.5% by mass with respect to the amount of the nonaqueous electrolyte solution of the present embodiment.

When the content of the dicarboxylic acid complex salt is not lower than this lower limit, the dicarboxylic acid complex salt can bring about a sufficient cycle characteristics-improving effect in a nonaqueous electrolyte secondary battery. Meanwhile, when the content of the dicarboxylic acid complex salt is not higher than the upper limit, not only an increase in the production cost of a nonaqueous electrolyte secondary battery can be avoided, but also swelling in volume of a nonaqueous electrolyte secondary battery caused by gas generation can be avoided. The content of the dicarboxylic acid complex salt is more preferably 0.01% by mass or higher, still more preferably 0.1% by mass or higher, particularly preferably 0.2% by mass or higher, but more preferably 2.0% by mass or less, still more preferably 1.5% by mass or less, particularly preferably 1.2% by mass or less.

<1-4-1-9. Preferred Specific Additives>

As the above-described specific additives, it is preferred to incorporate at least one compound selected from fluorine atom-containing cyclic carbonates, carbon-carbon unsaturated bond-containing cyclic carbonates, difluorophosphate salts, fluorosulfate salts, cyclic sulfonate esters and dicarboxylic acid complex salts and, thereamong, a difluorophosphate salt or a fluorosulfate salt is more preferably incorporated, and a difluorophosphate salt is particularly preferably incorporated.

<1-4-2. Other Additives>

Examples of additives other than the specific additives include overcharge inhibitors, and auxiliary agents for improving the capacity retention and cycle characteristics after high-temperature storage.

<1-4-2-1. Overcharge Inhibitor>

Specific examples of the overcharge inhibitors include aromatic compounds, for example:

toluene derivatives, such as toluene, xylene, 2-fluorotoluene, 3-fluorotoluene, and 4-fluorotoluene;

unsubstituted or alkyl-substituted biphenyl derivatives, such as biphenyl, 2-methylbiphenyl, 3-methylbiphenyl, and 4-methylbiphenyl;

unsubstituted or alkyl-substituted terphenyl derivatives, such as o-terphenyl, m-terphenyl, and p-terphenyl;

partial hydrogenation products of unsubstituted or alkyl-substituted terphenyl derivatives;

cycloalkylbenzene derivatives, such as cyclopentylbenzene and cyclohexylbenzene;

alkylbenzene derivatives having a tertiary carbon directly bound to the benzene ring, such as cumene, 1,3-diisopropylbenzene, and 1,4-diisopropylbenzene;

alkylbenzene derivatives having a quaternary carbon directly bound to the benzene ring, such as t-butylbenzene, t-amylbenzene, t-hexylbenzene, and 1,1,3-trimethyl-3-phenylindane; and oxygen atom-containing aromatic compounds, such as diphenyl ether and dibenzofuran.

Other specific examples of the overcharge inhibitors include: partially fluorinated products of the above-described aromatic compounds, such as fluorobenzene, benzotrifluoride, 2-fluorobiphenyl, o-cyclohexylfluorobenzene, and p-cyclohexylfluorobenzene; and fluorine-containing anisole compounds, such as 2,4-difluoroanisole, 2,5-difluoroanisole, and 1,6-difluoroanisole.

Any of these overcharge inhibitors may be used singly, or two or more thereof may be used in any combination at any ratio. When an arbitrary combination of two or more overcharge inhibitors are used, the above-exemplified compounds belonging to the same classification may be used in combination, or the above-exemplified compounds belonging to different classifications may be used in combination.

When an overcharge inhibitor is incorporated, the amount thereof may be set arbitrarily as long as the effects of the present invention are not markedly impaired; however, it is preferably in a range of 0.001% by mass to 10% by mass with respect to the whole nonaqueous electrolyte solution (100% by mass).

By incorporating an overcharge inhibitor into the nonaqueous electrolyte solution of the present embodiment within a range that does not markedly impair the effects of the present invention, the safety of an energy device can be improved such that there would be no problem even if the battery were overcharged in a situation where an overcharge protection circuit does not properly operate due to an incorrect use, a failure of a charging apparatus or the like, which is preferred.

<1-4-2-2. Auxiliary Agent>

Specific examples of the auxiliary agents for improving the capacity retention and cycle characteristics after high-temperature storage include the followings:

carbonate compounds other than those corresponding to unsaturated bond-containing carbonates, such as erythritan carbonate and spiro-bis-dimethylene carbonate;

cyclic sulfites, such as ethylene sulfite;

open-chain sulfonate esters, such as methyl methanesulfonate and busulfan;

cyclic sulfones, such as sulfolane and sulfolene;

open-chain sulfones, such as dimethyl sulfone, diphenyl sulfone, and methyl phenyl sulfone;

sulfides, such as dibutyl disulfide, dicyclohexyl disulfide, and tetramethyl thiuram monosulfide;

sulfur-containing compounds, for example, sulfonamides such as N,N-dimethylmethane sulfonamide and N,N-diethylmethane sulfonamide;

nitrogen-containing compounds, such as 1-methyl-2-pyrrolidinone, 1-methyl-2-piperidone, 3-methyl-2-oxazolidinone, and 1,3-dimethyl-2-imidazolidinone;

hydrocarbon compounds, such as heptane, octane, and cycloheptane;

triple bond-containing compounds, such as propargyl 2-(diethoxyphosphoryl)acetate, 2-butynyl 2-(diethoxyphosphoryl)acetate, propargyl 2-(methanesulfonyloxy)propionate, propargyl methanesulfonyloxyacetate, lithium ethylpropargyloxycarbonyl phosphonate, lithium ethyl-2-butynyloxycarbonyl phosphonate, lithium propargyl sulfate, lithium 2-butynyl sulfate, propargyltrimethylsilyl sulfate, 2-butyne-1,4-diyl dimesylate, 2-butyne-1,4-diyl diethanesulfonate, 2-butyne-1,4-diyl diformate, 2-butyne-1,4-diyl diacetate, 2-butyne-1,4-diyl dipropionate, 4-hexadiyne-1,6-diyl dimethanesulfonate, propargyl methanesulfonate, 2-butynyl methanesulfonate, propargyl ethanesulfonate, propargyl vinyl sulfonate, propargyl methyl carbonate, propargyl ethyl carbonate, dipropargyl carbonate, propargyl formate, propargyl acetate, propargyl methacrylate, methyl propargyl oxalate, ethyl propargyl oxalate, and dipropargyl oxalate;

fluorine-containing aromatic compounds, such as fluorobenzene, difluorobenzene, and benzotrifluoride;

pentafluorophenyl compounds, such as pentafluorophenylmethane sulfonate, pentafluorophenyltrifluoromethane sulfonate, pentafluorophenyl acetate, pentafluorophenyl trifluoroacetate, and methylpentafluorophenyl carbonate; and sulfuric acid half esters, such as lithium methyl sulfate, lithium ethyl sulfate, sodium methyl sulfate, and sodium ethyl sulfate.

Any of these auxiliary agents may be used singly, or two or more thereof may be used in any combination at any ratio.

When the nonaqueous electrolyte solution of the present embodiment contains the above-described auxiliary agent(s), the content thereof may be set arbitrarily as long as the effects of the present invention are not markedly impaired; however, it is preferably in a range of 0.001% by mass to 10% by mass with respect to the whole nonaqueous electrolyte solution (100% by mass).

<1-5. Method of Producing Nonaqueous Electrolyte Solution>

The nonaqueous electrolyte solution of the present embodiment can be prepared by dissolving an electrolyte, the specific ether and, as required, the above-described "specific additives", "other additives" and the like, in the above-described nonaqueous solvent.

In the preparation of the nonaqueous electrolyte solution, raw materials of the nonaqueous electrolyte solution, namely an electrolyte such a lithium salt, the specific ether, the nonaqueous solvent, the specific additive(s), other additive(s) and the like, are preferably dehydrated in advance. As for the degree of this dehydration, it is desired that the dehydration is performed to a moisture content of usually 50 ppm or less, preferably 30 ppm or less.

By removing water from the nonaqueous electrolyte solution, for example, electrolysis of water, reaction between water and the lithium metal, and hydrolysis of the lithium salt are made less likely to occur. The means for performing the dehydration is not particularly restricted and, for example, a drying agent such as a molecular sieve may be used when a liquid such as a nonaqueous solvent is to be dehydrated. Meanwhile, when a solid such as an electrolyte is to be dehydrated, the solid may be heat-dried at a temperature lower than the temperature at which the solid is decomposed. An energy device using the nonaqueous electrolyte solution of the present embodiment will be described below in detail.

2. Nonaqueous Electrolyte Solution of Second Embodiment

[2. Nonaqueous Electrolyte Solution]

The second object of the present invention is achieved by the second embodiment.

The nonaqueous electrolyte solution according to the second embodiment of the present invention contains at least one selected from the group consisting of compounds represented by Formulae (a1) and (a2).

<2-1. Compounds Represented by Formulae (a1) and (a2)>

The compound represented by Formula (a1) and the compound represented by Formula (a2) will now be described in detail.

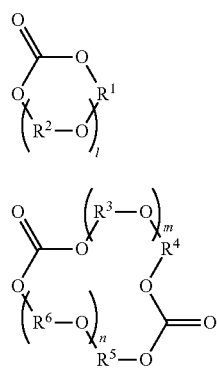

In Formulae (a1) and (a2), $R^1$ to $R^6$ each independently represent an alkylene group having 2 to 4 carbon atoms, which may be straight-chain or branched-chain.

With regard to the above-described $R^1$ to $R^6$, specific examples of preferred alkylene groups include —$CH_2CH_2$—, —$CH_2CH_2CH_2$—, —$CH(CH_3)CH_2$—, —$CH_2CH_2CH_2CH_2$—, —$CH(CH_3)CH_2CH_2$—, —$CH(CH_2CH_3)CH_2$—, —$CH_2CH(CH_3)CH_2$—, and —$CH_2C(CH_3)_2CH_2$—.

Thereamong, the alkylene group is more preferably —$CH_2CH_2$—, —$CH_2CH_2CH_2$— or —$CH(CH_3)CH_2$—, still more preferably —$CH_2CH_2$—. By adopting this structure, the metal capturing ability is improved, so that a durability-improving effect and a safety-improving effect are likely to be exerted. In addition, since the efficiency of producing the compounds represented by Formulae (a1) and (a2) is improved, the production load can be reduced.

In Formula (a1), l is an integer of 1 to 6, preferably 1 to 5, more preferably 1 to 4. By controlling the l to be in this range, the metal capturing ability is improved, so that a durability-improving effect and a safety-improving effect are likely to be exerted. In addition, since the efficiency of producing the compound represented by Formula (a1) is improved, the production load can be reduced.

In Formula (a2), m and n are each an integer of 0 to 6, with a proviso that, when either of m and n is 0, the other is an integer of 1 or larger. The m and n are each preferably 0 to 3, more preferably 0 to 2. By controlling the m and n to be in this range, the metal capturing ability is improved, so that a durability-improving effect and a safety-improving effect are likely to be exerted. In addition, since the efficiency of producing the compound represented by Formula (a2) is improved, the production load can be reduced.

Preferred specific examples of the compounds represented by Formulae (a1) and (a2) include the followings:

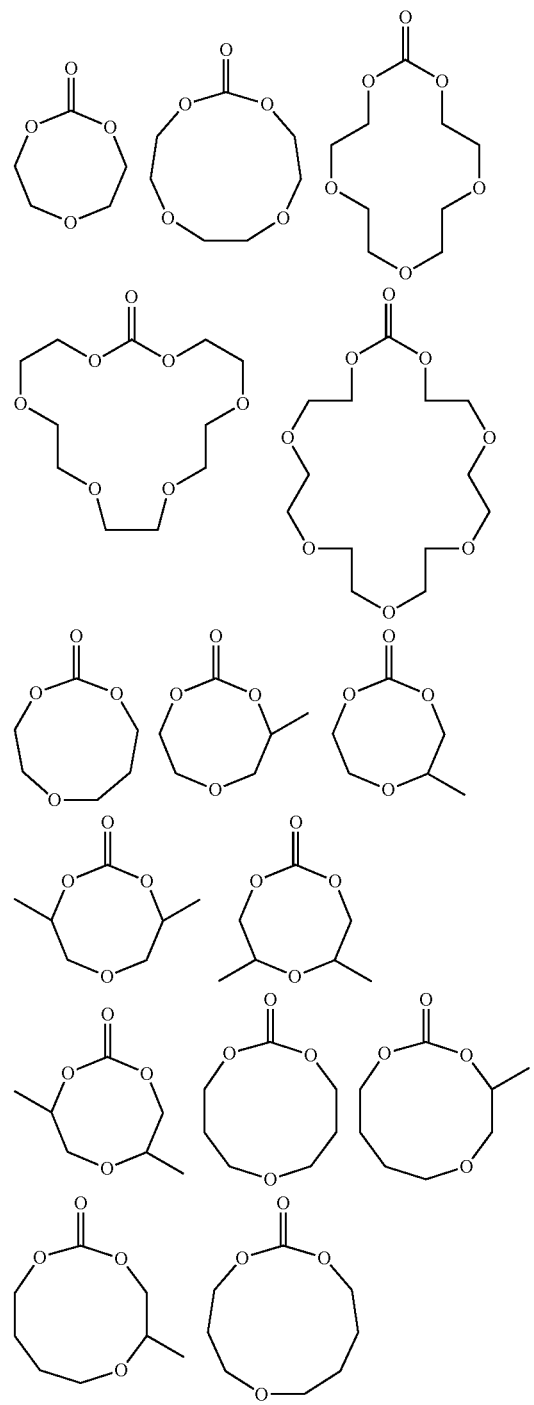

-continued

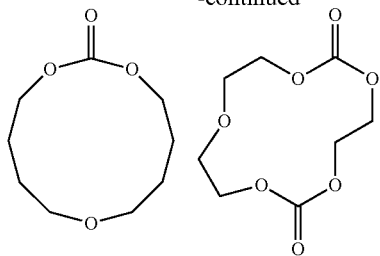
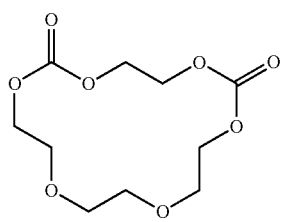
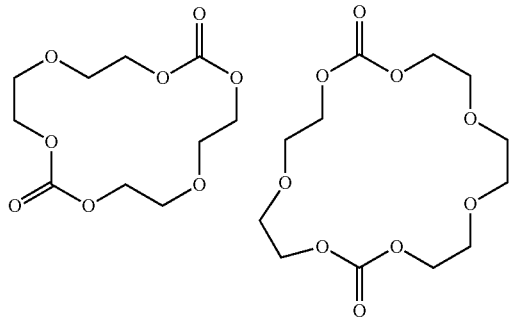
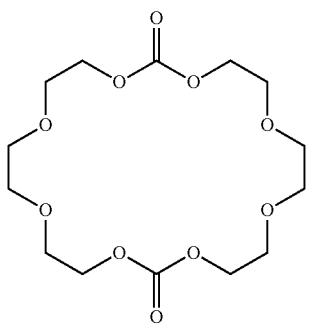

Thereamong, specific examples of more preferred compounds include the followings.

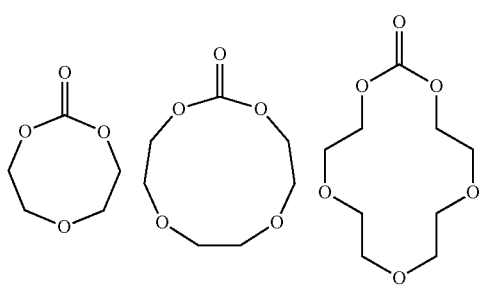

-continued

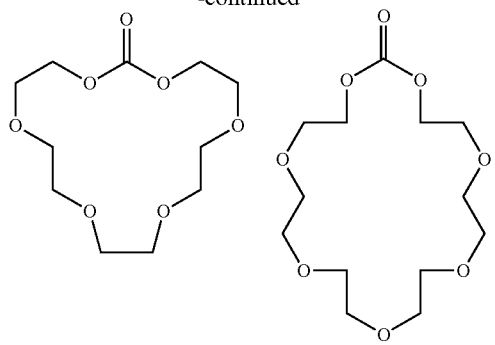
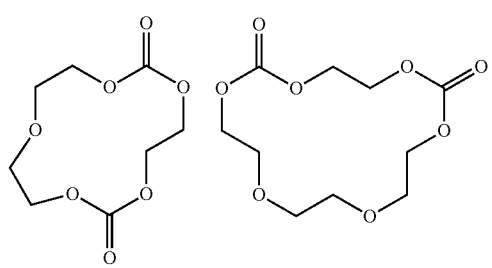
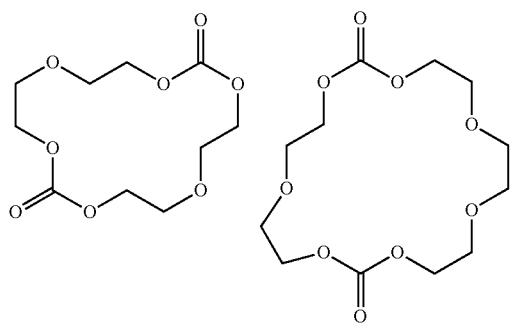
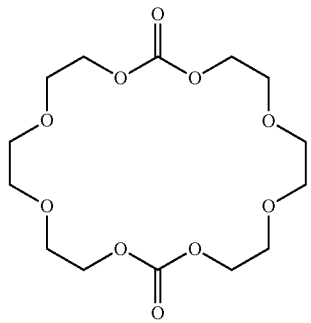

These compounds are preferred from the standpoint of improving the efficiency of producing the compounds represented by Formulae (a1) and (a2) and thereby reducing the production load.

Thereamong, specific examples of still more preferred compounds include the followings.

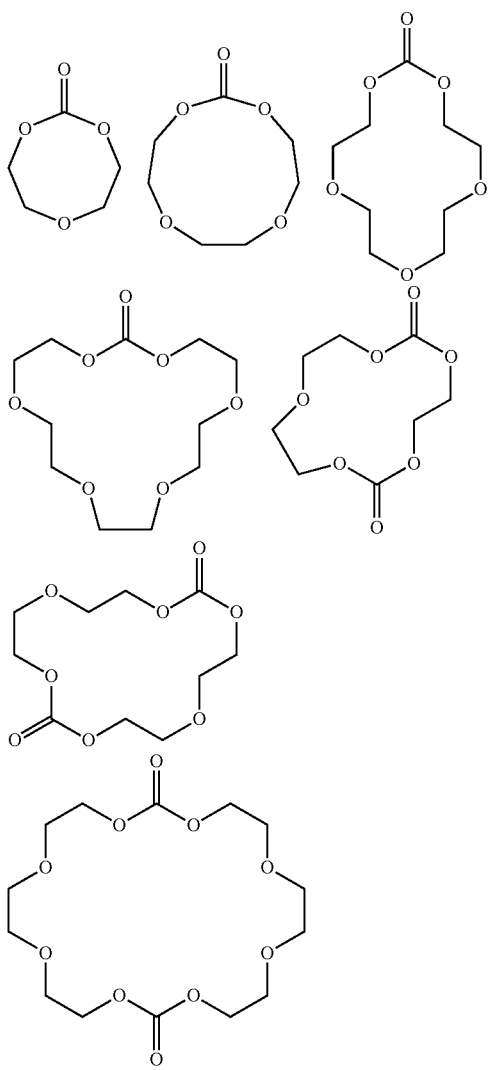

These compounds are preferred from the standpoint of improving the metal capturing ability and thereby making a durability improving effect and a safety improving effect more likely to be exerted.

The compounds represented by Formulae (a1) and (a2) may be used singly, or two or more thereof may be used in any combination at any ratio. The content of the compounds represented by Formulae (a1) and (a2) is not particularly restricted and may be set arbitrarily as long as the effects of the present invention are not markedly impaired; however, it is usually 0.0001% by mass or higher, preferably 0.001% by mass or higher, more preferably 0.01% by mass or higher, but usually 5% by mass or less, preferably 3% by mass or less, more preferably 2% by mass or less. The content of the compounds represented by Formulae (a1) and (a2) is preferably in this range since the durability can be further improved in terms of the cycle capacity, the storage capacity and the input-output characteristics, and the battery swelling can be further reduced.

A method of producing the compounds represented by Formulae (a1) and (a2) is not particularly restricted, and these compounds can be produced by a combination of any known methods.

For example, the compounds represented by Formulae (a1) and (a2) are produced by allowing glycols having the corresponding ether structures to react with phosgene or its alternative compound in a diluted condition and subsequently isolating and purifying the respective compounds from the resulting mixture.

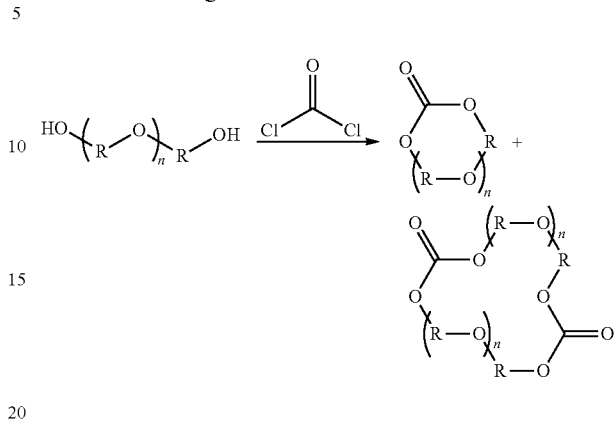

The nonaqueous electrolyte solution containing the compound(s) represented by Formula (a1) and/or (a2) may be prepared by any known method, and the method is not particularly restricted. Examples thereof include: a method of adding the compound(s) represented by Formula (a1) and/or (a2), which has/have been separately synthesized, to a nonaqueous electrolyte solution; a method of adding the compound(s) represented by Formula (a1) and/or (a2), which has/have been separately synthesized, to a solvent and subsequently dissolving an electrolyte salt in the resultant to prepare a nonaqueous electrolyte solution; a method of mixing the compound(s) represented by Formula (a1) and/or (a2) into a battery constituent such as the below-described active material or electrode plate to produce a battery element in advance and allowing the compound(s) represented by Formula (a1) and/or (a2) to be dissolved in a nonaqueous electrolyte solution at the time of assembling an energy device, such as a nonaqueous electrolyte secondary battery, by injection of the nonaqueous electrolyte solution; and a method of mixing compounds capable of yielding the compound(s) represented by Formula (a1) and/or (a2) into a nonaqueous electrolyte solution or nonaqueous electrolyte secondary battery in advance to later obtain an electrolyte solution containing the compound(s) represented by Formula (a1) and/or (a2) in the nonaqueous electrolyte solution or nonaqueous electrolyte secondary battery. In the present embodiment, any of these methods may be employed.

<2-2. Electrolyte>

The nonaqueous electrolyte solution of the present embodiment contains an electrolyte. The nonaqueous electrolyte solution may contain at least one lithium salt as the electrolyte. The lithium salt is not particularly restricted as long as it is known to be used as an electrolyte, and any lithium salt, specific examples of which include the followings, can be used.

Specific examples of the lithium salt include:

inorganic lithium salts, such as $LiBF_4$, $LiClO_4$, $LiAlF_4$, $LiPF_4$, $LiSbF_6$, $LiTaF_6$, and $LiWF_7$;

lithium fluorophosphates other than $LiPF_6$, such as $LiPO_3F$ and $LiPO_2F_2$;

lithium tungstates, such as $LiWOF_5$;

lithium carboxylate, such as $HCO_2Li$, $CH_3CO_2Li$, $CH_2FCO_2Li$, $CHF_2CO_2Li$, $CF_3CO_2Li$, $CF_3CH_2CO_2Li$, $CF_3CF_2CO_2Li$, $CF_3CF_2CF_2CO_2Li$, and $CF_3CF_2CF_2CF_2CO_2Li$;

lithium sulfonates, such as $FSO_3Li$, $CH_3SO_3Li$, $CH_2FSO_3Li$, $CHF_2SO_3Li$, $CF_3SO_3Li$, $CF_3CF_2SO_3Li$, $CF_3CF_2CF_2SO_3Li$, and $CF_3CF_2CF_2CF_2SO_3Li$;

sulfate salts, such as lithium methyl sulfate, lithium ethyl sulfate, lithium 2-propynyl sulfate, lithium 1-methyl-2-propynyl sulfate, lithium 1,1-dimethyl-2-propynyl sulfate, lithium 2,2,2-trifluoroethyl sulfate, and dilithium ethylene disulfate;

lithium imide salts, such as $LiN(FCO_2)_2$, $LiN(FCO)(FSO_2)$, $LiN(FSO_2)_2$, $LiN(FSO_2)(CF_3SO_2)$, $LiN(CF_3SO_2)_2$, $LiN(C_2F_5SO_2)_2$, lithium cyclic 1,2-perfluoroethane disulfonylimide, lithium cyclic 1,3-perfluoropropane disulfonylimide, and $LiN(CF_3SO_2)(C_4F_9SO_2)$;

lithium methide salts, such as $LiC(FSO_2)_3$, $LiC(CF_3SO_2)_3$, and $LiC(C_2F_5SO_2)_3$;

lithium oxalate salts, such as lithium difluorooxalatoborate, lithium bis(oxalato)borate, lithium tetrafluorooxalatophosphate, lithium difluorobis(oxalato)phosphate, and lithium tris(oxalato)phosphate; and fluorine-containing organic lithium salts, such as $LiPF_4(CF_3)_2$, $LiPF_4(C_2F_5)_2$, $LiPF_4(CF_3SO_2)_2$, $LiPF_4(C_2F_5SO_2)_2$, $LiBF_3CF_3$, $LiBF_3C_2F_5$, $LiBF_3C_3F_7$, $LiBF_2(CF_3)_2$, $LiBF_2(C_2F_5)_2$, $LiBF_2(CF_3SO_2)_2$, and $LiBF_2(C_2F_5SO_2)_2$.

From the standpoint of further enhancing the effects of improving the input-output characteristics after a durability test, such as a high-temperature storage test or a cycle test, as well as the charge-discharge rate characteristics and the impedance characteristics, the lithium salt is preferably one selected from inorganic lithium salts, lithium fluorophosphates, lithium sulfonates, lithium imide salts, and lithium oxalate salts.

Among these lithium salts, for example, $LiPF_6$, $LiBF_4$, $LiSbF_6$, $LiTaF_6$, $LiPO_3F$, $LiPO_2F_2$, $FSO_3Li$, $CF_3SO_3Li$, $LiN(FSO_2)_2$, $LiN(FSO_2)(CF_3SO_2)$, $LiN(CF_3SO_2)_2$, $LiN(C_2F_5SO_2)_2$, lithium cyclic 1,2-perfluoroethane disulfonylimide, lithium cyclic 1,3-perfluoropropane disulfonylimide, $LiC(FSO_2)_3$, $LiC(CF_3SO_2)_3$, $LiC(C_2F_5SO_2)_3$, lithium difluorooxalatoborate, lithium bis(oxalato)borate, lithium tetrafluorooxalatophosphate, lithium difluorobis(oxalato)phosphate, and lithium tris(oxalato)phosphate are particularly preferred because of their effects of improving the input-output characteristics, the high-rate charge-discharge characteristics, the impedance characteristics, the high-temperature storage characteristics, the cycle characteristics and the like.

A total concentration of these electrolytes in the nonaqueous electrolyte solution is not particularly restricted; however, it is usually 8% by mass or higher, preferably 8.5% by mass or higher, more preferably 9% by mass or higher. The upper limit of the total concentration is usually 18% by mass or lower, preferably 17% by mass or lower, more preferably 16% by mass or lower. When the total concentration of the electrolytes is in this range, an electrical conductivity appropriate for battery operation is attained, which is preferred.

These electrolytes may be used singly, or in combination of two or more thereof. When two or more electrolytes are used in combination, examples of preferred combinations include: $LiPF_6$ and $LiBF_4$; $LiPF_6$ and $LiPO_2F_2$; $LiPF_6$ and $FSO_3Li$; $LiPF_6$ and $LiN(FSO_2)_2$; $LiPF_6$ and $LiN(CF_3SO_2)_2$; $LiPF_6$ and lithium bis(oxalato)borate; $LiPF_6$ and lithium tetrafluorooxalato phosphate; $LiPF_6$ and lithium difluorobis(oxalato)phosphate; $LiPF_6$, $LiBF_4$ and $LiPO_2F_2$; $LiPF_6$, $LiBF_4$ and $FSO_3Li$; $LiPF_6$, $LiPO_2F_2$ and $FSO_3Li$; $LiPF_6$, $LiPO_2F_2$ and lithium bis(oxalato)borate; $LiPF_6$, $LiPO_2F_2$ and lithium difluorobis(oxalato)phosphate; $LiPF_6$, $LiPO_2F_2$ and $LiN(FSO_2)_2$; $LiPF_6$, $LiPO_2F_2$ and $LiN(CF_3SO_2)_2$; $LiPF_6$, $FSO_3Li$ and lithium bis(oxalato)borate; and $LiPF_6$, $FSO_3Li$ and lithium difluorobis(oxalato)phosphate, and these combinations have effects of improving the input-output characteristics, the high-temperature storage characteristics and the cycle characteristics. In this case, the content of $LiPF_6$ in the nonaqueous electrolyte solution is preferably 7% by mass or higher, more preferably 7.5% by mass or higher, still more preferably 8% by mass or higher, but preferably 16% by mass or less, more preferably 15% by mass or less, still more preferably 14% by mass or less, and the content of $LiBF_4$, $LiPO_2F_2$, $FSO_3Li$, $LiN(FSO_2)_2$, $LiN(CF_3SO_2)_2$, lithium bis(oxalato)borate or lithium difluorobis(oxalato)phosphate in the nonaqueous electrolyte solution is preferably 0.01% by mass or higher, more preferably 0.05% by mass or higher, still more preferably 0.1% by mass or higher, but preferably 5% by mass or less, more preferably 4% by mass or less, still more preferably 3% by mass or less. When the concentration of $LiPF_6$ is in the above-described preferred range, an appropriate balance is attained between the total ion content in the nonaqueous electrolyte solution and the viscosity of the nonaqueous electrolyte solution; therefore, the battery internal impedance is reduced without an excessive reduction in the ionic conductivity, and the effects of improving the input-output characteristics, the cycle characteristics and the storage characteristics, which are attributed to the incorporation of $LiPF_6$, are more likely to be exerted.

A particularly preferred combination of electrolytes is a combination of $LiPF_6$ and $LiPO_2F_2$. By using these electrolytes in combination with the compound represented by Formula (a1) or (a2), elution of a transition metal oxide from a positive electrode tends to be effectively inhibited. In addition, with this combination, an energy device having excellent discharge performance tends to be realized.

The above-described electrolyte materials can be produced by a conventionally known method.

The nonaqueous electrolyte solution containing the above-described electrolyte materials may be prepared by any known method, and the method is not particularly restricted. Examples thereof include: a method of adding the electrolyte materials, which have been separately synthesized, to a nonaqueous electrolyte solution; a method of mixing the electrolyte materials into a battery constituent such as the below-described active material or electrode plate to produce a battery element in advance and allowing the electrolyte materials to be dissolved in a nonaqueous electrolyte solution at the time of assembling a battery by injection of the nonaqueous electrolyte solution; and a method of allowing water to coexist in a battery constituent such as an active material, an electrode plate or a separator, and allowing other electrolyte materials to be generated in the system at the time of assembling a nonaqueous electrolyte secondary battery using a nonaqueous electrolyte solution containing the above-described electrolyte materials. In the present embodiment, any of these methods may be employed.

The same applies to a case of incorporating $FSO_3Li$ into an electrolyte solution.

A method of measuring the content of each electrolyte in the above-described nonaqueous electrolyte solution and nonaqueous electrolyte secondary battery is not particularly restricted, and any known method may be employed. Specific examples thereof include ion chromatography and $^{19}F$ nuclear magnetic resonance spectrometry (hereinafter, may be referred to as "NMR").

<2-3. Nonaqueous Solvent>

Similarly to a general nonaqueous electrolyte solution, the nonaqueous electrolyte solution according to one embodiment of the present invention usually contains, as its main component, a nonaqueous solvent that dissolves the above-described electrolyte. The nonaqueous solvent used in this embodiment is not particularly restricted, and any known organic solvent can be used. The organic solvent may be, for example, but not particularly limited to: a saturated cyclic carbonate, an open-chain carbonate, an open-chain carboxylic acid ester, a cyclic carboxylic acid ester, an ether-based compound, or a sulfone-based compound. These organic solvents may be used singly, or in combination of two or more thereof.

Further, in one embodiment of the present invention, the nonaqueous electrolyte solution preferably contains at least one selected from the group consisting of a cyclic carbonate, an open-chain carbonate, and an open-chain ester.

<2-3-1. Saturated Cyclic Carbonate>

Examples of the saturated cyclic carbonate include those containing an alkylene group having 2 to 4 carbon atoms.

Specific examples of the saturated cyclic carbonates containing an alkylene group having 2 to 4 carbon atoms include ethylene carbonate, propylene carbonate, and butylene carbonate. Thereamong, ethylene carbonate and propylene carbonate are preferred from the standpoint of attaining an improvement of the battery characteristics that is attributed to an increase in the degree of lithium ion dissociation. Any of these saturated cyclic carbonates may be used singly, or two or more thereof may be used in any combination at any ratio.

The content of the saturated cyclic carbonate is not particularly restricted and may be set arbitrarily as long as the effects of the present invention are not markedly impaired; however, when a single saturated cyclic carbonate is used alone, the lower limit of the content is usually 3% by volume or higher, preferably 5% by volume or higher, in 100% by volume of the nonaqueous solvent. By controlling the content of the saturated cyclic carbonate to be in this range, a decrease in the electrical conductivity caused by a reduction in the dielectric constant of the nonaqueous electrolyte solution is avoided, so that the high-current discharge characteristics, the stability to the negative electrode, and the cycle characteristics of the nonaqueous electrolyte secondary battery are all likely to be attained in favorable ranges. Meanwhile, the upper limit of the content of the saturated cyclic carbonate is usually 90% by volume or less, preferably 85% by volume or less, more preferably 80% by volume or less. By controlling the content of the saturated cyclic carbonate to be in this range, the viscosity of the nonaqueous electrolyte solution is kept in an appropriate range and a reduction in the ionic conductivity is inhibited, as a result of which the input-output characteristics of the nonaqueous electrolyte secondary battery can be further improved and the durability, such as cycle characteristics and storage characteristics, can be further enhanced, which is preferred.

The above-described saturated cyclic carbonates may be used in any combination of two or more thereof. One preferred combination is a combination of ethylene carbonate and propylene carbonate. In this case, the volume ratio of ethylene carbonate and propylene carbonate is preferably 99:1 to 40:60, more preferably 95:5 to 50:50. The lower limit of the amount of propylene carbonate with respect to all nonaqueous solvents is usually not less than 1% by volume, preferably not less than 2% by volume, more preferably not less than 3% by volume. Meanwhile, the upper limit of the amount of propylene carbonate is usually 30% by volume or less, preferably 25% by volume or less, more preferably 20% by volume or less. Propylene carbonate is preferably incorporated in this range since it leads to superior low-temperature characteristics.

<2-3-2. Linear Carbonate>

As the open-chain carbonate, one having 3 to 7 carbon atoms is preferred.

Specific examples of the open-chain carbonate having 3 to 7 carbon atoms include dimethyl carbonate, diethyl carbonate, di-n-propyl carbonate, diisopropyl carbonate, n-propyl isopropyl carbonate, ethyl methyl carbonate, methyl-n-propyl carbonate, n-butyl methyl carbonate, isobutyl methyl carbonate, t-butyl methyl carbonate, ethyl-n-propyl carbonate, n-butyl ethyl carbonate, isobutyl ethyl carbonate, and t-butyl ethyl carbonate.

Thereamong, dimethyl carbonate, diethyl carbonate, di-n-propyl carbonate, diisopropyl carbonate, n-propyl isopropyl carbonate, ethyl methyl carbonate and methyl-n-propyl carbonate are preferred, and dimethyl carbonate, diethyl carbonate and ethyl methyl carbonate are particularly preferred.

Further, a fluorine atom-containing open-chain carbonate (hereinafter, may be simply referred to as "fluorinated open-chain carbonate") can be preferably used as well. With regard to the "fluorinated open-chain carbonate", the same as described above for the first embodiment can be applied.

Any of the above-described open-chain carbonates may be used singly, or two or more thereof may be used in any combination at any ratio.

The content of the open-chain carbonate is not particularly restricted; however, it is usually 15% by volume or higher, preferably 20% by volume or higher, more preferably 25% by volume or higher, but usually 90% by volume or less, preferably 85% by volume or less, more preferably 80% by volume or less, in 100% by volume of the nonaqueous solvent. By controlling the content of the open-chain carbonate to be in this range, the viscosity of the nonaqueous electrolyte solution is kept in an appropriate range and a reduction in the ionic conductivity is inhibited, as a result of which the input-output characteristics and the charge-discharge rate characteristics of the nonaqueous electrolyte secondary battery are likely to be attained in favorable ranges. Further, a decrease in the electrical conductivity caused by a reduction in the dielectric constant of the nonaqueous electrolyte solution is avoided, so that the input-output characteristics and the charge-discharge rate characteristics of the nonaqueous electrolyte secondary battery are likely to be attained in favorable ranges.

Moreover, the battery performance can be markedly improved by using a specific open-chain carbonate in combination with ethylene carbonate in a specific amount.

For example, when dimethyl carbonate and ethyl methyl carbonate are selected as specific open-chain carbonates, the content of ethylene carbonate is not particularly restricted and may be set arbitrarily as long as the effects of the present invention are not markedly impaired; however, it is usually 15% by volume or higher, preferably 20% by volume or higher, but usually 45% by volume or less, preferably 40% by volume or less; the content of dimethyl carbonate is usually 20% by volume or higher, preferably 30% by volume or higher, but usually 50% by volume or less, preferably 45% by volume or less; and the content of ethyl methyl carbonate is also usually 20% by volume or higher, preferably 30% by volume or higher, but usually 50% by volume or less, preferably 45% by volume or less. By controlling these content values to be in the above-described respective ranges, the viscosity of the nonaqueous electrolyte solution can be reduced and the ionic conductivity can be increased while lowering the low-temperature precipitation point of the electrolyte, so that a high input/output can be attained even at low temperatures.

<2-3-3. Linear Carboxylic Acid Ester>

Examples of the open-chain carboxylic acid ester include those having a total of 3 to 7 carbon atoms in their respective structures.

Specific examples of such open-chain carboxylic acid esters include methyl acetate, ethyl acetate, n-propyl acetate, isopropyl acetate, n-butyl acetate, isobutyl acetate, t-butyl acetate, methyl propionate, ethyl propionate, n-propyl propionate, isopropyl propionate, n-butyl propionate, isobutyl propionate, t-butyl propionate, methyl butyrate, ethyl butyrate, n-propyl butyrate, isopropyl butyrate, methyl isobutyrate, ethyl isobutyrate, n-propyl isobutyrate, and isopropyl isobutyrate.

Thereamong, methyl acetate, ethyl acetate, n-propyl acetate, n-butyl acetate, methyl propionate, ethyl propionate, n-propyl propionate, isopropyl propionate, methyl butyrate or ethyl butyrate is preferred from the standpoints of improving the ionic conductivity through a reduction in the viscosity and inhibiting battery swelling under endurance conditions of cycle operation, storage and the like.

The content of the open-chain carboxylic acid ester is not particularly restricted and may be set arbitrarily as long as the effects of the present invention are not markedly impaired; however, it is usually 5% by volume or higher, preferably 8% by volume or higher, but usually 80% by volume or less, preferably 70% by volume or less, in 100% by volume of the nonaqueous solvent. By controlling the content of the open-chain carboxylic acid ester to be in this range, the electrical conductivity of the nonaqueous electrolyte solution is increased, so that the input-output characteristics and the charge-discharge rate characteristics of the nonaqueous electrolyte secondary battery are likely to be improved. Further, an increase in the negative electrode resistance is inhibited, so that the input-output characteristics and the charge-discharge rate characteristics of the nonaqueous electrolyte secondary battery are likely to be attained in favorable ranges.

When an open-chain carboxylic acid ester is used, it is preferred to use a cyclic carbonate in combination, and it is more preferred to use a cyclic carbonate and an open-chain carbonate in combination.

For example, when a cyclic carbonate and an open-chain carboxylic acid ester are used in combination, the content of the cyclic carbonate is not particularly restricted and may be set arbitrarily as long as the effects of the present invention are not markedly impaired; however, it is usually 15% by volume or higher, preferably 20% by volume, but usually 45% by volume or less, preferably 40% by volume or less, and the content of the open-chain carboxylic acid ester is usually 20% by volume or higher, preferably 30% by volume or higher, but usually 55% by volume or less, preferably 50% by volume or less. Further, when a cyclic carbonate, an open-chain carbonate and an open-chain carboxylic acid ester are used in combination, the content of the cyclic carbonate is not particularly restricted and may be set arbitrarily as long as the effects of the present invention are not markedly impaired; however, it is usually 15% by volume or higher, preferably 20% by volume, but usually 45% by volume or less, preferably 40% by volume or less, and the content of the open-chain carbonate is usually 25% by volume or higher, preferably 30% by volume or higher, but usually 84% by volume or less, preferably 80% by volume or less. It is preferred to control these content values to be in the above-described respective ranges since the viscosity of the nonaqueous electrolyte solution can be reduced and the ionic conductivity can be increased while lowering 161 the low-temperature precipitation point of the electrolyte, so that not only a further increased input/output can be attained even at low temperatures but also the battery swelling can be further reduced.

<2-3-4. Cyclic Carboxylic Acid Ester>

Examples of the cyclic carboxylic acid ester include those having a total of 3 to 12 carbon atoms in their respective structures.

Specific examples of such cyclic carboxylic acid esters include γ-butyrolactone, γ-valerolactone, γ-caprolactone, and ε-caprolactone. Thereamong, γ-butyrolactone is particularly preferred from the standpoint of attaining an improvement of the battery characteristics that is attributed to an increase in the degree of lithium ion dissociation. The content of the cyclic carboxylic acid ester is not particularly restricted and may be set arbitrarily as long as the effects of the present invention are not markedly impaired; however, it is usually 3% by volume or higher, preferably 5% by volume or higher, but usually 60% by volume or less, preferably 50% by volume or less, in 100% by volume of the nonaqueous solvent. By controlling the content of the cyclic carboxylic acid ester to be in this range, the electrical conductivity of the nonaqueous electrolyte solution is increased, so that the input-output characteristics and the charge-discharge rate characteristics of the nonaqueous electrolyte secondary battery are likely to be improved. Further, the viscosity of the nonaqueous electrolyte solution is kept in an appropriate range and a reduction in the electrical conductivity is avoided, so that an increase in the negative electrode resistance is inhibited, and the input-output characteristics and the charge-discharge rate characteristics of the nonaqueous electrolyte secondary battery are likely to be attained in favorable ranges.

<2-3-5. Ether-Based Compound>

The ether-based compound is preferably an open-chain ether having 3 to 10 carbon atoms, or a cyclic ether having 3 to 6 carbon atoms.

Examples of the open-chain ether having 3 to 10 carbon atoms include diethyl ether, di(2-fluoroethyl)ether, di(2,2-difluoroethyl)ether, di(2,2,2-trifluoroethyl)ether, ethyl(2-fluoroethyl)ether, ethyl(2,2,2-trifluoroethyl)ether, ethyl(1,1,2,2-tetrafluoroethyl)ether, (2-fluoroethyl)(2,2,2-trifluoroethyl)ether, (2-fluoroethyl)(1,1,2,2-tetrafluoroethyl)ether, (2,2,2-trifluoroethyl)(1,1,2,2-tetrafluoroethyl)ether, ethyl-n-propyl ether, ethyl(3-fluoro-n-propyl)ether, ethyl(3,3,3-trifluoro-n-propyl)ether, ethyl(2,2,3,3-tetrafluoro-n-propyl)ether, ethyl(2,2,3,3,3-pentafluoro-n-propyl)ether, 2-fluoroethyl-n-propyl ether, (2-fluoroethyl)(3-fluoro-n-propyl)ether, (2-fluoroethyl)(3,3,3-trifluoro-n-propyl)ether, (2-fluoroethyl)(2,2,3,3-tetrafluoro-n-propyl)ether, (2-fluoroethyl)(2,2,3,3,3-pentafluoro-n-propyl)ether, 2,2,2-trifluoroethyl-n-propyl ether, (2,2,2-trifluoroethyl)(3-fluoro-n-propyl)ether, (2,2,2-trifluoroethyl)(3,3,3-trifluoro-n-propyl)ether, (2,2,2-trifluoroethyl)(2,2,3,3-tetrafluoro-n-propyl)ether, (2,2,2-trifluoroethyl)(2,2,3,3,3-pentafluoro-n-propyl)ether, 1,1,2,2-tetrafluoroethyl-n-propyl ether, (1,1,2,2-tetrafluoroethyl)(3-fluoro-n-propyl)ether, (1,1,2,2-tetrafluoroethyl)(3,3,3-trifluoro-n-propyl)ether, (1,1,2,2-tetrafluoroethyl)(2,2,3,3-tetrafluoro-n-propyl)ether, (1,1,2,2-tetrafluoroethyl)(2,2,3,3,3-pentafluoro-n-propyl)ether, di-n-propyl ether, (n-propyl)(3-fluoro-n-propyl)ether, (n-propyl)(3,3,3-trifluoro-n-propyl)ether, (n-propyl)(2,2,3,3-tetrafluoro-n-propyl)ether, (n-propyl)(2,2,3,3,3-pentafluoro-n-propyl)ether, di(3-fluoro-n-propyl)ether, (3-fluoro-n-propyl)(3,3,3-trifluoro-n-propyl)ether, (3-fluoro-n-propyl)(2,2,3,3-tetrafluoro-n-propyl)ether, (3-fluoro-n-propyl)(2,2,3,3,3-pentafluoro-n-propyl)ether, di(3,3,3-trifluoro-n-propyl)ether, (3,3,3-trifluoro-n-propyl)(2,2,3,3-tetrafluoro-n-propyl)ether, (3,3,3-trifluoro-n-propyl)(2,2,3,3,3-pentafluoro-n-propyl)ether, di(2,2,3,3-tetrafluoro-n-propyl)ether, (2,2,3,3-tetrafluoro-n-propyl)(2,2,3,3,3-pentafluoro-n-propyl)ether, di(2,2,3,3,3-pentafluoro-n-propyl)ether, di-n-butyl ether, dimethoxymethane, methoxyethoxymethane, methoxy(2-fluoroethoxy)methane, methoxy(2,2,2-trifluoroethoxy)methane, methoxy(1,1,2,2-tetrafluoroethoxy)methane, diethoxymethane, ethoxy(2-fluoroethoxy)methane, ethoxy(2,2,2-trifluoroethoxy)methane, ethoxy(1,1,2,2-tetrafluoroethoxy)methane, di(2-fluoroethoxy)methane, (2-fluoroethoxy)(2,2,2-trifluoroethoxy)methane, (2-fluoroethoxy)(1,1,2,2-tetrafluoroethoxy)methane, di(2,2,2-trifluoroethoxy)methane, (2,2,2-trifluoroethoxy)(1,1,2,2-tetrafluoroethoxy)methane, di(1,1,2,2-tetrafluoroethoxy)methane, dimethoxyethane, methoxyethoxyethane, methoxy(2-fluoroethoxy)ethane, methoxy(2,2,2-trifluoroethoxy)ethane, methoxy(1,1,2,2-tetrafluoroethoxy)ethane, diethoxyethane, ethoxy(2-fluoroethoxy)ethane, ethoxy(2,2,2-trifluoroethoxy)ethane, ethoxy(1,1,2,2-tetrafluoroethoxy)ethane, di(2-fluoroethoxy)ethane, (2-fluoroethoxy)(2,2,2-trifluoroethoxy)ethane, (2-fluoroethoxy)(1,1,2,2-tetrafluoroethoxy)ethane, di(2,2,2-trifluoroethoxy)ethane, (2,2,2-trifluoroethoxy)(1,1,2,2-tetrafluoroethoxy)ethane, di(1,1,2,2-tetrafluoroethoxy)ethane, ethylene glycol di-n-propyl ether, ethylene glycol di-n-butyl ether, and diethylene glycol dimethyl ether.

Examples of the cyclic ether having 3 to 6 carbon atoms include tetrahydrofuran, 2-methyltetrahydrofuran, 3-methyltetrahydrofuran, 1,3-dioxane, 2-methyl-1,3-dioxane, 4-methyl-1,3-dioxane, 1,4-dioxane, and fluorinated compounds thereof.

Thereamong, dimethoxymethane, diethoxymethane, ethoxymethoxymethane, ethylene glycol di-n-propyl ether, ethylene glycol di-n-butyl ether, and diethylene glycol dimethyl ether are preferred since they have a high solvating capacity with lithium ions and thus improve the ion dissociation. Particularly preferred are dimethoxymethane, diethoxymethane, and ethoxymethoxymethane since they have a low viscosity and provide a high ionic conductivity.

The content of the ether-based compound is not particularly restricted and may be set arbitrarily as long as the effects of the present invention are not markedly impaired; however, it is usually 1% by volume or higher, preferably 2% by volume or higher, more preferably 3% by volume or higher, but usually 30% by volume or less, preferably 25% by volume or less, more preferably 20% by volume or less, in 100% by volume of the nonaqueous solvent. When the content of the ether-based compound is in this preferred range, an ionic conductivity-improving effect of an open-chain ether, which is attributed to an increase in the degree of lithium ion dissociation and a reduction in the viscosity, is likely to be ensured. In addition, when the negative electrode active material is a carbonaceous material, the phenomenon of co-intercalation of an open-chain ether thereto along with lithium ions can be inhibited; therefore, the input-output characteristics and the charge-discharge rate characteristics can be attained in appropriate ranges.

<2-3-6. Sulfone-Based Compound>

The sulfone-based compound is preferably a cyclic sulfone having 3 to 6 carbon atoms, or an open-chain sulfone having 2 to 6 carbon atoms. The number of sulfonyl groups in one molecule is preferably 1 or 2.

Examples of the cyclic sulfone include: monosulfone compounds, such as trimethylene sulfones, tetramethylene sulfones, and hexamethylene sulfones; and disulfone compounds, such as trimethylene disulfones, tetramethylene disulfones, and hexamethylene disulfones. Thereamong, from the standpoints of the dielectric constant and the viscosity, tetramethylene sulfones, tetramethylene disulfones, hexamethylene sulfones and hexamethylene disulfones are more preferred, and tetramethylene sulfones (sulfolanes) are particularly preferred.

As the sulfolanes, sulfolane and sulfolane derivatives (hereinafter, may be simply referred to as "sulfolanes", including sulfolane) are preferred. As the sulfolane derivatives, those in which one or more hydrogen atoms bound to carbon atoms constituting a sulfolane ring are substituted with a fluorine atom or an alkyl group are preferred.

Thereamong, for example, 2-methyl sulfolane, 3-methyl sulfolane, 2-fluorosulfolane, 3-fluorosulfolane, 2,2-difluorosulfolane, 2,3-difluorosulfolane, 2,4-difluorosulfolane, 2,5-difluorosulfolane, 3,4-difluorosulfolane, 2-fluoro-3-methyl sulfolane, 2-fluoro-2-methyl sulfolane, 3-fluoro-3-methyl sulfolane, 3-fluoro-2-methyl sulfolane, 4-fluoro-3-methyl sulfolane, 4-fluoro-2-methyl sulfolane, 5-fluoro-3-methyl sulfolane, 5-fluoro-2-methyl sulfolane, 2-fluoromethyl sulfolane, 3-fluoromethyl sulfolane, 2-difluoromethyl sulfolane, 3-difluoromethyl sulfolane, 2-trifluoromethyl sulfolane, 3-trifluoromethyl sulfolane, 2-fluoro-3-(trifluoromethyl)sulfolane, 3-fluoro-3-(trifluoromethyl)sulfolane, 4-fluoro-3-(trifluoromethyl)sulfolane, and 5-fluoro-3-(trifluoromethyl)sulfolane are preferred from the standpoint of attaining a high ionic conductivity and a high input/output.

Examples of the open-chain sulfone include dimethyl sulfone, ethyl methyl sulfone, diethyl sulfone, n-propyl methyl sulfone, n-propyl ethyl sulfone, di-n-propyl sulfone, isopropyl methyl sulfone, isopropyl ethyl sulfone, diisopropyl sulfone, n-butyl methyl sulfone, n-butyl ethyl sulfone, t-butyl methyl sulfone, t-butyl ethyl sulfone, monofluoromethyl methyl sulfone, difluoromethyl methyl sulfone, trifluoromethyl methyl sulfone, monofluoroethyl methyl sulfone, difluoroethyl methyl sulfone, trifluoroethyl methyl sulfone, pentafluoroethyl methyl sulfone, ethylmonofluoromethyl sulfone, ethyldifluoromethyl sulfone, ethyltrifluoromethyl sulfone, perfluoroethyl methyl sulfone, ethyltrifluoroethyl sulfone, ethylpentafluoroethyl sulfone, di(trifluoroethyl)sulfone, perfluorodiethyl sulfone, fluoromethyl-n-propyl sulfone, difluoromethyl-n-propyl sulfone, trifluoromethyl-n-propyl sulfone, fluoromethylisopropyl sulfone, difluoromethylisopropyl sulfone, trifluoromethylisopropyl sulfone, trifluoroethyl-n-propyl sulfone, trifluoroethylisopropyl sulfone, pentafluoroethyl-n-propyl sulfone, pentafluoroethylisopropyl sulfone, trifluoroethyl-n-butyl sulfone, trifluoroethyl-t-butyl sulfone, pentafluoroethyl-n-butyl sulfone, and pentafluoroethyl-t-butyl sulfone.

Thereamong, for example, dimethyl sulfone, ethyl methyl sulfone, diethyl sulfone, n-propyl methyl sulfone, isopropyl methyl sulfone, n-butyl methyl sulfone, t-butyl methyl sulfone, monofluoromethyl methyl sulfone, difluoromethyl methyl sulfone, trifluoromethyl methyl sulfone, monofluoroethyl methyl sulfone, difluoroethyl methyl sulfone, trifluoroethyl methyl sulfone, pentafluoroethyl methyl sulfone, ethylmonofluoromethyl sulfone, ethyldifluoromethyl sulfone, ethyltrifluoromethyl sulfone, ethyltrifluoroethyl sulfone, ethylpentafluoroethyl sulfone, trifluoromethyl-n-propyl sulfone, trifluoromethylisopropyl sulfone, trifluoroethyl-n-butyl sulfone, trifluoroethyl-t-butyl sulfone, trifluoromethyl-n-butyl sulfone, and trifluoromethyl-t-butyl sulfone are preferred from the standpoint of attaining a high ionic conductivity and a high input/output.

The content of the sulfone-based compound is not particularly restricted and may be set arbitrarily as long as the effects of the present invention are not markedly impaired; however, it is usually 0.3% by volume or higher, preferably 0.5% by volume or higher, more preferably 1% by volume or higher, but usually 40% by volume or less, preferably 35% by volume or less, more preferably 30% by volume or less, in 100% by volume of the nonaqueous solvent. When the content of the sulfone-based compound is in this preferred range, an effect of improving the durability, such as cycle characteristics and storage characteristics, is likely to be obtained, and the viscosity of the nonaqueous electrolyte solution is kept in an appropriate range, so that a reduction in the electrical conductivity can be avoided, and the input-output characteristics and the charge-discharge rate characteristics of the nonaqueous electrolyte secondary battery can be attained in favorable ranges.

<2-4. Auxiliary Agents>

The nonaqueous electrolyte solution of the present embodiment may further contain various auxiliary agents described below in detail.

<2-4-1. Carbonate Having at Least Either of Carbon-Carbon Unsaturated Bond and Fluorine Atom>

The nonaqueous electrolyte solution according to one embodiment of the present invention may further contain at least either of a carbon-carbon unsaturated bond-containing carbonate or a fluorine atom-containing carbonate.

The carbon-carbon unsaturated bond-containing carbonate is preferably, for example, a carbon-carbon unsaturated bond-containing cyclic carbonate (hereinafter, may be simply referred to as "unsaturated cyclic carbonate"), and the fluorine atom-containing carbonate is preferably, for example, a fluorine atom-containing cyclic carbonate.

The carbon-carbon unsaturated bond-containing cyclic carbonate is not particularly restricted as long as it is a cyclic carbonate having a carbon-carbon unsaturated bond, and any carbonate having a carbon-carbon unsaturated bond can be used. It is noted here that the term "carbon-carbon unsaturated bond-containing cyclic carbonate" used herein also encompasses a cyclic carbonate having an aromatic ring-containing substituent. A method of producing the unsaturated cyclic carbonate is not particularly restricted, and any known method can be selected to produce the unsaturated cyclic carbonate.

Examples of the unsaturated cyclic carbonate include: vinylene carbonates; ethylene carbonates substituted with a substituent having an aromatic ring or a carbon-carbon unsaturated bond; phenyl carbonates; vinyl carbonates; and allyl carbonates.

Examples of the vinylene carbonates include vinylene carbonate, methylvinylene carbonate, 4,5-dimethylvinylene carbonate, phenylvinylene carbonate, 4,5-diphenylvinylene carbonate, vinylvinylene carbonate, and allylvinylene carbonate.

Specific examples of the ethylene carbonates substituted with a substituent having an aromatic ring or a carbon-carbon unsaturated bond include vinylethylene carbonate, 4,5-divinylethylene carbonate, phenylethylene carbonate, 4,5-diphenylethylene carbonate, ethynylethylene carbonate, and 4,5-diethynylethylene carbonate.

Thereamong, vinylene carbonates and ethylene carbonates substituted with a substituent having an aromatic ring or a carbon-carbon unsaturated bond are preferred, and vinylene carbonate, 4,5-diphenylvinylene carbonate, 4,5-dimethylvinylene carbonate, vinylethylene carbonate and ethynylethylene carbonate are particularly preferred and can be used more suitably since they yield a stable interfacial protective film.

The molecular weight of the unsaturated cyclic carbonate is not particularly restricted and may be set arbitrarily as long as the effects of the present invention are not markedly impaired. The molecular weight of the unsaturated cyclic carbonate is usually 50 or higher, preferably 80 or higher, but preferably 250 or lower, preferably 150 or lower. When the molecular weight of the unsaturated cyclic carbonate is in this range, the solubility of the unsaturated cyclic carbonate in the nonaqueous electrolyte solution is likely to be ensured, so that the effects of the present invention are likely to be expressed sufficiently.

Any of the above-described unsaturated cyclic carbonates may be used singly, or two or more thereof may be used in any combination at any ratio. The content of the unsaturated cyclic carbonate(s) is not particularly restricted and may be set arbitrarily as long as the effects of the present invention are not markedly impaired. The content of the unsaturated cyclic carbonate(s) is usually 0.001% by mass or higher, preferably 0.01% by mass or higher, more preferably 0.1% by mass or higher, still more preferably 0.2% by mass or higher, but usually 10% by mass or less, preferably 8% by mass or less, more preferably 5% by mass or less, in 100% by mass of the nonaqueous electrolyte solution. When the content of the unsaturated cyclic carbonate(s) is in this range, the nonaqueous electrolyte secondary battery is likely to exhibit a sufficient high-temperature storage and cycle characteristics-improving effect.

The fluorine atom-containing cyclic carbonate (hereinafter, may be simply referred to as "fluorinated cyclic carbonate") is not particularly restricted as long as it is a cyclic carbonate having a fluorine atom.

Examples of the fluorinated cyclic carbonate include derivatives of alkylene-group containing cyclic carbonates having 2 to 6 carbon atoms, such as ethylene carbonate derivatives. Examples of the ethylene carbonate derivatives include fluorinated products of ethylene carbonate or ethylene carbonate substituted with an alkyl group (e.g., an alkyl group having 1 to 4 carbon atoms), among which those having 1 to 8 fluorine atoms are preferred.

Specific examples thereof include monofluoroethylene carbonate, 4,4-difluoroethylene carbonate, 4,5-difluoroethylene carbonate, 4-fluoro-4-methylethylene carbonate, 4,5-difluoro-4-methyl ethylene carbonate, 4-fluoro-5-methyl ethylene carbonate, 4,4-difluoro-5-methylethylene carbonate, 4-(fluoromethyl)-ethylene carbonate, 4-(difluoromethyl)-ethylene carbonate, 4-(trifluoromethyl)-ethylene carbonate, 4-(fluoromethyl)-4-fluoroethylene carbonate, 4-(fluoromethyl)-5-fluoroethylene carbonate, 4-fluoro-4,5-dimethylethylene carbonate, 4,5-difluoro-4,5-dimethylethylene carbonate, and 4,4-difluoro-5,5-dimethyl ethylene carbonate.

Thereamong, at least one selected from the group consisting of monofluoroethylene carbonate, 4,4-difluoroethylene carbonate, 4,5-difluoroethylene carbonate and 4,5-difluoro-4,5-dimethylethylene carbonate is preferred from the standpoints of imparting the nonaqueous electrolyte solution with a high ionic conductivity and favorably forming an interface protective film.

Any of the above-described fluorinated cyclic carbonates may be used singly, or two or more thereof may be used in any combination at any ratio. The content of the fluorinated cyclic carbonate(s) is not particularly restricted and may be set arbitrarily as long as the effects of the present invention are not markedly impaired; however, it is usually 0.001% by mass or higher, preferably 0.01% by mass or higher, more preferably 0.1% by mass or higher, but usually 8% by mass or less, preferably 6% by mass or less, more preferably 5% by mass or less, in 100% by mass of the nonaqueous electrolyte solution. When the content of the fluorinated cyclic carbonate(s) is in this range, the nonaqueous electrolyte secondary battery is likely to exhibit sufficient cycle characteristics and high-temperature storage characteristics.

The fluorinated cyclic carbonate may be used as an auxiliary agent or a nonaqueous solvent of the nonaqueous electrolyte solution. When the fluorinated cyclic carbonate is used as a nonaqueous solvent, the content thereof is usually 8% by mass or higher, preferably 10% by mass or higher, more preferably 12% by mass or higher, but usually 85% by mass or less, preferably 80% by mass or less, more preferably 75% by mass or less, in 100% by mass of the nonaqueous electrolyte solution. When the content of the fluorinated cyclic carbonate is in this range, the nonaqueous electrolyte secondary battery is likely to exhibit a sufficient cycle characteristics-improving effect, and a reduction in the discharge capacity retention rate is likely to be avoided.

In the nonaqueous electrolyte solution according to one embodiment of the present invention, the above-described carbonate having at least either of a carbon-carbon unsaturated bond and a fluorine atom is preferably at least one selected from the group consisting of vinylene carbonate, vinylethylene carbonate, ethynylethylene carbonate, and fluoroethylene carbonate.

<2-4-2. Fluorinated Unsaturated Cyclic Carbonate>

As the fluorinated cyclic carbonate, a cyclic carbonate having an unsaturated bond and a fluorine atom (hereinafter, may be simply referred to as "fluorinated unsaturated cyclic carbonate") can be used. The fluorinated unsaturated cyclic carbonate is not particularly restricted. Particularly, one having 1 or 2 fluorine atoms is preferred. A method of producing the fluorinated unsaturated cyclic carbonate is not particularly restricted, and any known method can be selected to produce the fluorinated unsaturated cyclic carbonate.

Examples of the fluorinated unsaturated cyclic carbonate include vinylene carbonate derivatives, and ethylene carbonate derivatives substituted with a substituent having an aromatic ring or a carbon-carbon unsaturated bond.

Examples of the vinylene carbonate derivatives include 4-fluorovinylene carbonate, 4-fluoro-5-methylvinylene carbonate, 4-fluoro-5-phenylvinylene carbonate, and 4,5-difluorovinylene carbonate.

Examples of the ethylene carbonate derivatives substituted with a substituent having an aromatic ring or a carbon-carbon unsaturated bond include 4-fluoro-4-vinylethylene carbonate, 4-fluoro-5-vinyl ethylene carbonate, 4,4-difluoro-4-vinylethylene carbonate, 4,5-difluoro-4-vinylethylene carbonate, 4-fluoro-4,5-divinylethylene carbonate, 4,5-difluoro-4,5-divinylethylene carbonate, 4-fluoro-4-phenylethylene carbonate, 4-fluoro-5-phenylethylene carbonate, 4,4-difluoro-5-phenylethylene carbonate, and 4,5-difluoro-4-phenylethylene carbonate.

The molecular weight of the fluorinated unsaturated cyclic carbonate is not particularly restricted and may be set arbitrarily as long as the effects of the present invention are not markedly impaired. The molecular weight of the fluorinated unsaturated cyclic carbonate is usually 50 or higher, preferably 80 or higher, but preferably 250 or lower, preferably 150 or lower. When the molecular weight of the fluorinated unsaturated cyclic carbonate is in this range, the solubility of the fluorinated unsaturated cyclic carbonate in the nonaqueous electrolyte solution is likely to be ensured, so that the effects of the present invention are likely to be expressed.

Any of the above-described fluorinated unsaturated cyclic carbonates may be used singly, or two or more thereof may be used in any combination at any ratio. The amount of the fluorinated unsaturated cyclic carbonate(s) to be incorporated is not particularly restricted and may be set arbitrarily as long as the effects of the present invention are not markedly impaired. The content of the fluorinated unsaturated cyclic carbonate(s) is usually 0.01% by mass or higher, preferably 0.1% by mass or higher, more preferably 0.2% by mass or higher, but usually 5% by mass or less, preferably 4% by mass or less, more preferably 3% by mass or less, in 100% by mass of the nonaqueous electrolyte solution. When the content of the fluorinated cyclic carbonate(s) is in this range, the nonaqueous electrolyte secondary battery is likely to exhibit a sufficient cycle characteristics-improving effect.

<2-4-3. $SO_2$ Group-Containing Cyclic Compound>

The type of an $SO_2$ group-containing cyclic compound that can be used in the nonaqueous electrolyte solution of the present embodiment is not particularly restricted as long as it is a cyclic compound having an $SO_2$ group in the molecule; however, the $SO_2$ group-containing cyclic compound is preferably a compound containing a cyclic sulfonate ester or a compound containing a cyclic sulfate ester (hereinafter, may each be simply referred to as "cyclic sulfonate ester compound" or "cyclic sulfate ester compound"), more preferably a compound represented by the following Formula (3). A method of producing the $SO_2$ group-containing cyclic compound is not particularly restricted, and any known method can be selected to produce the $SO_2$ group-containing cyclic compound.

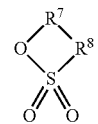

(3)

In Formula (3), $R^7$ and $R^8$ each independently represent an organic group constituted by atoms selected from the group consisting of a carbon atom, a hydrogen atom, a nitrogen atom, an oxygen atom, a sulfur atom, a phosphorus atom and a halogen atom, and $R^7$ and $R^8$ optionally contain an unsaturated bond together with —O—$SO_2$—.

$R^7$ and $R^8$ are each preferably an organic group constituted by atoms including a carbon atom, a hydrogen atom, an oxygen atom and a sulfur atom, particularly preferably a hydrocarbon group having 1 to 3 carbon atoms, or an organic group containing —O—$SO_2$—.

The molecular weight of the $SO_2$ group-containing cyclic compound is not particularly restricted and may be set arbitrarily as long as the effects of the present invention are not markedly impaired. The molecular weight of the $SO_2$ group-containing cyclic compound is usually 100 or higher, preferably 110 or higher, but preferably 250 or lower, preferably 220 or lower. When the molecular weight of the $SO_2$ group-containing cyclic compound is in this range, the solubility of the $SO_2$ group-containing cyclic compound in the nonaqueous electrolyte solution is likely to be ensured, so that the effects of the present invention are likely to be expressed.

Specific examples of the compound represented by Formula (3) include:

sultone compounds, such as 1,3-propane sultone, 1-fluoro-1,3-propane sultone, 2-fluoro-1,3-propane sultone, 3-fluoro-1,3-propane sultone, 1-methyl-1,3-propane sultone, 2-methyl-1,3-propane sultone, 3-methyl-1,3-propane sultone, 1-propene-1,3-sultone, 2-propene-1,3-sultone, 1-fluoro-1-propene-1,3-sultone, 2-fluoro-1-propene-1,3-sultone, 3-fluoro-1-propene-1,3-sultone, 1-fluoro-2-propene-1,3-sultone, 2-fluoro-2-propene-1,3-sultone, 3-fluoro-2-propene-1,3-sultone, 1-methyl-1-propene-1,3-sultone, 2-methyl-1-propene-1,3-sultone, 3-methyl-1-propene-1,3-sultone, 1-methyl-2-propene-1,3-sultone, 2-methyl-2-propene-1,3-sultone, 3-methyl-2-propene-1,3-sultone, 1,4-butane sultone, 1-fluoro-1,4-butane sultone, 2-fluoro-1,4-butane sultone, 3-fluoro-1,4-butane sultone, 4-fluoro-1,4-butane sultone, 1-methyl-1,4-butane sultone, 2-methyl-1,4-butane sultone, 3-methyl-1,4-butane sultone, 4-methyl-1,4-butane sultone, 1-butene-1,4-sultone, 2-butene-1,4-sultone, 3-butene-1,4-sultone, 1-fluoro-1-butene-1,4-sultone, 2-fluoro-1-butene-1,4-sultone, 3-fluoro-1-butene-1,4-sultone, 4-fluoro-1-butene-1,4-sultone, 1-fluoro-2-butene-1,4-sultone, 2-fluoro-2-butene-1,4-sultone, 3-fluoro-2-butene-1,4-sultone, 4-fluoro-2-butene-1,4-sultone, 1-fluoro-3-butene-1,4-sultone, 2-fluoro-3-butene-1,4-sultone, 3-fluoro-3-butene-1,4-sultone, 4-fluoro-3-butene-1,4-sultone, 1-methyl-1-butene-1,4-sultone, 2-methyl-1-butene-1,4-sultone, 3-methyl-1-butene-1,4-sultone, 4-methyl-1-butene-1,4-sultone, 1-methyl-2-butene-1,4-sultone, 2-methyl-2-butene-1,4-sultone, 3-methyl-2-butene-1,4-sultone, 4-methyl-2-butene-1,4-sultone, 1-methyl-3-butene-1,4-sultone, 2-methyl-3-butene-1,4-sultone, 3-methyl-3-butene-1,4-sultone, 4-methyl-3-butene-1,4-sultone, 1,5-pentane sultone, 1-fluoro-1,5-pentane sultone, 2-fluoro-1,5-pentane sultone, 3-fluoro-1,5-pentane sultone, 4-fluoro-1,5-pentane sultone, 5-fluoro-1,5-pentane sultone, 1-methyl-1,5-pentane sultone, 2-methyl-1,5-pentane sultone, 3-methyl-1,5-pentane sultone, 4-methyl-1,5-pentane sultone, 5-methyl-1,5-pentane sultone, 1-pentene-1,5-sultone, 2-pentene-1,5-sultone, 3-pentene-1,5-sultone, 4-pentene-1,5-sultone, 1-fluoro-1-pentene-1,5-sultone, 2-fluoro-1-pentene-1,5-sultone, 3-fluoro-1-pentene-1,5-sultone, 4-fluoro-1-pentene-1,5-sultone, 5-fluoro-1-pentene-1,5-sultone, 1-fluoro-2-pentene-1,5-sultone, 2-fluoro-2-pentene-1,5-sultone, 3-fluoro-2-pentene-1,5-sultone, 4-fluoro-2-pentene-1,5-sultone, 5-fluoro-2-pentene-1,5-sultone, 1-fluoro-3-pentene-1,5-sultone, 2-fluoro-3-pentene-1,5-sultone, 3-fluoro-3-pentene-1,5-sultone, 4-fluoro-3-pentene-1,5-sultone, 5-fluoro-3-pentene-1,5-sultone, 1-fluoro-4-pentene-1,5-sultone, 2-fluoro-4-pentene-1,5-sultone, 3-fluoro-4-pentene-1,5-sultone, 4-fluoro-4-pentene-1,5-sultone, 5-fluoro-4-pentene-1,5-sultone, 1-methyl-1-pentene-1,5-sultone, 2-methyl-1-pentene-1,5-sultone, 3-methyl-1-pentene-1,5-sultone, 4-methyl-1-pentene-1,5-sultone, 5-methyl-1-pentene-1,5-sultone, 1-methyl-2-pentene-1,5-sultone, 2-methyl-2-pentene-1,5-sultone, 3-methyl-2-pentene-1,5-sultone, 4-methyl-2-pentene-1,5-sultone, 5-methyl-2-pentene-1,5-sultone, 1-methyl-3-pentene-1,5-sultone, 2-methyl-3-pentene-1,5-sultone, 3-methyl-3-pentene-1,5-sultone, 4-methyl-3-pentene-1,5-sultone, 5-methyl-3-pentene-1,5-sultone, 1-methyl-4-pentene-1,5-sultone, 2-methyl-4-pentene-1,5-sultone, 3-methyl-4-pentene-1,5-sultone, 4-methyl-4-pentene-1,5-sultone, 5-methyl-4-pentene-1,5-sultone, 1,2-oxathiolane-2,2-dioxide-4-yl-acetate, 1,2-oxathiolane-2,2-dioxide-4-yl-propionate, 5-methyl-1,2-oxathiolane-2,2-dioxide-4-one-2,2-dioxide, and 5,5-dimethyl-1,2-oxathiolane-2,2-dioxide-4-one-2,2-dioxide;

disulfonate compounds, such as methylene methanedisulfonate and ethylene methanedisulfonate;

nitrogen-containing compounds, such as 1,2,3-oxathiazolidine-2,2-di oxide, 3-methyl-1,2,3-oxathiazolidine-2,2-dioxide, 3H-1,2,3-oxathiazole-2,2-dioxide, 5H-1,2,3-oxathiazole-2,2-dioxide, 1,2,4-oxathiazolidine-2,2-dioxide, 4-methyl-1,2,4-oxathiazolidine-2,2-dioxide, 3H-1,2,4-oxathiazole-2,2-dioxide, 5H-1,2,4-oxathiazole-2,2-dioxide, 1,2,5-oxathiazolidine-2,2-dioxide, 5-methyl-1,2,5-oxathiazolidine-2,2-dioxide, 3H-1,2,5-oxathiazole-2,2-dioxide, 5H-1,2,5-oxathiazole-2,2-dioxide, 1,2,3-oxathiazinane-2,2-dioxide, 3-methyl-1,2,3-oxathiazinane-2,2-dioxide, 5,6-dihydro-1,2,3-oxathiazine-2,2-dioxide, 1,2,4-oxathiazinane-2,2-dioxide, 4-methyl-1,2,4-oxathiazinane-2,2-dioxide, 5,6-dihydro-1,2,4-oxathiazine-2,2-dioxide, 3,6-dihydro-1,2,4-oxathiazine-2,2-dioxide, 3,4-dihydro-1,2,4-oxathiazine-2,2-dioxide, 1,2,5-oxathiazinane-2,2-dioxide, 5-methyl-1,2,5-oxathiazinane-2,2-dioxide, 5,6-dihydro-1,2,5-oxathiazine-2,2-dioxide, 3,6-dihydro-1,2,5-oxathiazine-2,2-dioxide, 3,4-dihydro-1,2,5-oxathiazine-2,2-dioxide, 1,2,6-oxathiazinane-2,2-dioxide, 6-methyl-1,2,6-oxathiazinane-2,2-dioxide, 5,6-dihydro-1,2,6-oxathiazine-2,2-dioxide, 3,4-dihydro-1,2,6-oxathiazine-2,2-dioxide, and 5,6-dihydro-1,2,6-oxathiazine-2,2-dioxide;

phosphorous-containing compounds, such as 1,2,3-oxathiaphospholane-2,2-di oxide, 3-methyl-1,2,3-oxathiaphospholane-2,2-dioxide, 3-methyl-1,2,3-oxathiaphospholane-2,2,3-trioxide, 3-methoxy-1,2,3-oxathiaphospholane-2,2,3-trioxide, 1,2,4-oxathiaphospholane-2,2-dioxide, 4-methyl-1,2,4-oxathiaphospholane-2,2-dioxide, 4-methyl-1,2,4-oxathiaphospholane-2,2,4-trioxide, 4-methoxy-1,2,4-oxathiaphospholane-2,2,4-trioxide, 1,2,5-oxathiaphospholane-2,2-dioxide, 5-methyl-1,2,5-oxathiaphospholane-2,2-dioxide, 5-methyl-1,2,5-oxathiaphospholane-2,2,5-trioxide, 5-methoxy-1,2,5-oxathiaphospholane-2,2,5-trioxide, 1,2,3-oxathiaphosphinane-2,2-dioxide, 3-methyl-1,2,3-oxathiaphosphinane-2,2-dioxide, 3-methyl-1,2,3-oxathiaphosphinane-2,2,3-trioxide, 3-methoxy-1,2,3-oxathiaphosphinane-2,2,3-trioxide, 1,2,4-oxathiaphosphinane-2,2-dioxide, 4-methyl-1,2,4-oxathiaphosphinane-2,2-dioxide, 4-methyl-1,2,4-oxathiaphosphinane-2,2,3-trioxide, 4-methyl-1,5,2,4-dioxathiaphosphinane-2,4-dioxide, 4-methoxy-1,5,2,4-dioxathiaphosphinane-2,4-dioxide, 3-methoxy-1,2,4-oxathiahosphinane-2,2,3-trioxide, 1,2,5-oxathiaphosphinane-2,2-dioxide, 5-methyl-1,2,5-oxathiaphosphinane-2,2-dioxide, 5-methyl-1,2,5-oxathiaphosphinane-2,2,3-trioxide, 5-methoxy-1,2,5-oxathiaphosphinane-2,2,3-trioxide, 1,2,6-oxathiaphosphinane-2,2-dioxide, 6-methyl-1,2,6-oxathiaphosphinane-2,2-dioxide, 6-methyl-1,2,6-oxathiaphosphinane-2,2,3-trioxide, and 6-methoxy-1,2,6-oxathiaphosphinane-2,2,3-trioxide; and alkylene sulfate compounds, such as 1,2-ethylene sulfate, 1,2-propylene sulfate, 1,3-propylene sulfate, 1,2-butylene sulfate, 1,3-butylene sulfate, 1,4-butylene sulfate, 1,2-pentylene sulfate, 1,3-pentylene sulfate, 1,4-pentylene sulfate, 1,5-pentylene sulfate, and vinylene sulfate.

Thereamong, 1,3-propane sultone, 1-fluoro-1,3-propane sultone, 2-fluoro-1,3-propane sultone, 3-fluoro-1,3-propane sultone, 1-propene-1,3-sultone, 1-fluoro-1-propene-1,3-sultone, 2-fluoro-1-propene-1,3-sultone, 3-fluoro-1-propene-1,3-sultone, 1,4-butane sultone, methylene methanedisulfonate, ethylene methanedisulfonate, 1,2-ethylene sulfate, 1,2-propylene sulfate and 1,3-propylene sulfate re preferred from the standpoint of improving the storage characteristics, and 1,3-propane sultone, 1-fluoro-1,3-propane sultone, 2-fluoro-1,3-propane sultone, 3-fluoro-1,3-propane sultone, 1-propene-1,3-sultone, methylene methanedisulfonate, ethylene methanedisulfonate, 1,2-ethylene sulfate and 1,3-propylene sulfate are more preferred.

Any of the above-described $SO_2$ group-containing cyclic compounds may be used singly, or two or more thereof may be used in any combination at any ratio. The amount of the $SO_2$ group-containing cyclic compound(s) to be incorporated with respect to the whole nonaqueous electrolyte solution of the present embodiment is not restricted and may be set arbitrarily as long as the effects of the present invention are not markedly impaired; however, the $SO_2$ group-containing cyclic compound(s) is/are incorporated into the nonaqueous electrolyte solution of the present embodiment at a concentration of usually 0.001% by mass or higher, preferably 0.01% by mass or higher, more preferably 0.1% by mass or higher, still more preferably 0.3% by mass or higher, but usually 10% by mass or lower, preferably 5% by mass or lower, more preferably 3% by mass or lower. When the concentration of the $SO_2$ group-containing cyclic compound(s) satisfies this range since the cyclic characteristics, the high-temperature storage characteristics and the like are thereby improved, and the battery swelling is thus reduced.

<2-4-4. Cyano Group-Containing Compound>

The type of a cyano group-containing compound that can be used in the nonaqueous electrolyte solution of the present embodiment is not particularly restricted as long as it is a compound having a cyano group in the molecule; however, the cyano group-containing compound is more preferably a compound represented by the following Formula (4). A method of producing the cyano group-containing compound is not particularly restricted, and any known method can be selected to produce the cyano group-containing compound.

$$(NC-T)_V U \qquad (4)$$

In Formula (4), T represents an organic group constituted by atoms selected from the group consisting of a carbon atom, a hydrogen atom, a nitrogen atom, an oxygen atom, a sulfur atom, a phosphorus atom and a halogen atom; U represents a V-valent organic group having 1 to 10 carbon atoms, which optionally has a substituent; V represents an integer of 1 or larger; and when V is 2 or larger, Ts may be the same or different from each other.

The molecular weight of the cyano group-containing compound is not particularly restricted and may be set arbitrarily as long as the effects of the present invention are not markedly impaired. The molecular weight of the cyano group-containing compound is usually 40 or higher, preferably 45 or higher, more preferably 50 or higher, but usually 200 or lower, preferably 180 or lower, more preferably 170 or lower. When the molecular weight is in this range, the solubility of the cyano group-containing compound in the nonaqueous electrolyte solution is likely to be ensured, so that the effects of the present invention are likely to be expressed.

Specific examples of the compound represented by Formula (4) include: compounds having one cyano group, such as acetonitrile, propionitrile, butyronitrile, isobutyronitrile, valeronitrile, isovaleronitrile, lauronitrile, 2-methylbutyronitrile, trimethylacetonitrile, hexanenitrile, cyclopentanecarbonitrile, cyclohexanecarbonitrile, acrylonitrile, methacrylonitrile, crotononitrile, 3-methylcrotononitrile, 2-methyl-2-butenenitrile, 2-pentenenitrile, 2-methyl-2-pentenenitrile, 3-methyl-2-pentenenitrile, 2-hexenenitrile, fluoroacetonitrile, difluoroacetonitrile, trifluoroacetonitrile, 2-fluoropropionitrile, 3-fluoropropionitrile, 2,2-difluoropropionitrile, 2,3-difluoropropionitrile, 3,3-difluoropropionitrile, 2,2,3-trifluoropropionitrile, 3,3,3-trifluoropropionitrile, 3,3'-oxydipropionitrile, 3,3'-thiodipropionitrile, 1,2,3-propanetricarbonitrile, 1,3,5-pentanetricarbonitrile, and pentafluoropropionitrile;

compounds having two cyano groups, such as malononitrile, succinonitrile, glutaronitrile, adiponitrile, pimelonitrile, suberonitrile, azelanitrile, sebaconitrile, undecanedinitrile, dodecanedinitrile, methylmalononitrile, ethylmalononitrile, isopropylmalononitrile, tert-butylmalononitrile, methylsuccinonitrile, 2,2-dimethylsuccinonitrile, 2,3-dimethylsuccinonitrile, trimethylsuccinonitrile, tetramethylsuccinonitrile, 3,3'-(ethylenedioxy)dipropionitrile, and 3,3'-(ethylenedithio)dipropionitrile;

compounds having three cyano groups, such as 1,2,3-tris(2-cyanoethoxy)propane and tris(2-cyanoethyl)amine;

cyanate compounds, such as methyl cyanate, ethyl cyanate, propyl cyanate, butyl cyanate, pentyl cyanate, hexyl cyanate, and heptyl cyanate;

sulfur-containing compounds, such as methyl thiocyanate, ethyl thiocyanate, propyl thiocyanate, butyl thiocyanate, pentyl thiocyanate, hexyl thiocyanate, heptyl thiocyanate, methanesulfonyl cyanide, ethanesulfonyl cyanide, propanesulfonyl cyanide, butanesulfonyl cyanide, pentanesulfonyl cyanide, hexanesulfonyl cyanide, heptanesulfonyl cyanide, methyl sulfurocyanidate, ethyl sulfurocyanidate, propyl sulfurocyanidate, butyl sulfurocyanidate, pentyl sulfurocyanidate, hexyl sulfurocyanidate, and heptyl sulfurocyanidate; and phosphorus-containing compounds, such as cyanodimethyl phosphine, cyanodimethyl phosphine oxide, methyl cyanodimethylphosphinate, methyl cyanomethylphosphinite, dimethylphosphinic cyanide, dimethylphosphinous cyanide, dimethyl cyanophosphonate, dimethyl cyanophosphonite, cyanomethyl methyl phosphonate, cyanomethyl methyl phosphinite, cyanodimethyl phosphate, and cyanodimethyl phosphite.

Thereamong, acetonitrile, propionitrile, butyronitrile, isobutyronitrile, valeronitrile, isovaleronitrile, lauronitrile, crotononitrile, 3-methylcrotononitrile, malononitrile, succinonitrile, glutaronitrile, adiponitrile, pimelonitrile, suberonitrile, azelanitrile, sebaconitrile, undecanedinitrile, and dodecanedinitrile are preferred from the standpoint of improving the storage characteristics, and a compound having two cyano groups, such as malononitrile, succinonitrile, glutaronitrile, adiponitrile, pimelonitrile, suberonitrile, azelanitrile, sebaconitrile, undecanedinitrile, and dodecanedinitrile are more preferred.

Any of the above-described cyano group-containing compounds may be used singly, or two or more thereof may be used in any combination at any ratio. The content of the cyano group-containing compound(s) with respect to the whole nonaqueous electrolyte solution of the present embodiment is not restricted and may be set arbitrarily as long as the effects of the present invention are not markedly impaired; however, in the nonaqueous electrolyte solution of the present embodiment, the cyano group-containing compound(s) is/are incorporated at a concentration of usually 0.001% by mass or greater, preferably 0.01% by mass or greater, more preferably 0.1% by mass or greater, still more preferably 0.3% by mass or greater, but usually 10% by mass or less, preferably 5% by mass or less, more preferably 3% by mass or less. When this range is satisfied, the input-output characteristics, the charge-discharge rate characteristics, the cycle characteristics, the high-temperature storage characteristics and the like are further improved.

<2-4-5. Isocyanate Compound>

The type of an isocyanate group-containing compound (hereinafter, may be simply referred to as "isocyanate compound") that can be used in the nonaqueous electrolyte solution of the present embodiment is not particularly restricted as long as it is a compound having an isocyanate in the molecule. As the isocyanate compound, a diisocyanate compound having two isocyanate groups in the molecule is preferred.

<2-4-5-1. Diisocyanate Compound>

As the diisocyanate compound that can be used in the nonaqueous electrolyte solution of the present embodiment, a compound represented by the following Formula (5), which has a nitrogen atom only in the respective isocyanate groups, is preferred:

NCO—X—NCO  (5)

In Formula (5), X represents an organic group having 1 to 15 carbon atoms, which optionally contains a cyclic structure. The number of carbon atoms of X is usually 2 or more, preferably 3 or more, more preferably 4 or more, but usually 14 or less, preferably 12 or less, more preferably 10 or less, still more preferably 8 or less.

In Formula (5), X is particularly preferably an organic group having 4 to 15 carbon atoms, which contains at least one cycloalkylene group having 4 to 6 carbon atoms or an aromatic hydrocarbon group. In this case, a hydrogen atom on the cycloalkylene group may be substituted with a methyl group or an ethyl group. The above-described diisocyanate compound having a cyclic structure is a sterically bulky molecule and is thus unlikely to cause a side reaction on a positive electrode, as a result of which the cycle characteristics and the high-temperature storage characteristics are improved. The binding site of a group bound to the cycloalkylene group or the aromatic hydrocarbon group is not particularly restricted and may be any of the meta-position, the para-position, and the ortho-position; however, it is preferably the meta-position or the para-position since this makes the cross-linking distance between coating films appropriate and an advantageous lithium ion conductivity is thereby attained, so that the resistance is likely to be reduced. In addition, the cycloalkylene group is preferably a cyclopentylene group or a cyclohexylene group from the standpoint of making the diisocyanate compound itself unlikely to cause a side reaction, and the cycloalkylene group is more preferably a cyclohexylene group since this is likely to result in a reduction in the resistance because of the effect of molecular mobility.

Further, the diisocyanate compound preferably has an alkylene group having 1 to 3 carbon atoms between the cycloalkylene group or the aromatic hydrocarbon group and an isocyanate group. Since the presence of the alkylene group makes the diisocyanate compound sterically bulky, a side reaction is unlikely to occur on a positive electrode. Moreover, as long as the number of carbon atoms of the alkylene group is 1 to 3, the ratio of isocyanate groups with respect to the total molecular weight is not largely modified; therefore, the effects of the present invention are likely to be expressed prominently.

The molecular weight of the diisocyanate compound represented by Formula (5) is not particularly restricted and may be set arbitrarily as long as the effects of the present invention are not markedly impaired. The molecular weight of the diisocyanate compound is usually 80 or higher, preferably 115 or higher, more preferably 170 or higher, but usually 300 or lower, preferably 230 or lower. When the molecular weight is in this range, the solubility of the diisocyanate compound in the nonaqueous electrolyte solution is likely to be ensured, so that the effects of the present invention are likely to be expressed.

Specific examples of the diisocyanate compound include:
cycloalkane ring-containing diisocyanates, such as 1,2-diisocyanatocyclopentane, 1,3-diisocyanatocyclopentane, 1,2-diisocyanatocyclohexane, 1,3-diisocyanatocyclohexane, 1,4-diisocyanatocyclohexane, 1,2-bis(isocyanatomethyl)cyclohexane, 1,3-bis(isocyanatomethyl)cyclohexane, 1,4-bis(isocyanatomethyl)cyclohexane, dicyclohexylmethane-2,2'-diisocyanate, dicyclohexylmethane-2,4'-diisocyanate, dicyclohexylmethane-3,3'-diisocyanate, and dicyclohexylmethane-4,4'-diisocyanate; and aromatic ring-containing diisocyanates, such as 1,2-phenylene diisocyanate, 1,3-phenylene diisocyanate, 1,4-phenylene diisocyanate, tolylene-2,3-diisocyanate, tolylene-2,4-diisocyanate, tolylene-2,5-diisocyanate, tolylene-2,6-diisocyanate, tolylene-3,4-diisocyanate, tolylene-3,5-diisocyanate, 1,2-bis(isocyanatomethyl)benzene, 1,3-bis(isocyanatomethyl)benzene, 1,4-bis(isocyanatomethyl)benzene, 2,4-diisocyanatobiphenyl, 2,6-diisocyanatobiphenyl, 2,2'-diisocyanatobiphenyl, 3,3'-diisocyanatobiphenyl, 4,4'-diisocyanato-2-methylbiphenyl, 4,4'-diisocyanato-3-methylbiphenyl, 4,4'-diisocyanato-3,3'-dimethylbiphenyl, 4,4'-diisocyanatodiphenylmethane, 4,4'-diisocyanato-2-methyldiphenylmethane, 4,4'-diisocyanato-3-methyldiphenylmethane, 4,4'-diisocyanato-3,3'-dimethyldiphenylmethane, 1,5-diisocyanatonaphthalene, 1,8-diisocyanatonaphthalene, 2,3-diisocyanatonaphthalene, 1,5-bis(isocyanatomethyl)naphthalene, 1,8-bis(isocyanatomethyl)naphthalene, and 2,3-bis(isocyanatomethyl)naphthalene.

Thereamong, 1,2-diisocyanatocyclopentane, 1,3-diisocyanatocyclopentane, 1,2-diisocyanatocyclohexane, 1,3-diisocyanatocyclohexane, 1,4-diisocyanatocyclohexane, 1,2-bis(isocyanatomethyl)cyclohexane, 1,3-bis(isocyanatomethyl)cyclohexane, 1,4-bis(isocyanatomethyl)cyclohexane, 1,2-phenylene diisocyanate, 1,3-phenylene diisocyanate, 1,4-phenylene diisocyanate, 1,2-bis(isocyanatomethyl)benzene, 1,3-bis(isocyanatomethyl)benzene, 1,4-bis(isocyanatomethyl)benzene, 2,4-diisocyanatobiphenyl, and 2,6-diisocyanatobiphenyl are preferred since these diisocyanate compounds form a more compact composite coating film on a negative electrode, and the battery durability is consequently improved.

Among these diisocyanate compounds, 1,3-bis(isocyanatomethyl)cyclohexane, 1,4-bis(isocyanatomethyl)cyclohexane, 1,3-phenylene diisocyanate, 1,4-phenylene diisocyanate, 1,2-bis(isocyanatomethyl)benzene, 1,3-bis(isocyanatomethyl)benzene, and 1,4-bis(isocyanatomethyl)benzene are more preferred since these diisocyanate compounds, because of their molecular symmetry, form a coating film advantageous for lithium ion conductivity on a negative electrode, and the battery characteristics are consequently further improved.

Any of the above-described diisocyanate compounds may be used singly, or two or more thereof may be used in any combination at any ratio.

The content of the diisocyanate compound(s) that can be used in the nonaqueous electrolyte solution of the present embodiment is not particularly restricted and may be set arbitrarily as long as the effects of the present invention are not markedly impaired; however, it is usually 0.001% by mass or higher, preferably 0.01% by mass or higher, more preferably 0.1% by mass or higher, still more preferably 0.3% by mass or higher, but usually 5% by mass or less, preferably 4% by mass or less, more preferably 3% by mass or less, still more preferably 2% by mass or less, with respect to the amount of the nonaqueous electrolyte solution of the present embodiment. When the content of the diisocyanate compound(s) is in this range, the durability in cycle operation, storage and the like can be improved, so that the effects of the present invention can be sufficiently exerted.

A method of producing the diisocyanate compound is not particularly restricted, and any known method can be selected to produce the diisocyanate compound. Further, a commercially available product may be used as well.

<2-4-5-2. Isocyanate Compound Other than Diisocyanate Compound>

The nonaqueous electrolyte solution of the present embodiment may also contain an isocyanate compound other than a diisocyanate compound. The isocyanate compound other than a diisocyanate compound that can be used in the nonaqueous electrolyte solution of the present embodiment will now be described referring to specific examples.

Specific examples of the isocyanate compound include:

hydrocarbon-based monoisocyanate compounds, such as methyl isocyanate, ethyl isocyanate, propyl isocyanate, isopropyl isocyanate, butyl isocyanate, t-butyl isocyanate, pentyl isocyanate, hexyl isocyanate, cyclohexyl isocyanate, phenyl isocyanate, and fluorophenyl isocyanate;

monoisocyanate compounds having a carbon-carbon unsaturated bond, such as vinyl isocyanate, allyl isocyanate, ethynyl isocyanate, and propynyl isocyanate; and isocyanate compounds, such as (ortho-, meta-, or para-) toluenesulfonyl isocyanate, benzenesulfonyl isocyanate, fluorosulfonyl isocyanate, phenoxysulfonyl isocyanate, pentafluorophenoxysulfonyl isocyanate, and methoxysulfonyl isocyanate.

Any of the above-described isocyanate compounds may be used singly, or two or more thereof may be used in any combination at any ratio.

The amount of the isocyanate compound(s) to be incorporated with respect to the whole nonaqueous electrolyte solution of the present embodiment is not restricted and may be set arbitrarily as long as the effects of the present invention are not markedly impaired; however, the isocyanate compound(s) is/are incorporated into the nonaqueous electrolyte solution of the present embodiment in an amount of usually 0.001% by mass or greater, preferably 0.01% by mass or greater, more preferably 0.1% by mass or greater, but usually 10% by mass or less, preferably 5% by mass or less, more preferably 3% by mass or less, still more preferably 2% by mass or less, particularly preferably 1% by mass or less, most preferably 0.5% by mass or less. When the content of the isocyanate compound(s) is in this range, the durability in cycle operation, storage and the like can be improved, so that the effects of the present invention can be sufficiently exerted.

A method of producing the isocyanate compound is not particularly restricted, and any known method can be selected to produce the isocyanate compound. Further, a commercially available product may be used as well.

<2-4-6. Carboxylic Acid Anhydride>

As a carboxylic acid anhydride that can be used in the nonaqueous electrolyte solution of the present embodiment, a compound represented by the following Formula (6) is preferred. A method of producing the carboxylic acid anhydride is not particularly restricted, and any known method can be selected to produce the carboxylic acid anhydride.

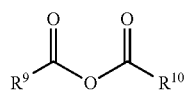

(6)

(In Formula (6), $R^9$ and $R^{10}$ each independently represent a hydrocarbon group having 1 to 15 carbon atoms which optionally has a substituent; and $R^9$ and $R^{10}$ are optionally bound with each other to form a cyclic structure.)

The types of $R^9$ and $R^{10}$ are not particularly restricted as long as they are monovalent hydrocarbon groups. For example, $R^9$ and $R^{10}$ may each be an aliphatic hydrocarbon group, an aromatic hydrocarbon group, or a group constituted by an aliphatic hydrocarbon group and an aromatic hydrocarbon group that are bound with each other. The aliphatic hydrocarbon group may be a saturated hydrocarbon group, or may contain an unsaturated bond (a carbon-carbon double bond or a carbon-carbon triple bond). In addition, the aliphatic hydrocarbon group may be open-chain or cyclic and, when the aliphatic hydrocarbon group is open-chain, it may have a straight chain or a branched chain. Further, the aliphatic hydrocarbon group may be constituted by an open-chain group and a cyclic group that are bound with each other. It is noted here that $R^9$ and $R^{10}$ may be the same or different from each other.

When $R^9$ and $R^{10}$ are bound with each other to form a cyclic structure, the hydrocarbon group constituted by $R^9$ and $R^{10}$ that are bound with each other is divalent. The type of this divalent hydrocarbon group is not particularly restricted. In other words, the divalent hydrocarbon group may be an aliphatic group, an aromatic group, or a group constituted by an aliphatic group and an aromatic group that are bound with each other. When the divalent hydrocarbon group is an aliphatic group, it may be a saturated group or an unsaturated group. In addition, the aliphatic group may be an open-chain group or a cyclic group and, when the aliphatic group is an open-chain group, it may be a straight-chain group or a branched-chain group. Further, the aliphatic group may be constituted by an open-chain group and a cyclic group that are bound with each other.

When the hydrocarbon groups of $R^9$ and $R^{10}$ have a substituent, the type of the substituent is not particularly restricted unless it conflicts with the gist of the present invention, and examples of the substituent include halogen atoms such as a fluorine atom, a chlorine atom, a bromine atom, and an iodine atom, among which a fluorine atom is preferred. Examples of the substituent other than a halogen atom include substituents having a functional group, such as an ester group, a cyano group, a carbonyl group and an ether group, among which a cyano group and a carbonyl group are preferred. The hydrocarbon groups of $R^9$ and $R^{10}$ may have only one of these substituents, or may have two or more of these substituents. When the hydrocarbon groups of $R^9$ and $R^{10}$ have two or more substituents, these substituents may be the same or different from one another.

The number of carbon atoms in each hydrocarbon group of $R^9$ and $R^{10}$ is usually 1 or more, but usually 15 or less, preferably 12 or less, more preferably 10 or less, still more preferably 9 or less. When $R^9$ and $R^{10}$ are bound with each other to form a divalent hydrocarbon group, the number of carbon atoms of the divalent hydrocarbon group is usually 1 or more, but usually 15 or less, preferably 13 or less, more preferably 10 or less, still more preferably 8 or less. It is noted here that, when each hydrocarbon group of $R^9$ and $R^{10}$ has a carbon atom-containing substituent, the total number of carbon atoms of $R^9$ and $R^{10}$ including the substituent preferably satisfy the above-described range.

Next, specific examples of the acid anhydride represented by Formula (6) (hereinafter, may also be simply referred to as "acid anhydride") will be described. In the following examples, the term "analogue" refers to an acid anhydride obtained by replacing a part of the structure of an exemplified acid anhydride with another structure within a range that does not conflict with the gist of the present invention, and examples thereof include: dimers, trimers and tetramers that are constituted by plural acid anhydrides; structural isomers that have the same number of carbon atoms of a substituent but have a branched chain; and acid anhydrides in which a substituent binds at different sites.

First, specific examples of the acid anhydride wherein $R^9$ and $R^{10}$ are the same will be described.

Specific examples of the acid anhydride wherein $R^9$ and $R^{10}$ are both an open-chain alkyl group include acetic acid anhydride, propionic acid anhydride, butanoic acid anhydride, 2-methylpropionic acid anhydride, 2,2-dimethylpropionic acid anhydride, 2-methylbutanoic acid anhydride, 3-methylbutanoic acid anhydride, 2,2-dimethylbutanoic acid anhydride, 2,3-dimethylbutanoic acid anhydride, 3,3-dimethylbutanoic acid anhydride, 2,2,3-trimethylbutanoic acid anhydride, 2,3,3-trimethylbutanoic acid anhydride, 2,2,3,3-teramethylbutanoic acid anhydride, and 2-ethylbutanoic acid anhydride, as well as analogues of these acid anhydrides.

Specific examples of the acid anhydride wherein $R^9$ and $R^{10}$ are both a cyclic alkyl group include cyclopropane carboxylic acid anhydride, cyclopentane carboxylic acid anhydride, and cyclohexane carboxylic acid anhydride, as well as analogues of these acid anhydrides.

Specific examples of the acid anhydride wherein $R^9$ and $R^{10}$ are both an alkenyl group include acrylic acid anhydride, 2-methylacrylic acid anhydride, 3-methylacrylic acid anhydride, 2,3-dimethylacrylic acid anhydride, 3,3-dimethylacrylic acid anhydride, 2,3,3-trimethylacrylic acid anhydride, 2-phenylacrylic acid anhydride, 3-phenylacrylic acid anhydride, 2,3-diphenylacrylic acid anhydride, 3,3-diphenylacrylic acid anhydride, 3-butenoic acid anhydride, 2-methyl-3-butenoic acid anhydride, 2,2-dimethyl-3-butenoic acid anhydride, 3-methyl-3-butenoic acid anhydride, 2-methyl-3-methyl-3-butenoic acid anhydride, 2,2-dimethyl-3-methyl-3-butenoic acid anhydride, 3-pentenoic acid anhydride, 4-pentenoic acid anhydride, 2-cyclopentenecarboxylic acid anhydride, 3-cyclopentenecarboxylic acid anhydride, and 4-cyclopentenecarboxylic acid anhydride, as well as analogues of these acid anhydrides.

Specific examples of the acid anhydride wherein $R^9$ and $R^{10}$ are both an alkynyl group include propynoic acid anhydride, 3-phenylpropynoic acid anhydride, 2-butynoic acid anhydride, 2-pentynoic acid anhydride, 3-butynoic acid anhydride, 3-pentynoic acid anhydride, and 4-pentynoic acid anhydride, as well as analogues of these acid anhydrides.

Specific examples of the acid anhydride wherein $R^9$ and $R^{10}$ are both an aryl group include benzoic acid anhydride, 4-methylbenzoic acid anhydride, 4-ethylbenzoic acid anhydride, 4-tert-butylbenzoic acid anhydride, 2-methylbenzoic acid anhydride, 2,4,6-trimethylbenzoic acid anhydride, 1-naphthalenecarboxylic acid anhydride, and 2-naphthalenecarboxylic acid anhydride, as well as analogues of these acid anhydrides.

Further, as examples of the acid anhydride wherein $R^9$ and $R^{10}$ are both substituted with a halogen atom, acid anhydrides wherein $R^9$ and $R^{10}$ are both substituted with a fluorine atom are mainly exemplified below; however, the exemplified compounds also encompass those acid anhydrides obtained by substituting some or all of their fluorine atoms with a chlorine atom, a bromine atom or an iodine atom.

Examples of the acid anhydride wherein $R^9$ and $R^{10}$ are both an open-chain alkyl group substituted with a halogen atom include fluoroacetic acid anhydride, difluoroacetic acid anhydride, trifluoroacetic acid anhydride, 2-fluoropropionic acid anhydride, 2,2-difluoropropionic acid anhydride, 2,3-difluoropropionic acid anhydride, 2,2,3-trifluoropropionic acid anhydride, 2,3,3-trifluoropropionic acid anhydride, 2,2,3,3-tetrafluoropropionic acid anhydride, 2,3,3,3-tetrafluoropropionic acid anhydride, 3-fluoropropionic acid anhydride, 3,3-difluoropropionic acid anhydride, 3,3,3-trifluoropropionic acid anhydride, and perfluoropropionic acid anhydride, as well as analogues of these acid anhydrides.

Examples of the acid anhydride wherein $R^9$ and $R^{10}$ are both a cyclic alkyl group substituted with a halogen atom include 2-fluorocyclopentanecarboxylic acid anhydride, 3-fluorocyclopentanecarboxylic acid anhydride, and 4-fluorocyclopentanecarboxylic acid anhydride, as well as analogues of these acid anhydrides.

Examples of the acid anhydride wherein $R^9$ and $R^{10}$ are both an alkenyl group substituted with a halogen atom include 2-fluoroacrylic acid anhydride, 3-fluoroacrylic acid anhydride, 2,3-difluoroacrylic acid anhydride, 3,3-difluoroacrylic acid anhydride, 2,3,3-trifluoroacrylic acid anhydride, 2-(trifluoromethyl)acrylic acid anhydride, 3-(trifluoromethyl)acrylic acid anhydride, 2,3-bis(trifluoromethyl)acrylic acid anhydride, 2,3,3-tris(trifluoromethyl)acrylic acid anhydride, 2-(4-fluorophenyl)acrylic acid anhydride, 3-(4-fluorophenyl)acrylic acid anhydride, 2,3-bis(4-fluorophenyl)acrylic acid anhydride, 3,3-bis(4-fluorophenyl)acrylic acid anhydride, 2-fluoro-3-butenoic acid anhydride, 2,2-difluoro-3-butenoic acid anhydride, 3-fluoro-2-butenoic acid anhydride, 4-fluoro-3-butenoic acid anhydride, 3,4-difluoro-3-butenoic acid anhydride, and 3,3,4-trifluoro-3-butenoic acid anhydride, as well as analogues of these acid anhydrides.

Examples of the acid anhydride wherein $R^9$ and $R^{10}$ are both an alkynyl group substituted with a halogen atom include 3-fluoro-2-propynoic acid anhydride, 3-(4-fluorophenyl)-2-propynoic acid anhydride, 3-(2,3,4,5,6-pentafluorophenyl)-2-propynoic acid anhydride, 4-fluoro-2-butynoic acid anhydride, 4,4-difluoro-2-butynoic acid anhydride, and 4,4,4-trifluoro-2-butynoic acid anhydride, as well as analogues of these acid anhydrides.

Examples of the acid anhydride wherein $R^9$ and $R^{10}$ are both an aryl group substituted with a halogen atom include 4-fluorobenzoic acid anhydride, 2,3,4,5,6-pentafluorobenzoic acid anhydride, and 4-trifluoromethylbenzoic acid anhydride, as well as analogues of these acid anhydrides.

Examples of the acid anhydride wherein $R^9$ and $R^{10}$ both have a substituent containing a functional group, such as ester, a nitrile, a ketone or an ether, include methoxyformic acid anhydride, ethoxyformic acid anhydride, methyloxalic acid anhydride, ethyloxalic acid anhydride, 2-cyanoacetic acid anhydride, 2-oxopropionic acid anhydride, 3-oxobutanoic acid anhydride, 4-acetylbenzoic acid anhydride, methoxyacetic acid anhydride and 4-methoxybenzoic acid anhydride, as well as analogues of these acid anhydrides.

Next, specific examples of the acid anhydride wherein $R^9$ and $R^{10}$ are different from each other will be described.

As $R^9$ and $R^{10}$, all combinations of the above-described examples and analogues thereof are considered, and representative examples are described below.

Examples of a combination of open-chain alkyl groups include acetic propionic anhydride, acetic butanoic anhydride, butanoic propionic anhydride, and acetic 2-methylpropionic anhydride.

Examples of a combination of an open-chain alkyl group and a cyclic alkyl group include acetic cyclopentanoic anhydride, acetic cyclohexanoic anhydride, and cyclopentanoic propionic anhydride.

Examples of a combination of an open-chain alkyl group and an alkenyl group include acetic acrylic anhydride, acetic 3-methylacrylic anhydride, acetic 3-butenoic anhydride, and acrylic propionic anhydride.

Examples of a combination of an open-chain alkyl group and an alkynyl group include acetic propynoic anhydride, acetic 2-butynoic anhydride, acetic 3-butynoic anhydride, acetic 3-phenylpropynoic anhydride, and propionic propynoic anhydride.

Examples of a combination of an open-chain alkyl group and an aryl group include acetic benzoic anhydride, acetic 4-methylbenzoic anhydride, acetic 1-naphthalenecarboxylic anhydride, and benzoic propionic anhydride.

Examples of a combination of an open-chain alkyl group and a hydrocarbon group having a functional group include acetic fluoroacetic anhydride, acetic trifluoroacetic anhydride, acetic 4-fluorobenzoic anhydride, fluoroacetic propionic anhydride, acetic alkyloxalic anhydride, acetic 2-cyanoacetic anhydride, acetic 2-oxopropionic anhydride, acetic methoxyacetic anhydride, and methoxyacetic propionic anhydride.

Examples of a combination of cyclic alkyl groups include cyclopentanoic cyclohexanoic anhydride.

Examples of a combination of a cyclic alkyl group and an alkenyl group include acrylic cyclopentanoic anhydride, 3-methylacrylic cyclopentanoic anhydride, 3-butenoic cyclopentanoic anhydride, and acrylic cyclohexanoic anhydride.

Examples of a combination of a cyclic alkyl group and an alkynyl group include propynoic cyclopentanoic anhydride, 2-butynoic cyclopentanoic anhydride, and propynoic cyclohexanoic anhydride.

Examples of a combination of a cyclic alkyl group and an aryl group include benzoic cyclopentanoic anhydride, 4-methylbenzoic cyclopentanoic anhydride, and benzoic cyclohexanoic anhydride.

Examples of a combination of a cyclic alkyl group and a hydrocarbon group having a functional group include fluoroacetic cyclopentanoic anhydride, cyclopentanoic trifluoroacetic anhydride, cyclopentanoic 2-cyanoacetic anhydride, cyclopentanoic methoxyacetic anhydride, and cyclohexanoic fluoroacetic anhydride.

Examples of a combination of alkenyl groups include acrylic 2-methylacrylic anhydride, acrylic 3-methylacrylic anhydride, acrylic 3-butenoic anhydride, and 2-methylacrylic 3-methylacrylic anhydride.

Examples of a combination of an alkenyl group and an alkynyl group include acrylic propynoic anhydride, acrylic 2-butynoic anhydride, and 2-methylacrylic propynoic anhydride.

Examples of a combination of an alkenyl group and an aryl group include acrylic benzoic anhydride, acrylic 4-methylbenzoic anhydride, and 2-methylacrylic benzoic anhydride.

Examples of a combination of an alkenyl group and a hydrocarbon group having a functional group include acrylic fluoroacetic anhydride, acrylic trifluoroacetic anhydride, acrylic 2-cyanoacetic anhydride, acrylic methoxyacetic anhydride, and 2-methylacrylic fluoroacetic anhydride.

Examples of a combination of alkynyl groups include propynoic 2-butynoic anhydride, propynoic 3-butynoic anhydride, and 2-butynoic 3-butynoic anhydride.

Examples of a combination of an alkynyl group and an aryl group include benzoic propynoic anhydride, 4-methylbenzoic propynoic anhydride, and benzoic 2-butynoic anhydride.

Examples of a combination of an alkynyl group and a hydrocarbon group having a functional group include propynoic fluoroacetic anhydride, propynoic trifluoroacetic anhydride, propynoic 2-cyanoacetic anhydride, propynoic methoxyacetic anhydride, and 2-butynoic fluoroacetic anhydride.

Examples of a combination of aryl groups include benzoic 4-methylbenzoic anhydride, benzoic 1-naphthalenecarboxylic anhydride, and 4-methylbenzoic 1-naphthalenecarboxylic anhydride.

Examples of a combination of an aryl group and a hydrocarbon group having a functional group include benzoic fluoroacetic anhydride, benzoic trifluoroacetic anhydride, benzoic 2-cyanoacetic anhydride, benzoic methoxyacetic anhydride, and 4-methylbenzoic fluoroacetic anhydride.

Examples of a combination of hydrocarbon groups having a functional group include fluoroacetic trifluoroacetic anhydride, fluoroacetic 2-cyanoacetic anhydride, fluoroacetic methoxyacetic anhydride, and trifluoroacetic 2-cyanoacetic anhydride.

Among the above-described acid anhydrides having an open-chain structure, acetic acid anhydride, propionic acid anhydride, 2-methylpropionic acid anhydride, cyclopentanecarboxylic acid anhydride, cyclohexanecarboxylic acid anhydride, acrylic acid anhydride, 2-methylacrylic acid anhydride, 3-methylacrylic acid anhydride, 2,3-dimethylacrylic acid anhydride, 3,3-dimethylacrylic acid anhydride, 3-butenoic acid anhydride, 2-methyl-3-butenoic acid anhydride, propynoic acid anhydride, 2-butynoic acid anhydride, benzoic acid anhydride, 2-methylbenzoic acid anhydride, 4-methylbenzoic acid anhydride, 4-tert-butylbenzoic acid anhydride, trifluoroacetic acid anhydride, 3,3,3-trifluoropropionic acid anhydride, 2-(trifluoromethyl)acrylic acid anhydride, 2-(4-fluorophenyl)acrylic acid anhydride, 4-fluorobenzoic acid anhydride, 2,3,4,5,6-pentafluorobenzoic acid anhydride, methoxyformic acid anhydride, and ethoxyformic acid anhydride are preferred, and acrylic acid anhydride, 2-methylacrylic acid anhydride, 3-methylacrylic acid anhydride, benzoic acid anhydride, 2-methylbenzoic acid anhydride, 4-methylbenzoic acid anhydride, 4-tert-butylbenzoic acid anhydride, 4-fluorobenzoic acid anhydride, 2,3,4,5,6-pentafluorobenzoic acid anhydride, methoxyformic acid anhydride, and ethoxyformic acid anhydride are more preferred.

These compounds are preferred since they are capable of improving particularly the charge-discharge rate characteristics, the input-output characteristics and the impedance characteristics after a durability test by appropriately forming a bond with lithium oxalate and thereby generating a coating film having excellent durability.

Next, specific examples of the acid anhydride wherein $R^9$ and $R^{10}$ are bound with each other to form a cyclic structure will be described.

First, specific examples of the acid anhydride wherein $R^9$ and $R^{10}$ are bound with each other to form a 5-membered ring structure include succinic acid anhydride, 4-methylsuccinic acid anhydride, 4,4-dimethylsuccinic acid anhydride, 4,5-dimethylsuccinic acid anhydride, 4,4,5-trimethylsuccinic acid anhydride, 4,4,5,5-tetramethylsuccinic acid anhydride, 4-vinylsuccinic acid anhydride, 4,5-divinylsuccinic acid anhydride, 4-phenylsuccinic acid anhydride, 4,5-diphenylsuccinic acid anhydride, 4,4-diphenylsuccinic acid anhydride, citraconic acid anhydride, maleic acid anhydride, 4-methylmaleic acid anhydride, 4,5-dimethylmaleic acid anhydride, 4-phenylmaleic acid anhydride, 4,5-diphenylmaleic acid anhydride, itaconic acid anhydride, 5-methylitaconic acid anhydride, 5,5-dimethylitaconic acid anhydride, phthalic acid anhydride, and 3,4,5,6-tetrahydrophthalic acid anhydride, as well as analogues of these acid anhydrides.

Specific examples of the acid anhydride wherein $R^9$ and $R^{10}$ are bound with each other to form a 6-membered ring structure include cyclohexane-1,2-dicarboxylic acid anhydride, 4-cyclohexene-1,2-dicarboxylic acid anhydride, and glutaric acid anhydride, as well as analogues of these acid anhydrides.

Specific examples of the acid anhydride wherein $R^9$ and $R^{10}$ are bound with each other to form other cyclic structure include 5-norbornene-2,3-dicarboxylic acid anhydride, cyclopentanetetracarboxylic acid dianhydride, pyromellitic anhydride, and diglycolic acid anhydride, as well as analogues of these acid anhydrides.

Specific examples of the acid anhydride wherein $R^9$ and $R^{10}$ are bound with each other to form other cyclic structure and substituted with a halogen atom include 4-fluorosuccinic acid anhydride, 4,4-difluorosuccinic acid anhydride, 4,5-difluorosuccinic acid anhydride, 4,4,5-trifluorosuccinic acid anhydride, 4,4,5,5-tetrafluorosuccinic acid anhydride, 4-fluoromaleic acid anhydride, 4,5-difluoromaleic acid anhydride, 5-fluoroitaconic acid anhydride, and 5,5-difluoroitaconic acid anhydride, as well as analogues of these acid anhydrides.

Among the above-described acid anhydrides wherein $R^9$ and $R^{10}$ are bound with each other, succinic acid anhydride, 4-methylsuccinic acid anhydride, 4-vinylsuccinic acid anhydride, 4-phenylsuccinic acid anhydride, citraconic acid anhydride, maleic acid anhydride, 4-methylmaleic acid anhydride, 4-phenylmaleic acid anhydride, itaconic acid anhydride, 5-methylitaconic acid anhydride, glutaric acid anhydride, phthalic acid anhydride, cyclohexane-1,2-dicarboxylic acid anhydride, 5-norbornene-2,3-dicarboxylic acid anhydride, cyclopentanetetracarboxylic acid dianhydride, pyromellitic acid anhydride, 4-fluorosuccinic acid anhydride, 4-fluoromaleic acid anhydride, and 5-fluoroitaconic acid anhydride are preferred, and succinic acid anhydride, 4-methylsuccinic acid anhydride, 4-vinylsuccinic acid anhydride, citraconic acid anhydride, cyclohexane-1,2-dicarboxylic acid anhydride, 5-norbornene-2,3-dicarboxylic acid anhydride, cyclopentanetetracarboxylic acid dianhydride, pyromellitic acid anhydride, and 4-fluorosuccinic acid anhydride are more preferred. These compounds are preferred since they particularly improve the capacity retention rate after a durability test by appropriately forming a bond with lithium oxalate and thereby generating a coating film having excellent durability.

The molecular weight of the carboxylic acid anhydride is not restricted and may be set arbitrarily as long as the effects of the present invention are not markedly impaired; however, it is usually 90 or higher, preferably 95 or higher, but usually 300 or lower, preferably 200 or lower. When the molecular weight of the carboxylic acid anhydride is in this range, an increase in the viscosity of the electrolyte solution can be inhibited and the coating film density is optimized, so that the durability can be appropriately improved.

A method of producing the carboxylic acid anhydride is also not particularly restricted, and any known method can be selected to produce the carboxylic acid anhydride. In the nonaqueous electrolyte solution of the present embodiment, any of the above-exemplified carboxylic acid anhydrides may be incorporated singly, or two or more thereof may be incorporated in any combination at any ratio.

The content of the carboxylic acid anhydride(s) in the nonaqueous electrolyte solution of the present embodiment is not particularly restricted and may be set arbitrarily as long as the effects of the present invention are not markedly impaired; however, in the nonaqueous electrolyte solution of the present invention, the carboxylic acid anhydride(s) is/are desirably incorporated at a concentration of usually 0.01% by mass or higher, preferably 0.1% by mass or higher, but usually 5% by mass or lower, preferably 3% by mass or lower. When the content of the carboxylic acid anhydride(s) is in this range, a cycle characteristics-improving effect is likely to be expressed and a suitable reactivity is attained; therefore, the battery characteristics are likely to be improved.

<2-4-7. Overcharge Inhibitor>

In the nonaqueous electrolyte solution of the present embodiment, an overcharge inhibitor can be used for the purpose of effectively inhibiting rupture and ignition of the nonaqueous electrolyte secondary battery in an overcharged state and the like.

Examples of the overcharge inhibitor include: aromatic compounds, such as biphenyl, alkylbiphenyls, terphenyl, partially hydrogenated terphenyl, cyclohexylbenzene, t-butylbenzene, t-amylbenzene, diphenyl ether, dibenzofuran, diphenylcyclohexane, and 1,1,3-trimethyl-3-phenylindane; partially fluorinated products of these aromatic compounds, such as 2-fluorobiphenyl, o-cyclohexylfluorobenzene, and p-cyclohexylfluorobenzene; fluorine-containing anisole compounds, such as 2,4-difluoroanisole, 2,5-difluoroanisole, 2,6-difluoroanisole, and 3,5-difluoroanisole; aromatic acetates, such as 3-propylphenyl acetate, 2-ethylphenyl acetate, benzylphenyl acetate, methylphenyl acetate, benzyl acetate, and phenethylphenyl acetate; and aromatic carbonates, such as diphenyl carbonate and methylphenyl carbonate. Thereamong, biphenyl, alkylbiphenyls, terphenyl, partially hydrogenated terphenyl, cyclohexylbenzene, t-butylbenzene, t-amylbenzene, diphenyl ether, dibenzofuran, diphenylcyclohexane, 1,1,3-trimethyl-3-phenylindane, 3-propylphenyl acetate, 2-ethylphenyl acetate, benzylphenyl acetate, methylphenyl acetate, benzyl acetate, phenethylphenyl acetate, diphenyl carbonate, and methylphenyl carbonate are preferred. These overcharge inhibitors may be used singly, or in combination of two or more thereof. In the case of using two or more overcharge inhibitors in combination, from the standpoint of the balance between the overcharge-inhibiting properties and the high-temperature storage characteristics, it is particularly preferred to use a combination of cyclohexylbenzene and t-butylbenzene or t-amylbenzene, or a combination of at least one selected from oxygen-free aromatic compounds, such as biphenyl, alkylbiphenyls, terphenyl, partially hydrogenated terphenyl, cyclohexylbenzene, t-butylbenzene and t-amylbenzene, and at least one selected from oxygen-containing aromatic compounds, such as diphenyl ether and dibenzofuran.

The content of the overcharge inhibitor is not particularly restricted and may be set arbitrarily as long as the effects of the present invention are not markedly impaired. The content of the overcharge inhibitor is usually 0.1% by mass or higher, preferably 0.2% by mass or higher, more preferably 0.3% by mass or higher, still more preferably 0.5% by mass or higher, but usually 5% by mass or less, preferably 4.8% by mass or less, more preferably 4.5% by mass or less, in 100% by mass of the nonaqueous electrolyte solution. When the content of the overcharge inhibitor is in this range, the effect of the overcharge inhibitor is likely to be expressed sufficiently, and the battery characteristics such as high-temperature storage characteristics are improved.

<2-4-8. Other Auxiliary Agents>

In the nonaqueous electrolyte solution of the present embodiment, a known other auxiliary agent(s) can be used. Examples of such auxiliary agents include:

carbonate compounds, such as erythritan carbonate, spiro-bis-dimethylene carbonate, and methoxyethyl methyl carbonate;

triple bond-containing compounds, such as methyl-2-propynyl oxalate, ethyl-2-propynyl oxalate, bis(2-propynyl) oxalate, 2-propynyl acetate, 2-propynyl formate, 2-propynyl methacrylate, di(2-propynyl)glutarate, methyl-2-propynyl carbonate, ethyl-2-propynyl carbonate, bis(2-propynyl)carbonate, 2-butyne-1,4-diyl-dimethane sulfonate, 2-butyne-1,4-diyl-diethane sulfonate, 2-butyne-1,4-diyl-diformate, 2-butyne-1,4-diyl-di acetate, 2-butyne-1,4-diyl-dipropionate, 4-hexadiyne-1,6-diyl-dimethane sulfonate, 2-propynyl-methane sulfonate, 1-methyl-2-propynyl-methane sulfonate, 1,1-dimethyl-2-propynyl-methane sulfonate, 2-propynyl-ethane sulfonate, 2-propynyl-vinyl sulfonate, 2-propynyl-2-(diethoxyphosphoryl)acetate, 1-methyl-2-propynyl-2-(diethoxyphosphoryl)acetate, and 1,1-dimethyl-2-propynyl-2-(diethoxyphosphoryl)acetate;

spiro compounds, such as 2,4,8,10-tetraoxaspiro[5.5]undecane and 3,9-divinyl-2,4,8,10-tetraoxaspiro[5.5]undecane;

sulfur-containing compounds, such as ethylene sulfite, methyl fluorosulfonate, ethyl fluorosulfonate, methyl methanesulfonate, ethyl methanesulfonate, busulfan, sulfolene, diphenyl sulfone, N,N-dimethylmethane sulfonamide, N,N-diethylmethane sulfonamide, trimethylsilyl methyl sulfate, trimethylsilyl ethyl sulfate, and 2-propynyl-trimethylsilyl sulfate;

isocyanate compounds, such as 2-isocyanatoethyl acrylate, 2-isocyanatoethyl methacrylate, 2-isocyanatoethyl crotonate, 2-(2-isocyanatoethoxy)ethyl acrylate, 2-(2-isocyanatoethoxy)ethyl methacrylate, and 2-(2-isocyanatoethoxy)ethyl crotonate;

nitrogen-containing compounds, such as 1-methyl-2-pyrrolidinone, 1-methyl-2-piperidone, 3-methyl-2-oxazolidinone, 1,3-dimethyl-2-imidazolidinone, and N-methyl succinimide;

hydrocarbon compounds, such as heptane, octane, nonane, decane, and cycloheptane;

fluorine-containing aromatic compounds, such as fluorobenzene, difluorobenzene, hexafluorobenzene, benzotrifluoride, pentafluorophenylmethane sulfonate, pentafluorophenyl trifluoromethane sulfonate, pentafluorophenyl acetate, pentafluorophenyl trifluoroacetate, and methylpentafluorophenyl carbonate;

silane compounds, such as tris(trimethyl silyl)borate, tris (trimethoxysilyl)borate, tris(trimethyl silyl)phosphate, tris (trimethoxysilyl)phosphate, dimethoxyaluminoxytrimethoxysilane, diethoxyaluminoxytriethoxysilane, dipropoxyaluminoxytriethoxysilane, dibutoxyaluminoxytrimethoxysilane, dibutoxyaluminoxytriethoxysilane, titanium tetrakis(trimethylsiloxide), and titanium tetrakis(triethylsiloxide);

ester compounds, such as 2-propynyl 2-(methanesulfonyloxy)propionate, 2-methyl 2-(methanesulfonyloxy)propionate, 2-ethyl 2-(methanesulfonyloxy)propionate, 2-propynyl methanesulfonyloxyacetate, 2-methyl methanesulfonyloxyacetate, and 2-ethyl methanesulfonyl oxyacetate; and lithium salts, such as lithium ethylmethyloxycarbonyl phosphonate, lithium ethylethyloxycarbonyl phosphonate, lithium ethyl-2-propynyl oxycarbonyl phosphonate, lithium ethyl-1-methyl-2-propynyloxycarbonyl phosphonate, and lithium ethyl-1,1-dimethyl-2-propynyloxycarbonyl phosphonate. These other auxiliary agents may be used singly, or in combination of two or more thereof. By adding these auxiliary agents, the capacity retention characteristics after high-temperature storage and the cycle characteristics can be improved.

The content of the other auxiliary agent(s) is not particularly restricted and may be set arbitrarily as long as the effects of the present invention are not markedly impaired. The content of the other auxiliary agent(s) is usually 0.01% by mass or higher, preferably 0.1% by mass or higher, more preferably 0.2% by mass or higher, but usually 5% by mass or less, preferably 3% by mass or less, more preferably 1% by mass or less, in 100% by mass of the nonaqueous electrolyte solution. When the content of the other auxiliary agent(s) is in this range, the effects of the other auxiliary agent(s) are likely to be expressed sufficiently, so that the battery characteristics such as high-load discharge characteristics are likely to be improved.

The nonaqueous electrolyte solution described above also encompasses nonaqueous electrolyte solutions that exist inside an energy device, such as the nonaqueous electrolyte secondary battery according to one embodiment of the present invention. Specifically, the present invention encompasses: a case where the nonaqueous electrolyte solution is a nonaqueous electrolyte solution existing inside a nonaqueous electrolyte secondary battery that is obtained by preparing the nonaqueous electrolyte solution from its constituents separately synthesized and substantially isolated, such as a lithium salt, a solvent and auxiliary agents, and subsequently injecting the nonaqueous electrolyte solution into a battery separately assembled by the below-described method; a case where the constituents of the nonaqueous electrolyte solution of the present embodiment, which have been separately placed in a nonaqueous electrolyte secondary battery in advance, are mixed in the battery and the same composition as the nonaqueous electrolyte solution of the present embodiment is thereby obtained; and a case where compounds constituting the nonaqueous electrolyte solution of the present embodiment are generated inside the nonaqueous electrolyte secondary battery to obtain the same composition as the nonaqueous electrolyte solution of the invention.

<2-5. Method of Producing Nonaqueous Electrolyte Solution>

The nonaqueous electrolyte solution of the present embodiment can be prepared by dissolving an electrolyte, compounds represented by Formulae (a1) and (a2) and, as required, the above-described "auxiliary agents" and other components, in the above-described nonaqueous solvent.

In the preparation of the nonaqueous electrolyte solution, raw materials of the nonaqueous electrolyte solution, namely the electrolyte such a lithium salt, compounds represented by Formulae (a1) and (a2), nonaqueous solvent, auxiliary agents and the like, are preferably dehydrated in advance. As for the degree of this dehydration, it is desired that the dehydration is performed to a moisture content of usually 50 ppm or less, preferably 30 ppm or less.

By removing water from the nonaqueous electrolyte solution, for example, electrolysis of water, reaction between water and the lithium metal, and hydrolysis of the lithium salt are made less likely to occur. The means for performing the dehydration is not particularly restricted and, for example, a drying agent such as a molecular sieve may be used when a liquid such as a nonaqueous solvent is to be dehydrated. Meanwhile, when a solid such as an electrolyte is to be dehydrated, the solid may be heat-dried at a temperature lower than the temperature at which the solid is decomposed.

3. Energy Device Using Nonaqueous Electrolyte Solution

An energy device using the nonaqueous electrolyte solution of the first or the second embodiment of the present invention includes: plural electrodes each capable of absorbing or releasing metal ions; and the above-described nonaqueous electrolyte solution of the present invention. Specific examples of the type of the energy device include primary batteries, secondary batteries, and metal ion capacitors such as lithium ion capacitors. Thereamong, the energy device is preferably a primary battery or a secondary battery, particularly preferably a secondary battery. The nonaqueous electrolyte solution used in the energy device is preferably a so-called gel electrolyte that is pseudo-solidified with a polymer, a filler or the like. The energy device will now be described.

<3-1. Nonaqueous Electrolyte Secondary Battery>
<3-1-1. Battery Configuration>

The nonaqueous electrolyte secondary batteries according to the first and the second embodiments of the present invention (hereinafter, these batteries are each also referred to as "the nonaqueous electrolyte secondary battery of the present invention") have the same configuration as that of a conventionally known nonaqueous electrolyte secondary battery, except for the nonaqueous electrolyte solution. The nonaqueous electrolyte secondary batteries usually have a form in which a positive electrode and a negative electrode are laminated via a porous membrane (separator) impregnated with the nonaqueous electrolyte solution of the present invention, and these components are housed in a casing (outer package). Accordingly, the shape of the nonaqueous electrolyte secondary battery of the present invention is not particularly restricted and may be any of, for example, a cylindrical shape, a prismatic shape, a laminated shape, a coin shape and a large-sized shape.

<3-1-2. Nonaqueous Electrolyte Solution>

As the nonaqueous electrolyte solution, the above-described nonaqueous electrolyte solution of the present invention is used. It is noted here, however, that the above-described nonaqueous electrolyte solution of the present invention can also be mixed with other nonaqueous electrolyte solution within a range that does not depart from the gist of the present invention.

<3-1-3. Negative Electrode>

The negative electrode active material used in the negative electrode is not particularly restricted as long as it is capable of electrochemically absorbing and releasing metal ions. Specific examples thereof include carbonaceous materials, metal compound-based materials and lithium-containing metal composite oxide materials, and any of these materials may be used singly, or two or more thereof may be used in any combination.

Thereamong, carbonaceous materials and metal compound-based materials are preferred and, among metal compound-based materials, silicon-containing materials are preferred. Accordingly, the negative electrode active material is particularly preferably a carbonaceous material or a silicon-containing material.

<3-1-3-1. Carbonaceous Material>

The carbonaceous material used as the negative electrode active material is not particularly restricted; however, it is preferably one selected from the following (A) to (D) from the standpoint of imparting the secondary battery with a good balance of the initial irreversible capacity and the high-current-density charge-discharge characteristics:

(A) natural graphite;
(B) a carbonaceous material obtained by heat-treating an artificial carbonaceous substance and an artificial graphitic substance in a range of 400° C. to 3,200° C. one or more times;
(C) a carbonaceous material yielding a negative electrode active material layer that is composed of at least two carbonaceous substances different in crystallinity and/or has an interface where the carbonaceous substances different in crystallinity are in contact with each other; and
(D) a carbonaceous material yielding a negative electrode active material layer that is composed of at least two carbonaceous substances different in orientation and/or has an interface where the carbonaceous substances different in orientation are in contact with each other.

Any of these carbonaceous materials (A) to (D) may be used singly, or two or more thereof may be used in any combination at any ratio.

Specific examples of the artificial carbonaceous substance or the artificial graphitic substance in the above-described (B) include: coal-based coke, petroleum coke; coal-based pitch, petroleum pitch, and oxidation products thereof;

needle coke, pitch coke, and carbon materials obtained by partial graphitization of these cokes;

pyrolysis products of organic substances, such as furnace black, acetylene black, and pitch-based carbon fibers;

carbonizable organic substances and carbonization products thereof; and solution-form carbides obtained by dissolving a carbonizable organic substance in a low-molecular-weight organic solvent, such as benzene, toluene, xylene, quinoline, or n-hexane.

All of the above-described carbonaceous materials (A) to (D) are conventionally known. The production methods thereof are well-known by those of ordinary skill in the art, and commercially available products of these materials can be purchases as well.

<3-1-3-2. Metal Compound-Based Material>

The metal compound-based material used as the negative electrode active material is not particularly restricted as long as it is capable of absorbing and releasing lithium ions, and, a metal or alloy that forms an alloy with lithium, or any compound thereof such as an oxide, a carbide, a nitride, a silicide, a sulfide or a phosphide can be used. Examples of such a metal compound include compounds that contain a metal such as Ag, Al, Ba, Bi, Cu, Ga, Ge, In, Ni, P, Pb, Sb, Si, Sn, Sr, or Zn. Thereamong, the metal compound-based material is preferably a metal or alloy that forms an alloy with lithium, more preferably a material containing a metal or metalloid element of the periodic table Group 13 or 14 (i.e. excluding carbon; a metal and a metalloid are hereinafter collectively referred to as "metal"), still more preferably a single substance metal of silicon (Si), tin (Sn) or lead (Pb) (hereinafter, these three elements may be referred to as "SSP metal elements"), an alloy containing these metal atoms, or a compound of these metals (SSP metal elements), most preferably a silicon-containing compound. Any of these materials may be used singly, or two or more thereof may be used in any combination at any ratio.

<3-1-3-3. Lithium-Containing Metal Composite Oxide Material>

The lithium-containing metal composite oxide material used as the negative electrode active material is not particularly restricted as long as it is capable of absorbing and releasing lithium ions; however, it is preferably a lithium-containing composite metal oxide material that contains titanium, particularly preferably a composite oxide of lithium and titanium (hereinafter, may be simply referred to as "lithium-titanium composite oxide"). In other words, it is particularly preferred to incorporate a lithium-titanium composite oxide having a spinel structure into the negative electrode active material for a lithium-ion nonaqueous electrolyte secondary battery, since the output resistance of the secondary battery is thereby greatly reduced.

In addition, a lithium-titanium composite oxide in which lithium or titanium is substituted with other metal element, such as at least one element selected from the group consisting of Na, K, Co, Al, Fe, Ti, Mg, Cr, Ga, Cu, Zn and Nb, is also preferred.

Examples of a lithium-titanium composite oxide preferred as the negative electrode active material include lithium-titanium composite oxides represented by the following composition formula (7):

$$Li_xTi_yM_zO_4 \qquad (7)$$

(wherein, M represents at least one element selected from the group consisting of Na, K, Co, Al, Fe, Ti, Mg, Cr, Ga, Cu, Zn, and Nb; and $0.7 \le x \le 1.5$, $1.5 \le y \le 2.3$ and $0 \le z \le 1.6$ are preferably satisfied since this makes the structure stable during doping and dedoping of lithium ions).

<3-1-3-4. Constitution, Physical Properties, and Preparation Method of Negative Electrode>

Known technical constitutions can be employed with regard to the negative electrode containing the above-described active material source, a method of producing the electrode, and a current collector; however, it is desired that one or more of the following items (i) to (vi) be satisfied at the same time.

(i) Production of Negative Electrode

For the production of the negative electrode, any known method can be employed as long as it does not markedly limit the effects of the present invention. For example, a binder, a solvent and, as required, a thickening agent, a conductive material, a filler and other components are added to the negative electrode active material to prepare a negative electrode-forming material in the form of a slurry, and this slurry is subsequently applied and dried onto a current collector, followed by pressing of the resultant, whereby a negative electrode active material layer can be formed.

(ii) Current Collector

As the current collector on which the negative electrode active material is retained, any known current collector can be used. Examples of the current collector of the negative electrode include metal materials such as aluminum, copper, nickel, stainless steel, and nickel-plated steel, among which copper is particularly preferred because of its processability and cost.

When the current collector is a metal material, the current collector may have any shape of, for example, a metal foil, a metal cylinder, a metal coil, a metal sheet, a metal thin film, an expanded metal, a punched metal, and a foamed metal. Thereamong, the current collector is preferably a metal thin film, more preferably a copper foil, still more preferably a rolled copper foil obtained by a rolling method or an electrolytic copper foil obtained by an electrolytic method.

(iii) Thickness Ratio of Current Collector and Negative Electrode Active Substance Layer The thickness ratio of the current collector and the negative electrode active material layer is not particularly restricted; however, the value of "(Thickness of negative electrode active material layer on one side immediately before injection of nonaqueous electrolyte solution)/(Thickness of current collector)" is preferably 150 or smaller, more preferably 20 or smaller, particularly preferably 10 or smaller, but preferably 0.1 or larger, more preferably 0.4 or larger, particularly preferably 1 or larger.

When the thickness ratio of the current collector and the negative electrode active material layer is higher than the above-described range, the current collector may generate heat due to Joule's heat during high-current-density charging/discharging of the secondary battery. Meanwhile, when the thickness ratio is lower than the above-described range, the capacity of the secondary battery may be reduced due to an increase in the volume ratio of the current collector with respect to the negative electrode active material.

(iv) Electrode Density

The structure of an electrode formed from the negative electrode active material is not particularly restricted, and the density of the negative electrode active material existing on the current collector is preferably 1 g·cm$^{-3}$ or higher, more preferably 1.2 g·cm$^{-3}$ or higher, still more preferably 1.3 g·cm$^{-3}$ or higher, but preferably 4 g·cm$^{-3}$ or lower, more preferably 3 g·cm$^{-3}$ or lower, still more preferably 2.5 g·cm$^{-3}$ or lower, particularly preferably 1.7 g·cm$^{-3}$ or lower. When the density of the negative electrode active material existing on the current collector is in this range, particles of the negative electrode active material are unlikely to be destructed; therefore, an increase in the initial irreversible capacity of the secondary battery as well as deterioration of the high-current-density charge-discharge characteristics, which is caused by a reduction in the permeability of the nonaqueous electrolyte solution to the vicinity of the interface between the current collector and the negative electrode active material, are likely to be inhibited. In addition, since conductivity between the negative electrode active materials can be ensured, the capacity per unit volume can be increased without an increase in the battery resistance.

(v) Binder, Solvent, Other Components.

The slurry used for the formation of a negative electrode active material layer is usually prepared by mixing a binder, a thickening agent and the like with a solvent, and adding the resulting mixture to the negative electrode active material.

The binder used for binding the negative electrode active material is not particularly restricted as long as it is a material that is stable against the nonaqueous electrolyte solution and the solvent used in the electrode production.

Specific examples of the binder include:

resin-based polymers, such as polyethylene, polypropylene, polyethylene terephthalate, polymethyl methacrylate, aromatic polyamides, cellulose, and nitrocellulose;

rubbery polymers, such as SBR (styrene-butadiene rubbers), isoprene rubbers, butadiene rubbers, fluororubbers, NBR (acrylonitrile-butadiene rubbers), and ethylene-propylene rubbers;

thermoplastic elastomeric polymers, such as styrene-butadiene-styrene block copolymers and hydrogenation products thereof, EPDM (ethylene-propylene-diene terpolymers), styrene-ethylene-butadiene-styrene copolymers, styrene-isoprene-styrene block copolymers and hydrogenation products thereof;

soft resinous polymers, such as syndiotactic 1,2-polybutadiene, polyvinyl acetate, ethylene-vinyl acetate copolymers, and propylene-α-olefin copolymers;

fluorine-based polymers, such as polyvinylidene fluoride, polytetrafluoroethylene, fluorinated polyvinylidene fluoride, and tetrafluoroethylene-ethylene copolymers; and polymer compositions having ionic conductivity for alkali metal ions (particularly lithium ions).

Any of these binders may be used singly, or two or more thereof may be used in any combination at any ratio.

The type of the solvent used for the slurry formation is not particularly restricted as long as the solvent is capable of dissolving or dispersing the negative electrode active material and the binder as well as the thickening agent and the conductive material that are used as required, and either an aqueous solvent or an organic solvent may be used.

Examples of the aqueous solvent include water and alcohols, and examples of the organic solvent include N-methylpyrrolidone (NMP), dimethylformamide, dimethylacetamide, methyl ethyl ketone, cyclohexanone, methyl acetate, methyl acrylate, diethyltriamine, N,N-dimethylaminopropylamine, tetrahydrofuran (THF), toluene, acetone, diethyl ether, dimethylacetamide, hexamethylphosphoramide, dimethyl sulfoxide, benzene, xylene, quinoline, pyridine, methylnaphthalene, and hexane.

Particularly, when an aqueous solvent is used, it is preferred to add a dispersant or the like in combination with the thickening agent and prepare a slurry using a latex such as SBR.

Any of the above-described solvents may be used singly, or two or more thereof may be used in any combination at any ratio.

The ratio of the binder with respect to 100 parts by mass of the negative electrode active material is preferably 0.1 parts by mass or higher, more preferably 0.5 parts by mass or higher, still more preferably 0.6 parts by mass or higher, but preferably 20 parts by mass or lower, more preferably 15 parts by mass or lower, still more preferably 10 parts by mass or lower, particularly preferably 8 parts by mass or lower. When the ratio of the binder with respect to the negative electrode active material is in this range, since the ratio of the binder not contributing to the battery capacity is not increased, the battery capacity is unlikely to be reduced. In addition, a reduction in the strength of the negative electrode is unlikely to occur.

Particularly, when the slurry, which is a negative electrode-forming material, contains a rubbery polymer as typified by SBR as a main component, the ratio of the binder with respect to 100 parts by mass of the negative electrode active material is preferably 0.1 parts by mass or higher, more preferably 0.5 parts by mass or higher, still more preferably 0.6 parts by mass or higher, but preferably 5 parts by mass or lower, more preferably 3 parts by mass or lower, still more preferably 2 parts by mass or lower.

Further, when the slurry contains a fluorine-based polymer as typified by polyvinylidene fluoride as a main component, the ratio of the binder with respect to 100 parts by mass of the negative electrode active material is preferably 1 part by mass or higher, more preferably 2 parts by mass or higher, still more preferably 3 parts by mass or higher, but preferably 15 parts by mass or lower, more preferably 10 parts by mass or lower, still more preferably 8 parts by mass or lower.

A thickening agent is usually used for the purpose of adjusting the viscosity of the slurry. The thickening agent is not particularly restricted, and specific examples thereof include carboxymethyl cellulose, methyl cellulose, hydroxymethyl cellulose, ethyl cellulose, polyvinyl alcohol, oxidized starch, phosphorylated starch, casein, and salts thereof. Any of these thickening agents may be used singly, or two or more thereof may be used in any combination at any ratio.

In cases where a thickening agent is used, the ratio thereof with respect to 100 parts by mass of the negative electrode active material is usually 0.1 parts by mass or higher, preferably 0.5 parts by mass or higher, more preferably 0.6 parts by mass or higher, but usually 5 parts by mass or lower, preferably 3 parts by mass or lower, more preferably 2 parts by mass or lower. When the ratio of the thickening agent with respect to the negative electrode active material is in this range, the slurry has good coatability. In addition, since the ratio of the negative electrode active material in the negative electrode active material layer is appropriate, problems of a reduction in the battery capacity and an increase in the resistance between the negative electrode active material are unlikely to occur.

(vi) Area of Negative Electrode Plate

The area of the negative electrode plate is not particularly restricted; however, the negative electrode plate is preferably designed to be slightly larger than the opposing positive electrode plate such that the positive electrode plate does not extend outward beyond the negative electrode plate. Further, from the standpoints of improving the cycle life in repeated charging and discharging of the secondary battery and inhibiting deterioration caused by high-temperature storage, the area of the negative electrode plate is preferably as close to that of the positive electrode as possible since this leads to an increase in the ratio of the electrode that works more uniformly and effectively, and the battery characteristics are thereby improved. Particularly, when the secondary battery is used at a high current, such a design of the negative electrode plate area is important.

<3-1-4. Positive Electrode>

The positive electrode used in the nonaqueous electrolyte secondary battery of the present invention will now be described.

<3-1-4-1. Positive Electrode Active Substance>

First, a positive electrode active material used in the positive electrode will be described.

(1) Composition

The positive electrode active material is not particularly restricted as long as it is capable of electrochemically absorbing and releasing metal ions; however, the positive electrode active material is preferably, for example, a substance that is capable of electrochemically absorbing and releasing lithium ions and contains lithium and at least one transition metal. Specific examples thereof include lithium-transition metal composite oxides, lithium-containing transition metal phosphate compounds, lithium-containing transition metal silicate compounds, and lithium-containing transition metal borate compounds.

As the transition metals of the lithium-transition metal composite oxides, for example, V, Ti, Cr, Mn, Fe, Co, Ni and Cu are preferred, and specific examples of the composite oxides include: lithium-cobalt composite oxides, such as $LiCoO_2$; lithium-nickel composite oxides, such as $LiNiO_2$; lithium-manganese composite oxides, such as $LiMnO_2$, $LiMn_2O_4$ and $Li_2MnO_4$; and these lithium-transition metal composite oxides in which some of the transition metal atoms contained as a main constituent are substituted with other metal such as Al, Ti, V, Cr, Mn, Fe, Co, Li, Ni, Cu, Zn, Mg, Ga, Zr, Si, Nb, Mo, Sn, or W.

Specific examples of such substituted lithium-transition metal composite oxides include $LiNi_{0.5}Mn_{0.5}O_2$, $LiNi_{0.85}Co_{0.10}Al_{0.05}O_2$, $LiNi_{0.33}Co_{0.33}Mn_{0.33}O_2$, $LiMn_2O_4$, $LiMn_{1.8}Al_{0.2}O_4$, $Li_{1.1}Mn_{1.9}Al_{0.1}O_4$, and $LiMn_{1.5}Ni_{0.5}O_4$.

Thereamong, composite oxides containing lithium, nickel and cobalt are more preferred. This is because a composite oxide containing cobalt and nickel can increase the capacity when the secondary battery is used at the same potential.

On the other hand, cobalt is not abundant in terms of resource amount and is thus an expensive metal, and a large amount of active material is used in large-sized batteries for automobile applications and the like where a large capacity is required; therefore, from the cost standpoint, it is also desirable to use manganese, which is a less expensive transition metal, as a main component. In other words, lithium-nickel-cobalt-manganese composite oxides are more preferred. Thereamong, from the standpoint of satisfying the balance of the cost and the capacity at a high level, lithium-nickel-cobalt-manganese composite oxides in which the amount of cobalt is reduced while the amount of nickel is increased are particularly preferred. Particularly preferred specific examples thereof include $LiNi_{0.5}Co_{0.2}Mn_{0.3}O_2$, $LiNi_{0.6}Co_{0.2}Mn_{0.2}O_2$, and $LiNi_{0.8}Co_{0.1}Mn_{0.1}O_2$.

In view of the stability as a compound and the acquisition cost based on the ease of production, lithium-manganese composite oxides having a spinel structure are also preferred. In other words, among the above-described specific examples, for example, $LiMn_2O_4$, $LiMn_{1.8}Al_{0.2}O_4$, $Li_{1.1}Mn_{1.9}Al_{0.1}O_4$, and $LiMn_{1.5}Ni_{0.5}O_4$ can also be mentioned as preferred specific examples.

As the transition metals of the above-described lithium-containing transition metal phosphate compounds, for example, V, Ti, Cr, Mn, Fe, Co, Ni and Cu are preferred, and specific examples of the phosphate compounds include: iron phosphates, such as $LiFePO_4$, $Li_3Fe_2(PO_4)_3$, and $LiFeP_2O_7$; cobalt phosphates, such as $LiCoPO_4$; manganese phosphates, such as $LiMnPO_4$; and these lithium-containing transition metal phosphate compounds in which some of the transition metal atoms contained as a main constituent are substituted with other metal such as Al, Ti, V, Cr, Mn, Fe, Co, Li, Ni, Cu, Zn, Mg, Ga, Zr, Si, Nb, Mo, Sn, or W.

As the transition metals of the above-described lithium-containing transition metal silicate compounds, for example, V, Ti, Cr, Mn, Fe, Co, Ni and Cu are preferred, and specific examples of the silicate compounds include: iron silicates, such as $Li_2FeSiO_4$; cobalt silicates, such as $Li_2CoSiO_4$; and these lithium-containing transition metal silicate compounds in which some of the transition metal atoms contained as a main constituent are substituted with other metal such as Al, Ti, V, Cr, Mn, Fe, Co, Li, Ni, Cu, Zn, Mg, Ga, Zr, Si, Nb, Mo, Sn, or W.

As the transition metals of the above-described lithium-containing transition metal borate compounds, for example, V, Ti, Cr, Mn, Fe, Co, Ni and Cu are preferred, and specific examples of the borate compounds include: iron borates, such as $LiFeBO_3$; cobalt borates, such as $LiCoBO_3$; and these lithium-containing transition metal borate compounds in which some of the transition metal atoms contained as a main constituent are substituted with other metal such as Al, Ti, V, Cr, Mn, Fe, Co, Li, Ni, Cu, Zn, Mg, Ga, Zr, Si, Nb, Mo, Sn, or W.

(2) Method of Producing Positive Electrode Active Substance

A method of producing the positive electrode active material is not particularly restricted within a range that does not depart from the gist of the present invention. Examples thereof include several methods, and a general method of producing an inorganic compound may be employed.

Particularly, for the production of a spherical or ellipsoidal active material, a variety of methods can be considered. One example thereof is a method in which a transition metal raw material substance (e.g., a nitrate salt or sulfate salt of a transition metal) and, as required, a raw material substance of other element are dissolved, or pulverized and dispersed in a solvent such as water, the pH of the resulting solution or dispersion is adjusted with stirring to produce and recover a spherical precursor, and this precursor is subsequently dried as required, after which a Li source such as LiOH, $Li_2CO_3$ or $LiNO_3$ is added thereto and the resultant is fired at a high temperature to obtain an active material.

Another example is a method in which a transition metal raw material substance (e.g., a nitrate salt, sulfate salt, hydroxide, oxide or the like of a transition metal) and, as required, a raw material substance of other element are dissolved, or pulverized and dispersed in a solvent such as water, and the resulting solution or dispersion is dried and shaped using a spray dryer or the like to produce a spherical or ellipsoidal precursor, after which a Li source such as LiOH, $Li_2CO_3$ or $LiNO_3$ is added thereto and the resultant is fired at a high temperature to obtain an active material.

Yet another example is a method in which a transition metal raw material substance (e.g., a nitrate salt, sulfate salt, hydroxide, oxide or the like of a transition metal), a Li source such as LiOH, $Li_2CO_3$ or $LiNO_3$ and, as required, a raw material substance of other element are dissolved, or pulverized and dispersed in a solvent such as water, and the resulting solution or dispersion is dried and shaped using a spray dryer or the like to produce a spherical or ellipsoidal precursor, after which this precursor is fired at a high temperature to obtain an active material.

<3-1-4-2. Constitution and Production Method of Positive Electrode>

The constitution of the positive electrode used in the present invention and a method of producing the positive electrode will now be described.

(Method of Producing Positive Electrode)

The positive electrode is produced by forming a positive electrode active material layer containing particles of the positive electrode active material and a binder on a current collector. Such production of the positive electrode using the positive electrode active material can be carried out by any known method. For example, a positive electrode active material layer is formed on a current collector by dry-mixing the positive electrode active material and a binder with, as required, a conductive material, a thickening agent and the like to form a sheet and subsequently press-bonding this sheet onto a positive electrode current collector, or by dissolving or dispersing these materials in a liquid medium to prepare a slurry and subsequently applying and drying this slurry onto a positive electrode current collector, whereby the positive electrode can be obtained.

The content of the positive electrode active material in the positive electrode active material layer is preferably 60% by mass or higher, more preferably 70% by mass or higher, still more preferably 80% by mass or higher, but preferably 99.9% by mass or less, more preferably 99% by mass or less. When the content of the positive electrode active material is in this range, a sufficient capacitance can be ensured. In addition, the resulting positive electrode has a sufficient strength. A single kind of the positive electrode active material powder of the present invention may be used alone, or two or more kinds thereof having different compositions or physical properties may be used in any combination at any ratio. When two or more kinds of active materials are used in combination, it is preferred to use the above-described composite oxide containing lithium and manganese as a powder component. As described above, in large-sized batteries for automobile applications and the like where a large capacity is required and a large amount of active material is used, cobalt and nickel are not preferred from the cost standpoint since they are not abundant in terms of resource amount and are thus expensive metals; therefore, it is desirable to use manganese, which is a less expensive transition metal, as a main component.

(Conductive Material)

As the conductive material, any known conductive material can be used. Specific examples thereof include metal materials, such as copper and nickel; and carbonaceous materials, such as graphites (e.g., natural graphites and artificial graphites), carbon blacks (e.g., acetylene black), and amorphous carbon (e.g., needle coke). Any of these conductive materials may be used singly, or two or more thereof may be used in any combination at any ratio.

The content of the conductive material in the positive electrode active material layer is preferably 0.01% by mass or higher, more preferably 0.1% by mass or higher, still more preferably 1% by mass or higher, but preferably 50% by mass or less, more preferably 30% by mass or less, still more preferably 15% by mass or less. When the content of the conductive material is in this range, a sufficient electrical conductivity can be ensured. In addition, a reduction in the battery capacity is likely to be inhibited.

(Binder)

The binder used for the production of the positive electrode active material layer is not particularly restricted as long as it is a material that is stable against the nonaqueous electrolyte solution and the solvent used in the electrode production.

When the positive electrode is produced by a coating method, the binder is not particular restricted as long as it is a material that can be dissolved or dispersed in the liquid medium used in the electrode production, and specific examples of such a binder include:

resin-based polymers, such as polyethylene, polypropylene, polyethylene terephthalate, polymethyl methacrylate, aromatic polyamides, cellulose, and nitrocellulose;

rubbery polymers, such as SBR (styrene-butadiene rubbers), NBR (acrylonitrile-butadiene rubbers), fluororubbers, isoprene rubbers, butadiene rubbers, and ethylene-propylene rubbers;

thermoplastic elastomeric polymers, such as styrene-butadiene-styrene block copolymers and hydrogenation products thereof, EPDM (ethylene-propylene-diene terpolymers), styrene-ethylene-butadiene-ethylene copolymers, styrene-isoprene-styrene block copolymers and hydrogenation products thereof;

soft resinous polymers, such as syndiotactic 1,2-polybutadiene, polyvinyl acetate, ethylene-vinyl acetate copolymers, and propylene-α-olefin copolymers;

fluorine-based polymers, such as polyvinylidene fluoride (PVdF), polytetrafluoroethylene, fluorinated polyvinylidene fluoride, and tetrafluoroethylene-ethylene copolymers; and polymer compositions having ionic conductivity for alkali metal ions (particularly lithium ions).

Any of these substances may be used singly, or two or more thereof may be used in any combination at any ratio.

The content of the binder in the positive electrode active material layer is preferably 0.1% by mass or higher, more preferably 1% by mass or higher, still more preferably 3% by mass or higher, but preferably 80% by mass or less, more preferably 60% by mass or less, still more preferably 40% by mass or less, particularly preferably 10% by mass or less. When the ratio of the binder is in this range, the positive electrode active material can be sufficiently retained, and the mechanical strength of the positive electrode can be ensured; therefore, favorable battery performance such as cycle characteristics are attained. This also leads to avoidance of a reduction in the battery capacity and conductivity.

(Liquid Medium)

The type of the liquid medium used in the preparation of a slurry used for forming the positive electrode active material layer is not particularly restricted as long as it is a solvent that is capable of dissolving or dispersing the positive electrode active material, the conductive material and the binder as well as a thickening agent used as required, and either an aqueous solvent or an organic solvent may be used.

Examples of the aqueous solvent include water, and mixed media of alcohol and water. Examples of the organic solvent include:

aliphatic hydrocarbons, such as hexane;

aromatic hydrocarbons, such as benzene, toluene, xylene, and methylnaphthalene;

heterocyclic compounds, such as quinoline and pyridine;

ketones, such as acetone, methyl ethyl ketone, and cyclohexanone;

esters, such as methyl acetate and methyl acrylate;

amines, such as diethylenetriamine and N,N-dimethylaminopropylamine;

ethers, such as diethyl ether and tetrahydrofuran (THF);

amides, such as N-methylpyrrolidone (NMP), dimethylformamide, and dimethylacetamide; and aprotic polar solvents, such as hexamethylphosphoramide and dimethyl sulfoxide.

Any of these media may be used singly, or two or more thereof may be used in any combination at any ratio.

(Thickening Agent)

When an aqueous medium is used as the liquid medium for the formation of a slurry, it is preferred to prepare a slurry using a thickening agent and a latex such as a styrene-butadiene rubber (SBR). The thickening agent is usually used for the purpose of adjusting the viscosity of the resulting slurry.

The thickening agent is not particularly restricted as long as it does not markedly limit the effects of the present invention, and specific examples of the thickening agent include carboxymethyl cellulose, methyl cellulose, hydroxymethyl cellulose, ethyl cellulose, polyvinyl alcohol, oxidized starch, phosphorylated starch, casein, and salts thereof. Any of these thickening agents may be used singly, or two or more thereof may be used in any combination at any ratio.

In cases where a thickening agent is used, the ratio thereof with respect to a total mass of the positive electrode active material and the thickening agent is preferably 0.1% by mass or higher, more preferably 0.5% by mass or higher, still more preferably 0.6% by mass or higher, but preferably 5% by mass or lower, more preferably 3% by mass or lower, still more preferably 2% by mass or lower. When the ratio of the thickening agent is in this range, a favorable coating property is attained, and the resulting positive electrode active material layer has a sufficient ratio of the active material; therefore, problems of a reduction in the capacity of the secondary battery and an increase in the resistance between the positive electrode active material are likely to be avoided.

(Consolidation)

The positive electrode active material layer obtained by applying and drying the above-described slurry onto a current collector is preferably consolidated by means of hand pressing, roller pressing or the like so as to increase the packing density of the positive electrode active material. The density of the positive electrode active material layer is preferably 1 g·cm$^{-3}$ or higher, more preferably 1.5 g·cm$^{-3}$ or higher, particularly preferably 2 g·cm$^{-3}$ or higher, but preferably 4 g·cm$^{-3}$ or lower, more preferably 3.9 g·cm$^{-3}$ or lower, still more preferably 3.8 g·cm$^{-3}$ or lower, particularly preferably 3.5 g·cm$^{-3}$ or lower, most preferably 3 g·cm$^{-3}$ or lower.

When the density of the positive electrode active material layer is in this range, the permeability of the nonaqueous electrolyte solution to the vicinity of the interface between the current collector and the active material is not reduced, so that favorable charge-discharge characteristics of the secondary battery are attained particularly at high current densities. In addition, neither a reduction in the conductivity between the active materials nor an increase in the battery resistance is likely to occur.

(Current Collector)

The material of the positive electrode current collector is not particularly restricted, and any known material can be used. Specific examples thereof include: metal materials, such as aluminum, stainless steel, nickel-plated steel, titanium, and tantalum; and carbonaceous materials, such as carbon cloth and carbon paper. Thereamong, a metal material, particularly aluminum, is preferred.

When the current collector is a metal material, the current collector may have any shape of, for example, a metal foil, a metal cylinder, a metal coil, a metal sheet, a metal thin film, an expanded metal, a punched metal, and a foamed metal and, when the current collector is a carbonaceous material, examples thereof include a carbon sheet, a carbon thin film, and a carbon cylinder. Thereamong, the current collector is preferably a metal thin film. As appropriate, the thin film current collector may be in the form of a mesh.

The current collector may have any thickness; however, the thickness is preferably 1 μm or greater, more preferably 3 μm or greater, still more preferably 5 μm or greater, but preferably 1 mm or less, more preferably 100 Cpm or less, still more preferably 50 μm or less. When the thickness of the current collector is in this range; a sufficient strength required as a current collector can be ensured. In addition, the current collector has good ease of handling.

The thickness ratio of the current collector and the positive electrode active material layer is not particularly restricted; however, the value of "(Thickness of active material layer on one side immediately before injection of nonaqueous electrolyte solution)/(Thickness of current collector)" is preferably 150 or smaller, more preferably 20 or smaller, particularly preferably 10 or smaller, but preferably 0.1 or larger, more preferably 0.4 or larger, particularly preferably 1 or larger. When the thickness ratio of the current collector and the positive electrode active material layer is in this range, heat generation by the current collector due to Joule's heat during high-current-density charging/discharging of the secondary battery is unlikely to occur. In addition, the volume ratio of the current collector with respect to the positive electrode active material is hardly increased, so that a reduction in the battery capacity can be inhibited.

(Electrode Area)

From the standpoint of improving the stability under high-output and high-temperature conditions, the positive electrode active material layer preferably has a large area relative to the outer surface area of a battery outer casing. Specifically, the total area of the positive electrode is, in terms of area ratio, preferably 20 times or larger, more preferably 40 times or larger, with respect to the surface area of the outer casing of the nonaqueous electrolyte secondary battery. The "outer surface area of outer casing" refers to, in the case of a closed-bottom prism-shaped casing, a total area calculated from the length, the width and the thickness of a portion of the casing that is filled with a power-generating element, excluding the projecting parts of the terminals. In the case of a closed-bottom cylindrical casing, the "outer surface area of outer casing" refers to a geometric surface area determined by approximation of a portion of the casing that is filled with a power-generating element, excluding the projecting parts of the terminals, to a cylinder. The "the total area of the positive electrode", which is a geometric surface area of a positive electrode mixture layer facing a mixture layer containing the negative electrode active material, refers to a sum of the areas of the respective surfaces in a structure in which positive electrode layer mixture layers are formed on the respective sides via a current collector foil.

(Discharge Capacity)

When the nonaqueous electrolyte solution of the present invention is used, the capacitance of the element(s) of the nonaqueous electrolyte secondary battery that is/are housed in a single battery casing (the capacitance measured in the course of discharging the battery from a fully-charged state to a discharged state) is preferably 1 ampere hour (Ah) or higher since this leads to an enhanced effect of improving the low-temperature discharge characteristics. Accordingly, the positive electrode plate is designed to have a discharge capacity of preferably 3 Ah (ampere hour) or higher, more preferably 4 Ah or higher, but preferably 20 Ah or less, more preferably 10 Ah or less, in a fully-charged state.

When the discharge capacity is in this range, a voltage drop caused by electrode reaction resistance during extraction of a large current is not overly large, so that a reduction in the power efficiency can be inhibited. In addition, since the temperature distribution caused by internal heat generation of the battery during pulse charging and discharging is not excessively wide, phenomena of deterioration in the durability against repeated charging and discharging and a reduction in the heat dissipation efficiency against abrupt heat generation in the event of a defect such as overcharging or internal short-circuiting can be avoided.

(Thickness of Positive Electrode Plate)

The thickness of the positive electrode plate is not particularly restricted; however, from the standpoint of attaining a high capacity and a high output as well as excellent rate characteristics, the thickness of the positive electrode active material layer excluding the thickness of the current collector is preferably 10 μm or greater, more preferably 20 μm or greater, but preferably 200 μm or less, more preferably 150 μm or less, still more preferably 100 μm or less, on one side of the current collector.

<3-1-5. Separator>

In the nonaqueous electrolyte secondary battery of the present invention, a separator is usually arranged between the positive electrode and the negative electrode for the purpose of inhibiting a short circuit. In this case, the separator is usually impregnated with the nonaqueous electrolyte solution of the present invention.

The material and the shape of the separator are not particularly restricted as long as the separator does not markedly impair the effects of the present invention, and any known material and shape can be employed. Particularly, a separator formed from a material stable against the nonaqueous electrolyte solution of the present invention, such as a resin, a glass fiber or an inorganic material, can be used, and it is preferred to use a separator in the form of, for example, a porous sheet or nonwoven fabric that has excellent liquid retainability.

As the material of a resin or glass-fiber separator, for example, polyolefins such as polyethylene and polypropylene, aramid resins, polytetrafluoroethylenes, polyether sulfones, and glass filters can be used. Thereamong, glass filters and polyolefins are preferred, and polyolefins are more preferred. Any of these materials may be used singly, or two or more thereof may be used in any combination at any ratio.

The thickness of the separator may be set arbitrarily; however, it is preferably 1 µm or greater, more preferably 5 µm or greater, still more preferably 10 µm or greater, but preferably 50 µm or less, more preferably 40 µm or less, still more preferably 30 µm or less. When the thickness of the separator is in this range, good insulation and mechanical strength are attained. In addition, not only deterioration of the battery performance such as the rate characteristics but also a reduction in the energy density of the nonaqueous electrolyte secondary battery as a whole can be inhibited.

In cases where a porous material such as a porous sheet or a nonwoven fabric is used as the separator, the porosity of the separator may be set arbitrarily; however, it is preferably 20% or higher, more preferably 35% or higher, still more preferably 45% or higher, but preferably 90% or lower, more preferably 85% or lower, still more preferably 75% or lower. When the porosity is in this range, the membrane resistance is prevented from being excessively high, so that deterioration of the rate characteristics of the secondary battery can be inhibited. In addition, since the separator has an appropriate mechanical strength, a reduction in the insulation can be inhibited as well.

The average pore size of the separator may also be set arbitrarily; however, it is preferably 0.5 µm or smaller, more preferably 0.2 µm or smaller, but preferably 0.05 µm or larger. When the average pore size is in this range, a short circuit is unlikely to occur. In addition, the membrane resistance is prevented from being excessively high, so that deterioration of the rate characteristics of the secondary battery can be inhibited.

Meanwhile, as the material of an inorganic separator, for example, an oxide such as alumina or silicon dioxide, a nitride such as aluminum nitride or silicon nitride, or a sulfate such as barium sulfate or calcium sulfate can be used, and the inorganic separator may have a particulate shape or a fibrous shape.

With regard to the form of the separator, a thin film such as a nonwoven fabric, a woven fabric, or a microporous film may be used. As a thin-film separator, one having a pore size of 0.01 to 1 µm and a thickness of 5 to 50 µm is preferably used. Aside from such an independent thin-film separator, a separator that is formed as, with the use of a resin binder, a composite porous layer containing particles of the above-described inorganic material on the surface layer of the positive electrode and/or the negative electrode, can be used. For example, on both sides of the positive electrode, a porous layer may be formed using alumina particles having a 90% particle size of smaller than 1 µm along with a fluorine resin as a binder.

<3-1-6. Battery Design>
(Electrode Group)

An electrode group may have either a layered structure in which the above-described positive electrode plate and negative electrode plate are layered with the above-described separator being interposed therebetween, or a wound structure in which the above-described positive electrode plate and negative electrode plate are spirally wound with the above-described separator being interposed therebetween. The volume ratio of the electrode group with respect to the internal volume of the battery (this volume ratio is hereinafter referred to as "electrode group occupancy") is preferably 40% or higher, more preferably 50% or higher, but preferably 95% or lower, more preferably 90% or lower. When the electrode group occupancy is in this range, the battery capacity is unlikely to be reduced. In addition, an appropriate amount of void space can be ensured; therefore, an increase in the internal pressure, which is caused by swelling of members and an increase in the vapor pressure of the liquid component of the nonaqueous electrolyte solution due to an increase in the battery temperature, as well as the resulting deterioration of various properties of the secondary battery, such as the charging-discharging repeating performance and the high-temperature storage characteristics, and activation of a gas release valve used for relieving the internal pressure to the outside, can be avoided.

(Current Collector Structure)

The current collector structure is not particularly restricted; however, in order to more effectively realize an improvement of the discharge characteristics attributed to the nonaqueous electrolyte solution of the present invention, it is preferred to adopt a structure that reduces the resistance of wiring and joint parts. By reducing the internal resistance in this manner, the effects of using the nonaqueous electrolyte solution of the present invention are particularly favorably exerted.

In an electrode group having the above-described layered structure, the metal core portions of the respective electrode layers are preferably bundled and welded to a terminal. When the area of a single electrode is large, the internal resistance is high; therefore, it is also preferred to reduce the resistance by arranging plural terminals in each electrode. In an electrode group having the above-described wound structure, the internal resistance can be reduced by arranging plural lead structures on each of the positive electrode and the negative electrode and bundling them to a terminal.

(Protective Element)

Examples of a protective element include a PTC (Positive Temperature Coefficient) thermistor whose resistance increases in the event of abnormal heat generation or excessive current flow, a thermal fuse, and a valve (current cutoff valve) that blocks a current flowing into a circuit in response to a rapid increase in the internal pressure or internal temperature of the battery in the event of abnormal heat generation. The protective element is preferably selected from those that are not activated during normal use at a high current, and it is more preferred to design the battery such that neither abnormal heat generation nor thermal runaway occurs even without a protective element.

(Outer Package)

The nonaqueous electrolyte secondary battery of the present invention is usually constructed by housing the above-described nonaqueous electrolyte solution, negative electrode, positive electrode, separator and the like in an outer package (outer casing). This outer package is not restricted, and any known outer package can be employed as long as it does not markedly impair the effects of the present invention.

The material of the outer casing is not particularly restricted as long as it is a material that is stable against the nonaqueous electrolyte solution to be used. Specifically, a metal such as a nickel-plated steel sheet, stainless steel, aluminum, an aluminum alloy, a magnesium alloy, nickel or titanium, or a laminated film composed of a resin and an aluminum foil can be used. From the standpoint of weight reduction, it is preferred to use a metal such as aluminum or an aluminum alloy, or a laminated film.

Examples of an outer casing using any of the above-described metals include those having a hermetically sealed structure obtained by welding metal pieces together by laser welding, resistance welding or ultrasonic welding, and those having a caulked structure obtained using the above-described metals via a resin gasket. Examples of an outer casing using the above-described laminated film include those having a hermetically sealed structure obtained by heat-fusing resin layers together. In order to improve the sealing performance, a resin different from the resin used in the laminated film may be interposed between the resin layers. Particularly, in the case of forming a sealed structure by heat-fusing resin layers via a collector terminal, since it involves bonding between a metal and a resin, a polar group-containing resin or a resin modified by introduction of a polar group is preferably used as the resin to be interposed.

Further, the shape of the outer casing may be selected arbitrarily, and the outer casing may have any of, for example, a cylindrical shape, a prismatic shape, a laminated shape, a coin shape, and a large-sized shape.

<3-2. Nonaqueous Electrolyte Primary Battery>

In a nonaqueous electrolyte primary battery according to one embodiment of the present invention, for example, a material capable of absorbing metal ions is used as a positive electrode, while a material capable of releasing metal ions is used as a negative electrode. As a material of the positive electrode, a transition metal oxide such as fluorinated graphite or manganese dioxide is preferred. As a material of the negative electrode, a metal such as zinc or lithium is preferred. As a nonaqueous electrolyte solution, the above-described nonaqueous electrolyte solution of the present invention is used.

<3-3. Metal Ion Capacitor>

In a metal ion capacitor according to one embodiment of the present invention, for example, a material capable of forming an electric double layer is used as a positive electrode, while a material capable of absorbing and releasing metal ions is used as a negative electrode. As a material of the positive electrode, activated carbon is preferred. Further, as a material of the negative electrode, a carbonaceous material is preferred. As a nonaqueous electrolyte solution, the above-described nonaqueous electrolyte solution of the present invention is used.

<3-4. Electric Double Layer Capacitor>

In an electric double layer capacitor according to one embodiment of the present invention, for example, a material capable of forming an electric double layer is used as electrodes. As a material of the electrodes, activated carbon is preferred. As a nonaqueous electrolyte solution, the above-described nonaqueous electrolyte solution of the present invention is used.

EXAMPLES

The present invention will now be described more concretely by way of Examples and Comparative Examples; however, the present invention is not restricted thereto within the gist of the present invention.

Compounds that were used as constituents of nonaqueous electrolyte solutions in Examples and Comparative Examples are shown below. The compounds (α) and (β) each correspond to the specific ether of the present invention, and the compound (γ) corresponds to the specific additive of the present invention.

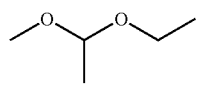
(α)

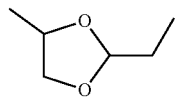
(β)

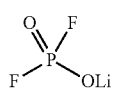
(γ)

Examples 1-1 and 1-2, and Comparative Example 1-1

[Production of Nonaqueous Electrolyte Secondary Batteries]

<Preparation of Nonaqueous Electrolyte Solutions>

Example 1-1

Under a dry argon atmosphere, thoroughly dried $LiPF_6$ was dissolved at a concentration of 1 mol/L (in terms of the concentration in the resulting nonaqueous electrolyte solution) in a mixture of ethylene carbonate, dimethyl carbonate and ethyl methyl carbonate (volume ratio=3:3:4), and the compound (α) was further dissolved therein in an amount of 2 ppm by mass (in terms of the concentration in the resulting nonaqueous electrolyte solution) to prepare a nonaqueous electrolyte solution. A nonaqueous electrolyte secondary battery was produced by the below-described method using the thus obtained nonaqueous electrolyte solution, and the below-described evaluations were conducted.

Example 1-2

A nonaqueous electrolyte secondary battery was produced in the same manner as in Example 1-1, except that the compound (α) was not dissolved and the compound (β) was instead dissolved in an amount of 2 ppm by mass, and the below-described evaluations were conducted.

Comparative Example 1-1

A nonaqueous electrolyte secondary battery was produced in the same manner as in Example 1-1, except that the compound (α) was not dissolved, and the below-described evaluations were conducted.

<Production of Positive Electrode>

A slurry was prepared by mixing 90 parts by mass of lithium-nickel-manganese-cobalt composite oxide ($LiNi_{0.6}Mn_{0.2}Co_{0.2}O_2$) as a positive electrode active material, 7 parts by mass of carbon black as a conductive material and 3 parts by mass of polyvinylidene fluoride (PVdF) as a binder in N-methyl-2-pyrrolidone. A 15 μm-thick aluminum foil was uniformly coated with the thus obtained slurry, and this aluminum foil was dried and then roll-pressed to obtain a positive electrode.

<Production of Negative Electrode>

To 98 parts by mass of graphite powder, 100 parts by mass of an aqueous dispersion of sodium carboxymethyl cellulose (concentration of sodium carboxymethyl cellulose=1% by mass) and 2 parts by mass of an aqueous dispersion of styrene-butadiene rubber (concentration of styrene-butadiene rubber=50% by mass) were added as a thickening agent and a binder, respectively, and these materials were mixed using a disperser to prepare a slurry. A 10 μm-thick copper foil was uniformly coated with the thus obtained slurry, and this copper foil was dried and then roll-pressed to obtain a negative electrode.

<Production of Nonaqueous Electrolyte Secondary Batteries>

The above-obtained positive electrode and negative electrode were laminated with a polyolefin separator, which had been impregnated with each of the above-described nonaqueous electrolyte solutions of Examples and Comparative Examples in advance, in the order of the positive electrode, the separator, and the negative electrode. The thus obtained battery element was placed in a can for a 2032 coin-type battery, and the can was caulked using a caulking machine, whereby a coin-type nonaqueous electrolyte secondary battery was produced.

[Evaluation of Nonaqueous Electrolyte Secondary Batteries]
Initial Charging and Discharging In a 25° C. thermostat chamber, each secondary battery produced by the above-described method was subjected to constant current-constant voltage charging up to 4.2 V (the constant voltage charging was performed until the current was reduced to 0.05 C; the same applies below) at 0.3 C (a current value at which the rated capacity based on the hourly discharge capacity is discharged in one hour is defined as 1 C; the same applies below), and then discharged to 2.5 V at 0.3 C. Subsequently, the battery was subjected to constant current-constant voltage charging up to 4.1 V at 0.3 C and then maintained at 25° C. for 2 hours to perform aging, after which the battery was discharged to 2.5 V at 25° C. and 0.3 C. Thereafter, the battery was further subjected to constant current-constant voltage charging up to 4.2 V at 0.3 C and then discharged to 2.5 V at 0.3 C. In this manner, each nonaqueous electrolyte secondary battery was stabilized.

Repeated Charging-Discharging Test at 25° C.

The thus stabilized nonaqueous electrolyte secondary battery was subjected to a 100-cycle repeated charging-discharging test in which each cycle consisted of constant current-constant voltage charging of the battery to 4.2V at 0.3 C and subsequent discharging of the battery to 2.5 V at 0.3 C in a 25° C. thermostat chamber.

Evaluation of Charging Characteristics after Repeated Charging-Discharging Test

After the 100-cycle repeated charging-discharging test, the nonaqueous electrolyte secondary battery was subjected to constant current-constant voltage charging up to 4.2V at 0.3 C in a 25° C. thermostat chamber. In this process, the constant-voltage charging time was measured after the voltage reached 4.2 V, and the thus obtained value was defined as CV time in charging.

The thus determined values of the CV time in charging, which were normalized with the value of Comparative Example 1-1, are shown in Table 1 below.

TABLE 1

| No. | Content in nonaqueous electrolyte solution (ppm by mass) | | CV time in charging |
|---|---|---|---|
| | Compound (α) | Compound (β) | |
| Example 1-1 | 2 | — | 92% |
| Example 1-2 | — | 2 | 86% |
| Comparative Example 1-1 | — | — | 100% |

As apparent from Table 1, the use of the respective specific ether-containing nonaqueous electrolyte solutions resulted in a shortened CV time in charging, exhibiting an effect that is presumed to be a reduction in the resistance attributed to an overvoltage during charging.

Examples 2-1 to 2-6 and Comparative Examples 2-1 and 2-2

[Production of Nonaqueous Electrolyte Secondary Batteries]
<Preparation of Nonaqueous Electrolyte Solutions>

Example 2-1

A nonaqueous electrolyte secondary battery was produced in the same manner as in Example 1-1, and the below-described evaluations were conducted.

Example 2-2

A nonaqueous electrolyte secondary battery was produced in the same manner as in Example 2-1, except that the amount of the dissolved compound (α) was changed to 10 ppm by mass, and the below-described evaluations were conducted.

Example 2-3

A nonaqueous electrolyte secondary battery was produced in the same manner as in Example 2-1, except that the compound (α) was not dissolved and the compound (β) was instead dissolved in an amount of 2 ppm by mass, and the below-described evaluations were conducted.

Example 2-4

A nonaqueous electrolyte secondary battery was produced in the same manner as in Example 2-1, except that the compound (α) was not dissolved and the compound (β) was instead dissolved in an amount of 10 ppm by mass, and the below-described evaluations were conducted.

Example 2-5

A nonaqueous electrolyte secondary battery was produced in the same manner as in Example 2-1, except that the compound (γ) was further dissolved in an amount of 0.5% by mass, and the below-described evaluations were conducted.

Example 2-6

A nonaqueous electrolyte secondary battery was produced in the same manner as in Example 2-1, except that the compound (α) was not dissolved and the compound (β) was instead dissolved in an amount of 2 ppm by mass, and that the compound (γ) was further dissolved in an amount of 0.5% by mass, and the below-described evaluations were conducted.

Comparative Example 2-1

A nonaqueous electrolyte secondary battery was produced in the same manner as in Example 2-1, except that the compound (α) was not dissolved, and the below-described evaluations were conducted.

Comparative Example 2-2

A nonaqueous electrolyte secondary battery was produced in the same manner as in Comparative Example 2-1, except that the compound (α) was not dissolved and the compound (γ) was dissolved in an amount of 0.5% by mass, and the below-described evaluations were conducted.

<Production of Positive Electrodes>

Positive electrodes of Examples 2-1 to 2-6 and Comparative Examples 2-1 and 2-2 were produced in the same manner as in Example 1-1.

<Production of Negative Electrodes>

Negative electrodes of Examples 2-1 to 2-6 and Comparative Examples 2-1 and 2-2 were produced in the same manner as in Example 1-1.

<Production of Nonaqueous Electrolyte Secondary Batteries>

Nonaqueous electrolyte secondary batteries of Examples 2-1 to 2-6 and Comparative Examples 2-1 and 2-2 were each produced in the same manner as in Example 1-1, except that the nonaqueous electrolyte solution was changed.

[Evaluation of Nonaqueous Electrolyte Secondary Batteries]

Initial Charging and Discharging

In a 25° C. thermostat chamber, each secondary battery produced by the above-described method was subjected to constant current-constant voltage charging up to 4.2 V (the constant voltage charging was performed until the current was reduced to 0.05 C; the same applies below) at 0.3 C (a current value at which the rated capacity based on the hourly discharge capacity is discharged in one hour is defined as 1 C; the same applies below), and then discharged to 2.5 V at 0.3 C. Subsequently, the battery was subjected to constant current-constant voltage charging up to 4.1 V at 0.3 C and then maintained at 25° C. for 2 hours to perform aging, after which the battery was discharged to 2.5 V at 25° C. and 0.3 C. Thereafter, the battery was further subjected to constant current-constant voltage charging up to 4.2 V at 0.3 C and then discharged to 2.5 V at 0.3 C. In this manner, each nonaqueous electrolyte secondary battery was stabilized.

Initial High-Current Discharging Test

In a 25° C. thermostat chamber, the thus stabilized nonaqueous electrolyte secondary battery was subjected to constant current-constant voltage charging up to 4.2 V at 0.3 C and then discharged to 2.5 V at 0.3 C. The discharge capacity in this process was defined as initial low-rate capacity. Subsequently, the battery was subjected to constant current-constant voltage charging up to 4.2 V at 0.3 C and then discharged to 2.5 V at 2 C. The discharge capacity in this process was defined as initial high-rate capacity.

The initial high-rate discharge performance (%) was calculated using the following equation:

Initial high-rate discharge performance (%)=100×(Initial high-rate capacity/Initial low-rate capacity)

Repeated Charging-Discharging Test at 25° C.

After the initial high-current discharging test, each nonaqueous electrolyte secondary battery was subjected to a 50-cycle repeated charging-discharging test in which each cycle consisted of constant current-constant voltage charging of the battery to 4.2V at 0.3 C and subsequent discharging of the battery to 2.5 V at 0.3 C in a 25° C. thermostat chamber.

High-Current Discharging Test after Repeated Charging-Discharging Test

After the 50-cycle repeated charging-discharging test, each nonaqueous electrolyte secondary battery was subjected to constant current-constant voltage charging up to 4.2V at 0.3 C and then discharged to 2.5 V at 0.3 C in a 25° C. thermostat chamber. The discharge capacity in this process was defined as post-test low-rate capacity. Subsequently, the battery was subjected to constant current-constant voltage charging up to 4.2 V at 0.3 C and then discharged to 2.5 V at 2 C. The discharge capacity in this process was defined as post-test high-rate capacity.

The post-test high-rate discharge performance (%) was calculated using the following equation:

Post-test high-rate discharge performance (%)=100×(Post-test high-rate capacity/Post-test low-rate capacity)

Table 2 below shows the values of the change in high-rate discharge performance (%), which were calculated by {(Post-test high-rate discharge performance)−(Initial high-rate discharge performance)}.

TABLE 2

| No. | Content in nonaqueous electrolyte solution | | | Change in high-rate discharge performance (%) |
|---|---|---|---|---|
| | Compound (α) | Compound (β) | Compound (γ) | |
| Example 2-1 | 2 ppm by mass | — | — | 5.3 |
| Example 2-2 | 10 ppm by mass | — | — | 2.7 |
| Example 2-3 | — | 2 ppm by mass | — | 0.8 |
| Example 2-4 | — | 10 ppm by mass | — | 0.4 |
| Example 2-5 | 2 ppm by mass | — | 0.5% by mass | 13.5 |
| Example 2-6 | — | 2 ppm by mass | 0.5% by mass | 12.5 |
| Comparative Example 2-1 | — | — | — | −1.1 |
| Comparative Example 2-2 | — | — | 0.5% by mass | 5.8 |

As apparent from Table 2, an addition of each specific ether improved the value of the change in the high-rate discharge performance and, in those cases where a specific ether and a specific additive were used simultaneously, an astonishing effect of improving the value of the change in the high-rate discharge performance was expressed at such a level that could not be expected from the behaviors observed when the specific ether and the specific additive were each used alone. In other words, the simultaneous use of the specific ether and the specific additive can markedly improve, rather than worsen, the high-rate discharge performance even after a repeated charging-discharging test.

Examples 3-1 and 3-2 and Comparative Examples 3-1 and 3-2

[Production of Nonaqueous Electrolyte Secondary Batteries]

<Preparation of Nonaqueous Electrolyte Solutions>

Example 3-1

A nonaqueous electrolyte secondary battery was produced in the same manner as in Example 2-6, and the below-described evaluations were conducted.

Example 3-2

A nonaqueous electrolyte secondary battery was produced in the same manner as in Example 3-1, except that the compound (γ) was not dissolved, and the below-described evaluations were conducted.

Comparative Example 3-1

A nonaqueous electrolyte secondary battery was produced in the same manner as in Example 3-1, except that the compound (β) and the compound (γ) were not dissolved, and the below-described evaluations were conducted.

Comparative Example 3-2

A nonaqueous electrolyte secondary battery was produced in the same manner as in Example 3-1, except that the compound ((β) was not dissolved, and the below-described evaluations were conducted.
<Production of Positive Electrodes>
Positive electrodes of Examples 3-1 and 3-2 and Comparative Example 3-1 and 3-2 were produced in the same manner as in Example 1-1.
<Production of Negative Electrodes>
Negative electrodes of Examples 3-1 and 3-2 and Comparative Example 3-1 and 3-2 were produced in the same manner as in Example 1-1.
<Production of Nonaqueous Electrolyte Secondary Batteries>
Nonaqueous electrolyte secondary batteries of Examples 3-1 and 3-2 and Comparative Examples 3-1 and 3-2 were each produced in the same manner as in Example 1-1, except that the nonaqueous electrolyte solution was changed.
[Evaluation of Nonaqueous Electrolyte Secondary Batteries]
Charging-Discharging Test
In a 25° C. thermostat chamber, each secondary battery produced by the above-described method was subjected to constant current-constant voltage charging up to 4.2 V (the constant voltage charging was performed until the current was reduced to 0.05 C) at 0.3 C (a current value at which the rated capacity based on the hourly discharge capacity is discharged in one hour is defined as 1 C; the same applies below), and then discharged to 2.5 V at 0.3 C. From the charge capacity and the discharge capacity that were measured in this process, the charge-discharge efficiency was calculated using the following equation:

Charge-discharge efficiency (%)=100×(Discharge capacity/Charge capacity)

The thus determined values of the charge-discharge efficiency, which were normalized with the value of Comparative Example 3-1, are shown in Table 3 below.

TABLE 3

| | Content in nonaqueous electrolyte solution | | Charge-discharge |
| --- | --- | --- | --- |
| No. | Compound (β) | Compound (γ) | efficiency (%) |
| Example 3-1 | 2 ppm by mass | 0.5% by mass | 102 |
| Example 3-2 | 2 ppm by mass | — | 98 |
| Comparative Example 3-1 | — | — | 100 |
| Comparative Example 3-2 | — | 0.5% by mass | 99 |

As apparent from Table 3, the specific ether and the specific additive each deteriorated the charge-discharge efficiency when used singly; however, the use of them in combination exhibited an astonishing effect of improving the charge-discharge efficiency.

Synthesis Example A1: Synthesis of 1,3,6-trioxo-can-2-one (1-A) and 1,3,6,9,11,14-hexaoxacyclo-hexadecane-2,10-dione (1-D)

To a reactor, 150 ml of dichloromethane, 2.13 g (7 mmol) of triphosgene and 2.25 g (21 mmol) of diethylene glycol were added, and a uniform solution was obtained under a nitrogen atmosphere.

To another reactor, 700 ml of dichloromethane and 3.33 g (42 mmol) of pyridine were added, and the above-obtained triphosgene-diethylene glycol solution was added thereto dropwise over a period of 5 hours under a nitrogen atmosphere at room temperature.

After the completion of the reaction, the reaction was quenched with water and a saturated sodium bicarbonate solution, and the resultant was washed with water, followed by solvent removal under reduced pressure. Ethyl acetate was added to the thus obtained crude product, and the resulting precipitate was subsequently separated by filtration to obtain 0.5 g of 1,3,6,9,11,14-hexaoxacyclohexadecane-2,10-dione (1-D). Further, the resulting filtrate was concentrated and then purified by silica gel chromatography to obtain 0.6 g of 1,3,6-trioxocan-2-one (1-A).

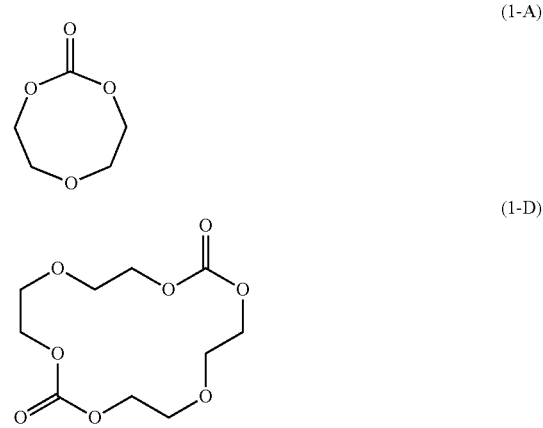

Synthesis Example A2: Synthesis of (1-B), (1-E) and (1-C)

In Synthesis Example A2, 1,3,6,9-tetraoxacycloundecane-2-one (1-B) and 1,3,6,9,12,14,17,20-octaoxacyclodocosane-2,13-dione (1-E) were synthesized in the same manner as described above except that diethylene glycol was changed to triethylene glycol, and 1,3,6,9,12-pentaoxacyclotetradecane-2-one (1-C) was synthesized in the same manner as described above except that diethylene glycol was changed to tetraethylene glycol.

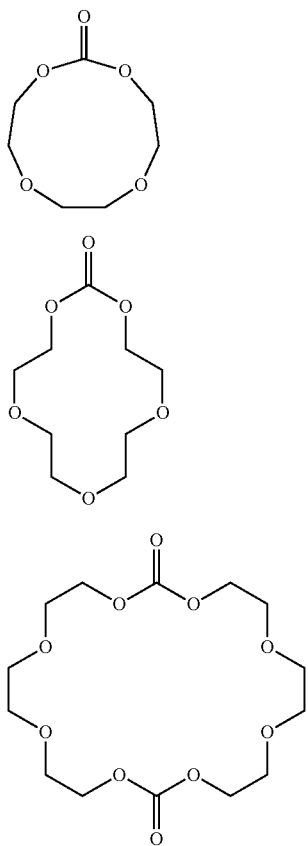

Example A1

[Production of Negative Electrode]

To 98 parts by mass of a carbonaceous material, 1 part by mass of an aqueous dispersion of sodium carboxymethyl cellulose (concentration of sodium carboxymethyl cellulose=1% by mass) and 1 part by mass of an aqueous dispersion of styrene-butadiene rubber (concentration of styrene-butadiene rubber=50% by mass) were added as a thickening agent and a binder, respectively, and these materials were mixed using a disperser to prepare a slurry. A 10 μm-thick copper foil was coated with the thus obtained slurry, and this copper foil was dried and then roll-pressed using a press machine, after which the resultant was cut out into a shape having an active material layer of 30 mm in width and 40 mm in length and an uncoated part of 5 mm in width and 9 mm in length, whereby a negative electrode was produced.

[Production of Positive Electrode]

A slurry was prepared by mixing 94% by mass of $LiCoO_2$ as a positive electrode active material, 3% by mass of acetylene black as a conductive material and 3% by mass of polyvinylidene fluoride (PVdF) as a binder in an N-methylpyrrolidone solvent. One side of a 15 μm-thick aluminum foil, which had been coated with a conductive auxiliary agent in advance, was coated with the thus obtained slurry, and this aluminum foil was dried and then roll-pressed using a press machine, after which the resultant was cut out into a shape having an active material layer of 30 mm in width and 40 mm in length and an uncoated part of 5 mm in width and 9 mm in length, whereby a positive electrode was produced.

[Preparation of Electrolyte Solution]

Under a dry argon atmosphere, dried $LiPF_6$ was dissolved in a mixture of ethylene carbonate (EC), diethyl carbonate (DEC) and ethyl methyl carbonate (EMC) (volume ratio=30:40:30) at a ratio of 1.2 mol/L to prepare an electrolyte solution. This electrolyte solution was mixed with 2 parts by mass of vinylene carbonate and 2 parts by mass of monofluoroethylene carbonate to obtain a standard electrolyte solution 1. An electrolyte solution of Example A1 was prepared by mixing 99 parts by mass of the thus obtained standard electrolyte solution 1 and 1 part by mass of 1,3,6-trioxocan-2-one (1-A).

[Production of Nonaqueous Electrolyte Secondary Batteries]

A battery element was prepared by laminating the above-obtained positive electrode and negative electrode along with a polyethylene separator in the order of the negative electrode, the separator, and the positive electrode. This battery element was inserted into a pouch made of a laminated film obtained by coating both sides of an aluminum sheet (thickness: 40 μm) with a resin layer, in such a manner that the terminals of the positive and negative electrodes protruded out of the pouch. Thereafter, the above-prepared electrolyte solution was injected into the pouch, and the pouch was subsequently vacuum-sealed, whereby a sheet-form nonaqueous electrolyte secondary battery of Example A1, which would be brought into a fully-charged state at 4.3 V, was produced.

[Evaluation of Initial Discharge Capacity]

At 25° C., the thus obtained nonaqueous electrolyte secondary battery in a state of being sandwiched by glass plates for improvement of the adhesion between the electrodes was charged to 4.35 V at a constant current equivalent to 0.2 C and then discharged to 3.0 V at a constant current of 0.2 C. Two cycles of these operations were performed to stabilize the battery and, in a third cycle, the battery was charged to 4.35 V at a constant current of 0.2 C, further charged at a constant voltage of 4.35 V until the current value was reduced to 0.05 C, and then discharged to 3.0 V at a constant current of 0.2 C. Thereafter, in a fourth cycle, the battery was charged to 4.35 V at a constant current of 0.2 C, further charged at a constant voltage of 4.35 V until the current value was reduced to 0.05 C, and then discharged to 3.0 V at a constant current of 0.2 C to determine the initial discharge capacity.

[Evaluation of Swelling in High-Temperature Storage]

After the completion of the evaluation of the initial discharge capacity, the battery was immersed in an ethanol bath to measure the volume, and the thus obtained value was defined as the volume before high-temperature storage. The battery was charged to 4.35 V at a constant current equivalent to 0.2 C at 25° C., stored for 14 days at 60° C. and then cooled to room temperature, after which the battery was immersed in an ethanol bath to measure the volume, and the thus obtained value was defined as the volume after high-temperature storage. A value obtained by subtracting the volume before high-temperature storage from the volume after high-temperature storage was defined as swelling in high-temperature storage. Table 4 shows the relative values (%) of swelling in high-temperature storage that were determined in the respective Examples, taking the value of swelling in high-temperature storage of Comparative Example A1 as 100.

[Evaluation of Storage Capacity Retention Rate]

The battery whose volume was measured after the high-temperature storage was subjected to a test in which the battery was, at 25° C., discharged to 3.0 V at a constant current of 0.2 C, charged to 4.35 V at a constant current of 0.2 C, further charged at a constant voltage until the current value was reduced to 0.05 C, and then discharged to 3.0 V at a constant current of 0.2 C, and the discharge capacity after the high-temperature storage at 0.2 C was determined. The storage capacity retention rate (%) was calculated using the following equation:

Storage capacity retention rate (%)=(Discharge capacity after high-temperature storage)/(Initial discharge capacity)×100

The values of the storage capacity retention rate are shown in Table 4.

Example A2

A sheet-form nonaqueous electrolyte secondary battery of Example A2 was produced and evaluated in the same manner as in Example A1, except that 99 parts by mass of the standard electrolyte solution 1 and 1 part by mass of 1,3,6,9-tetraoxacycloundecane-2-one (1-B) were mixed. The results thereof are shown in Table 4.

Example A3

A sheet-form nonaqueous electrolyte secondary battery of Example A3 was produced and evaluated in the same manner as in Example A1, except that 99 parts by mass of the standard electrolyte solution 1 and 1 part by mass of 1,3,6,9,12-pentaoxacyclotetradecane-2-one (1-C) were mixed. The results thereof are shown in Table 4.

Example A4

A sheet-form nonaqueous electrolyte secondary battery of Example A4 was produced and evaluated in the same manner as in Example A1, except that 99 parts by mass of the standard electrolyte solution 1 and 1 part by mass of 1,3,6,9,11,14-hexaoxacyclohexadecane-2,10-dione (1-D) were mixed. The results thereof are shown in Table 4.

Example A5

A sheet-form nonaqueous electrolyte secondary battery of Example A5 was produced and evaluated in the same manner as in Example A1, except that 99 parts by mass of the standard electrolyte solution 1 and 1 part by mass of 1,3,6,9,12,14,17,20-octaoxacyclodocosane-2,13-dione (1-E) were mixed. The results thereof are shown in Table 4.

Example A6

A sheet-form nonaqueous electrolyte secondary battery of Example A6 was produced and evaluated in the same manner as in Example A1, except that 98.5 parts by mass of the standard electrolyte solution 1, 1 part by mass of 1,3,6,9-tetraoxacycloundecane-2-one (1-B) and 0.5 parts by mass of $LiPO_2F_2$ were mixed. The results thereof are shown in Table 4.

Example A7

A sheet-form nonaqueous electrolyte secondary battery of Example A7 was produced and evaluated in the same manner as in Example A1, except that 98.5 parts by mass of the standard electrolyte solution 1, 1 part by mass of 1,3,6,9,11,14-hexaoxacyclohexadecane-2,10-dione (1-D) and 0.5 parts by mass of $LiPO_2F_2$ were mixed. The results thereof are shown in Table 4.

Comparative Example A1

A sheet-form nonaqueous electrolyte secondary battery of Comparative Example A1 was produced and evaluated in the same manner as in Example A1, except that the standard electrolyte solution 1 was used as is. The results thereof are shown in Table 4.

TABLE 4

| | Compound of (a1) or (a2) | Other compound | Storage capacity retention rate (%) | Swelling in high-temperature storage (%) |
|---|---|---|---|---|
| Example A1 | 1-A | — | 92.5 | 80 |
| Example A2 | 1-B | — | 93.1 | 75 |
| Example A3 | 1-C | — | 93.9 | 58 |
| Example A4 | 1-D | — | 93.7 | 85 |
| Example A5 | 1-E | — | 94.0 | 73 |
| Example A6 | 1-A | $LiPO_2F_2$ | 93.8 | 68 |
| Example A7 | 1-D | $LiPO_2F_2$ | 93.7 | 70 |
| Comparative Example A1 | — | — | 91.3 | 100 |

As apparent from Table 4, it is seen that Examples A1 to A7 were superior to Comparative Example A1 in terms of the storage capacity retention rate and the swelling in storage (a smaller value represents that the battery was less likely to be swollen).

It is seen that, in Examples A1 to A7 where the compound of Formula (a1) or (a2) was used, a favorable effect of improving the storage capacity retention rate by at least 1.2% as compared to Comparative Example A1 was expressed. In addition, the swelling in high-temperature storage was improved by at least 15% as compared to Comparative Example A1. Moreover, even in Examples A6 and A7 where two kinds of electrolyte salts were used, it is seen that these effects of improving the storage capacity retention rate and the swelling in storage were maintained and expressed more favorably.

[Evaluation of Metal Amount after 14-Day Storage]

Comparative Example A2

The nonaqueous electrolyte secondary battery used in Comparative Example A1, whose storage capacity retention rate had been evaluated, was charged to 3.0 V and then disassembled to take out the negative electrode, and the mass of cobalt metal was measured.

Example A8

In the same manner as in Comparative Example A2, the nonaqueous electrolyte secondary battery used in Example A6, whose storage capacity retention rate had been evaluated, was disassembled to take out the negative electrode, and the mass of cobalt metal was measured. The relative value thereof is shown in Table 5, taking the mass of cobalt metal measured in Comparative Example A2 as 100.

Example A9

In the same manner as in Example A8, the nonaqueous electrolyte secondary battery used in Example A7, whose storage capacity retention rate had been evaluated, was disassembled to take out the negative electrode, and the mass of cobalt metal was measured. The result thereof is shown in Table 5.

Comparative Example A3

A sheet-form nonaqueous electrolyte secondary battery of Comparative Example A3 was produced and evaluated in the same manner as in Example A1 except that 99 parts by mass of the standard electrolyte solution 1 and 1 part by mass of 12-crown-4 shown below were mixed and, in the same manner as in Example A8, this nonaqueous electrolyte secondary battery was disassembled to take out the negative electrode, and the mass of cobalt metal was measured. The result thereof is shown in Table 5.

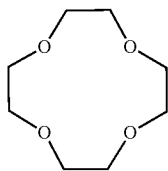 [SMILES: C1COCCOCCOCCO1]

TABLE 5

| | Compound of (a1) | Other compound | Metal amount after 14-day storage (%) |
|---|---|---|---|
| Example A8 | 1-A | $LiPO_2F_2$ | 91.2 |
| Example A9 | 1-D | $LiPO_2F_2$ | 94.5 |
| Comparative Example A2 | — | — | 100.0 |
| Comparative Example A3 | — | 12-crown-4, $LiPO_2F_2$ | 157.1 |

The mass of cobalt metal represents the amount of the transition metal that was eluted from the positive electrode and incorporated into the negative electrode. Therefore, a smaller value thereof indicates a less reduction in the capacity and the safety due to deterioration of the negative electrode coating film. As apparent from Table 5, it is seen that Examples A8 and A9 were superior to Comparative Examples A2 and A3 in terms of the amount of metal elution.

Example A10

[Production of Negative Electrode]

To 98 parts by mass of a carbonaceous material, 1 part by mass of an aqueous dispersion of sodium carboxymethyl cellulose (concentration of sodium carboxymethyl cellulose=1% by mass) and 1 part by mass of an aqueous dispersion of styrene-butadiene rubber (concentration of styrene-butadiene rubber=50% by mass) were added as a thickening agent and a binder, respectively, and these materials were mixed using a disperser to prepare a slurry. A 10 μm-thick copper foil was coated with the thus obtained slurry, and this copper foil was dried and then roll-pressed using a press machine to obtain a negative electrode.

[Production of Positive Electrode]

A slurry was prepared by mixing 90 parts by mass of $LiNi_{0.6}Mn_{0.2}Co_{0.2}O_2$ as a positive electrode active material, 7 parts by mass of acetylene black as a conductive material and 3 parts by mass of polyvinylidene fluoride (PVdF) as a binder in an N-methylpyrrolidone solvent. One side of a 15 μm-thick aluminum foil, which had been coated with a conductive auxiliary agent in advance, was coated with the thus obtained slurry, and this aluminum foil was dried and then roll-pressed using a press machine to obtain a positive electrode.

[Preparation of Electrolyte Solution]

Under a dry argon atmosphere, dried $LiPF_6$ was dissolved in a mixture of ethylene carbonate (EC), dimethyl carbonate (DMC) and ethyl methyl carbonate (EMC) (volume ratio=30:30:40) at a ratio of 1.0 mol/L to prepare a standard electrolyte solution 2. This standard electrolyte solution 2 in an amount of 99.5 parts by mass was mixed with 2 ppm by mass of 1,3,6-trioxocan-2-one (1-A) and 0.5 parts by mass of $LiPO_2F_2$, whereby an electrolyte solution of Example A10 was prepared.

[Production of Nonaqueous Electrolyte Secondary Battery]

The above-obtained positive electrode and negative electrode were laminated with a polyethylene separator, which had been impregnated with the above-obtained nonaqueous electrolyte solution in advance, in the order of the positive electrode, the separator, and the negative electrode. The thus obtained battery element was placed in a can for a 2032 coin-type battery, and the can was caulked using a caulking machine, whereby a coin-type nonaqueous electrolyte secondary battery of Example A10 was produced.

[Initial Charging and Discharging]

At 25° C., the thus obtained coin-type nonaqueous electrolyte secondary battery was charged to 4.2 V at a constant current equivalent to 0.3 C, further charged at a constant voltage of 4.2 V until the current value was reduced to 0.05 C, and then discharged to 2.5 V at a constant current of 0.3 C. Subsequently, the battery was charged to 4.1 V at a constant current of 0.3 C, further charged at a constant voltage of 4.2 V until the current value was reduced to 0.05 C, and then maintained at 25° C. for 2 hours to perform aging, after which the battery was discharged to 2.5 V at a constant current of 0.3 C and 25° C. Thereafter, the battery was charged to 4.2 V at a constant current equivalent to 0.3 C, further charged at a constant voltage of 4.2 V until the current value was reduced to 0.05 C, and then discharged to 2.5 V at a constant current of 0.3 C. In this manner, the coin-type nonaqueous electrolyte secondary battery was stabilized.

[Initial High-Current Discharging Test]

At 25° C., the thus stabilized coin-type nonaqueous electrolyte secondary battery was charged to 4.2 V at a constant current equivalent to 0.3 C, further charged at a constant voltage of 4.2 V until the current value was reduced to 0.05 C, and then discharged to 2.5 V at a constant current of 0.3 C. The discharge capacity in this process was defined as initial low-rate capacity. Subsequently, the battery was charged to 4.2 V at a constant current equivalent to 0.3 C, further charged at a constant voltage of 4.2 V until the current value was reduced to 0.05 C, and then discharged to 2.5 V at a constant current of 2 C. The discharge capacity in this process was defined as initial high-rate capacity.

The initial high-rate discharge performance (%) was calculated using the following equation:

Initial high-rate discharge performance (%)=100× (Initial high-rate capacity/Initial low-rate capacity)

[Repeated Charging-Discharging Test at 25° C.]

After the initial high-current discharging test, the nonaqueous electrolyte secondary battery was subjected to a 50-cycle repeated charging-discharging test in which each cycle consisted of, at 25° C., charging the battery to 4.2V at a constant current of 0.3 C, further charging of the battery at a constant voltage until the current value was reduced to 0.05 C, and subsequent discharging of the battery to 2.5 V at a constant current of 0.3 C.

[High-Current Discharging Test after Repeated Charging-Discharging Test]

After the 50-cycle repeated charging-discharging test, the nonaqueous electrolyte secondary battery was, at 25° C., charged to 4.2 V at a constant current equivalent to 0.3 C, further charged at a constant voltage of 4.2 V until the current value was reduced to 0.05 C, and then discharged to 2.5 V at a constant current of 0.3 C. The discharge capacity in this process was defined as post-test low-rate capacity. Subsequently, the battery was charged to 4.2 V at a constant current equivalent to 0.3 C, further charged at a constant voltage of 4.2 V until the current value was reduced to 0.05 C, and then discharged to 2.5 V at a constant current of 2 C. The discharge capacity in this process was defined as post-test high-rate capacity.

The post-test high-rate discharge performance (%) was calculated using the following equation:

Post-test high-rate discharge performance (%)=100×
(Post-test high-rate capacity/Post-test low-rate capacity)

Table 6 shows the values of the change in high-rate discharge performance (%), which were calculated by {(Post-test high-rate discharge performance)−(Initial high-rate discharge performance)}.

Example A11

A coin-type nonaqueous electrolyte secondary battery of Example A11 was produced and evaluated in the same manner as in Example A10, except that 99.5 parts by mass of the standard electrolyte solution 2, 2 ppm by mass of 1,3,6,9,11,14-hexaoxacyclohexadecane-2,10-dione (1-D) and 0.5 parts by mass of $LiPO_2F_2$ were mixed. The result thereof is shown in Table 6.

Example A12

A coin-type nonaqueous electrolyte secondary battery of Example A12 was produced and evaluated in the same manner as in Example A10, except that 99 parts by mass of the standard electrolyte solution 2, 0.5 parts by mass of 1,3,6,9-tetraoxacycloundecane-2-one (1-B) and 0.5 parts by mass of $LiPO_2F_2$ were mixed. The result thereof is shown in Table 6.

Example A13

A coin-type nonaqueous electrolyte secondary battery of Example A13 was produced and evaluated in the same manner as in Example A10, except that 99 parts by mass of the standard electrolyte solution 2, 0.5 parts by mass of 1,3,6,9,12-pentaoxacyclotetradecane-2-one (1-C) and 0.5 parts by mass of $LiPO_2F_2$ were mixed. The result thereof is shown in Table 6.

Example A14

A coin-type nonaqueous electrolyte secondary battery of Example A14 was produced and evaluated in the same manner as in Example A10, except that 99 parts by mass of the standard electrolyte solution 2, 0.5 parts by mass of 1,3,6,9,12,14,17,20-octaoxacyclodocosane-2,13-dione (1-E) and 0.5 parts by mass of $LiPO_2F_2$ were mixed. The result thereof is shown in Table 6.

Example A15

A coin-type nonaqueous electrolyte secondary battery of Example A15 was produced and evaluated in the same manner as in Example A10, except that 100 parts by mass of the standard electrolyte solution 2 and 2 ppm by mass of 1,3,6-trioxocan-2-one (1-A) were mixed. The result thereof is shown in Table 6.

Example A16

A coin-type nonaqueous electrolyte secondary battery of Example A16 was produced and evaluated in the same manner as in Example A10, except that 100 parts by mass of the standard electrolyte solution 2 and 10 ppm by mass of 1,3,6-trioxocan-2-one (1-A) were mixed. The result thereof is shown in Table 6.

Example A17

A coin-type nonaqueous electrolyte secondary battery of Example A17 was produced and evaluated in the same manner as in Example A10, except that 100 parts by mass of the standard electrolyte solution 2 and 2 ppm by mass of 1,3,6,9,11,14-hexaoxacyclohexadecane-2,10-dione (1-D) were mixed. The result thereof is shown in Table 6.

Example A18

A coin-type nonaqueous electrolyte secondary battery of Example A18 was produced and evaluated in the same manner as in Example A10, except that 100 parts by mass of the standard electrolyte solution 2 and 10 ppm by mass of 1,3,6,9,11,14-hexaoxacyclohexadecane-2,10-dione (1-D) were mixed. The result thereof is shown in Table 6.

Example A19

A coin-type nonaqueous electrolyte secondary battery of Example A19 was produced and evaluated in the same manner as in Example A10, except that 99.5 parts by mass of the standard electrolyte solution 2, and 0.5 parts by mass of 1,3,6,9,11,14-hexaoxacyclohexadecane-2,10-dione (1-D) were mixed. The result thereof is shown in Table 6.

Example A20

A coin-type nonaqueous electrolyte secondary battery of Example A20 was produced and evaluated in the same manner as in Example A10, except that 99.5 parts by mass of the standard electrolyte solution 2, and 0.5 parts by mass of 1,3,6,9-tetraoxacycloundecane-2-one (1-B) were mixed. The result thereof is shown in Table 6.

Comparative Example A4

A coin-type nonaqueous electrolyte secondary battery of Comparative Example A4 was produced and evaluated in the same manner as in Example A10, except that 99.5 parts by mass of the standard electrolyte solution 2, and 0.5 parts by mass of $LiPO_2F_2$ were mixed. The result thereof is shown in Table 6.

Comparative Example A5

A coin-type nonaqueous electrolyte secondary battery of Comparative Example A5 was produced and evaluated in the same manner as in Example A10, except that only the standard electrolyte solution 2 was used. The result thereof is shown in Table 6.

TABLE 6

|  | Compound of (a1) or (a2) | | Other compound | | Change in high-rate discharge performance (%) |
|---|---|---|---|---|---|
| Example A10 | 1-A | 2 ppm by mass | LiPO$_2$F$_2$ | 0.5% by mass | 14.6 |
| Example A11 | 1-D | 2 ppm by mass | LiPO$_2$F$_2$ | 0.5% by mass | 15.7 |
| Example A12 | 1-B | 0.5% by mass | LiPO$_2$F$_2$ | 0.5% by mass | 17.6 |
| Example A13 | 1-C | 0.5% by mass | LiPO$_2$F$_2$ | 0.5% by mass | 13.0 |
| Example A14 | 1-E | 0.5% by mass | LiPO$_2$F$_2$ | 0.5% by mass | 14.7 |
| Example A15 | 1-A | 2 ppm by mass | — | — | 5.2 |
| Example A16 | 1-A | 10 ppm by mass | — | — | 7.9 |
| Example A17 | 1-D | 2 ppm by mass | — | — | 6.0 |
| Example A18 | 1-D | 10 ppm by mass | — | — | 6.5 |
| Example A19 | 1-D | 0.5% by mass | — | — | 5.6 |
| Example A20 | 1-B | 0.5% by mass | — | — | 9.2 |
| Comparative Example A4 | — | — | LiPO$_2$F$_2$ | 0.5% by mass | 4.6 |
| Comparative Example A5 | — | — | — | — | 5.1 |

As apparent from Table 6, it is understood that Examples A10 to A20 were superior to Comparative Examples A4 and A5 in terms of the change in the high-rate discharge performance after the cycle charge-discharge test, and that the high-rate discharge performance was improved by the present invention. Particularly, according to the comparisons between Examples A10 to A14 and Comparative Example 4, it is seen that the use of the compound of Formula (a1) or (a2) in combination with LiPO$_2$F$_2$ can markedly improve, rather than deteriorate, the high-rate discharge performance even after a repeated charge-discharge test.

INDUSTRIAL APPLICABILITY

According to the nonaqueous electrolyte solution of the present invention, an energy device that hardly shows deterioration of its properties can be provided; therefore, this electrolyte solution can be suitably utilized in a variety of fields, such as electronic equipments in which an energy device is used.

Moreover, the nonaqueous electrolyte solution of the present invention is useful since it can improve the cycle capacity retention rate of a nonaqueous electrolyte secondary battery under endurance conditions of cycle operation and high-temperature storage, as well as the input-output characteristics (input-output retention rate) after cycle operation and the battery swelling. Therefore, the nonaqueous electrolyte solution of the present invention and an energy device using the same, such as a nonaqueous electrolyte secondary battery, can be used in a variety of known applications. Specific examples of such applications include laptop computers, stylus computers, portable computers, electronic book players, mobile phones, portable fax machines, portable copiers, portable printers, headphone stereos, video cameras, liquid crystal TVs, handy cleaners, portable CD players, mini-disc players, transceivers, electronic organizers, calculators, memory cards, portable tape recorders, radios, back-up power supplies, motors, automobiles, motorcycles, motor-assisted bikes, bicycles, lighting equipment, toys, gaming machines, watches, power tools, strobe lights, cameras, household backup power sources, backup power sources for commercial use, load leveling power sources, power sources for storing natural energy, and lithium ion capacitors.

The invention claimed is:

1. A nonaqueous electrolyte solution, comprising a compound represented by the following Formula (1):

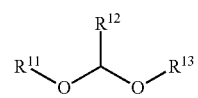

(1)

wherein R$^{11}$, R$^{12}$ and R$^{13}$ each independently represent an organic group having 1 to 3 carbon atoms; and R$^{11}$ and R$^{12}$, R$^{11}$ and R$^{13}$, or R$^{12}$ and R$^{13}$ are optionally bound with each other to form a 5-membered ring or a 6-membered ring, with a proviso that a total number of carbon atoms of R$^{11}$, R$^{12}$ and R$^{13}$ is 7 or less, and wherein a total content of the compound represented by Formula (1) is 0.05 ppm by mass to 50 ppm by mass with respect to a total amount of the nonaqueous electrolyte solution.

2. The nonaqueous electrolyte solution according to claim 1, further comprising at least one compound selected from the group consisting of a fluorine atom-containing cyclic carbonate, a carbon-carbon unsaturated bond-containing cyclic carbonate, a difluorophosphate salt, a fluorosulfate salt, an isocyanate group-containing compound, a cyano group-containing compound, a cyclic sulfonate ester, and a dicarboxylic acid complex salt.

3. The nonaqueous electrolyte solution according to claim 1, wherein, in Formula (1), R$^{11}$, R$^{12}$ and R$^{13}$ are each independently an organic group having 1 to 2 carbon atoms, and the total number of carbon atoms of R$^{11}$, R$^{12}$ and R$^{13}$ is 5 or less.

4. An energy device, comprising:
plural electrodes capable of absorbing and releasing metal ions; and
a nonaqueous electrolyte solution,
wherein the nonaqueous electrolyte solution is the nonaqueous electrolyte solution according to claim 1.

5. The energy device according to claim 4, wherein
the plural electrodes capable of absorbing and releasing metal ions are a positive electrode capable of absorbing and releasing metal ions and a negative electrode capable of absorbing and releasing metal ions, and
the negative electrode comprises a carbonaceous material or a silicon-containing material.

6. The energy device according to claim 4, wherein
the plural electrodes capable of absorbing and releasing metal ions are a positive electrode capable of absorbing and releasing metal ions and a negative electrode capable of absorbing and releasing metal ions, and
the positive electrode comprises a transition metal oxide.

7. A nonaqueous electrolyte solution, comprising at least one compound selected from the group consisting of compounds represented by the following Formulae (a1) and (a2):

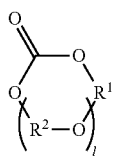
(a1)

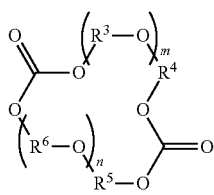
(a2)

wherein, $R^1$ to $R^6$ each independently represent an alkylene group having 2 to 4 carbon atoms, which may be straight-chain or branched-chain; l represents an integer of 1 to 6; and m and n each represent an integer of 0 to 6, with a proviso that, when either of m and n is 0, the other is an integer of 1 or larger.

8. The nonaqueous electrolyte solution according to claim 7, further comprising a fluorine atom-containing cyclic carbonate.

9. The nonaqueous electrolyte solution according to claim 7, further comprising a carbon-carbon unsaturated bond-containing cyclic carbonate.

10. The nonaqueous electrolyte solution according to claim 7, further comprising two or more kinds of lithium salts.

11. The nonaqueous electrolyte solution according to claim 7, further comprising an isocyanate group-containing compound.

12. The nonaqueous electrolyte solution according to claim 7, further comprising a cyano group-containing compound.

13. The nonaqueous electrolyte solution according to claim 7, further comprising an $SO_2$ group-containing cyclic compound.

14. An energy device, comprising:
plural electrodes capable of absorbing and releasing metal ions; and
a nonaqueous electrolyte solution,
wherein the nonaqueous electrolyte solution is the nonaqueous electrolyte solution according to claim 7.

15. The energy device according to claim 14, wherein
the plural electrodes capable of absorbing and releasing metal ions are a positive electrode and a negative electrode, and
the negative electrode comprises a carbonaceous material or a silicon-containing material.

16. The energy device according to claim 14, wherein
the plural electrodes capable of absorbing and releasing metal ions are a positive electrode and a negative electrode, and
the positive electrode comprises a transition metal oxide.

17. The nonaqueous electrolyte solution of claim 1, wherein
$R^{11}$, $R^{12}$ and $R^{13}$ each independently represent a hydrocarbon group.

* * * * *